United States Patent
Nibu et al.

(10) Patent No.: US 10,975,880 B2
(45) Date of Patent: Apr. 13, 2021

(54) PATIENT VENTILATION DEVICE INCLUDING BLOWER WITH SCALLOPPED SHROUD

(71) Applicant: ResMed Pty Ltd, Bella Vista (AU)

(72) Inventors: Adel Nibu, Grafrath (DE); Johannes Nickol, Neukenroth (DE); Achim Biener, Aufkirchen (DE); Johann Sebastian Burz, Germaringen (DE); Bernd Christoph Lang, Graefelfing (DE); Saad Nasr, Sydney (AU); Robert Eibl, Munich (DE); Andreas Kirchberger, Miesbach (DE); Christian Bayer, Penzberg (DE)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 16/773,300

(22) Filed: Jan. 27, 2020

(65) Prior Publication Data

US 2020/0158126 A1    May 21, 2020

Related U.S. Application Data

(63) Continuation of application No. 15/334,350, filed on Oct. 26, 2016, now Pat. No. 10,578,118, which is a (Continued)

(30) Foreign Application Priority Data

Oct. 29, 2009   (EP) .................................... 09174494

(51) Int. Cl.
  *F04D 29/28*   (2006.01)
  *A61M 16/00*   (2006.01)
  (Continued)

(52) U.S. Cl.
  CPC ....... *F04D 29/281* (2013.01); *A61M 16/0066* (2013.01); *A61M 16/0069* (2014.02);
  (Continued)

(58) Field of Classification Search
  CPC .... F04D 29/281; F04D 29/4246; F04D 29/30; A61M 16/0069; A61M 16/0875; A61M 16/16; A61M 16/0066; A61M 2205/42
  See application file for complete search history.

(56) References Cited

U.S. PATENT DOCUMENTS

| 985,279 A | 2/1911 | Ohlson |
| 3,714,944 A | 2/1973 | Price et al. |

(Continued)

FOREIGN PATENT DOCUMENTS

| CN | 1809397 A | 7/2006 |
| CN | 101321958 A | 12/2008 |

(Continued)

OTHER PUBLICATIONS

Office Action dated Jun. 4, 2019 issued in Japanese Application No. 2018-136532 with partial English translation (6 pages).

(Continued)

*Primary Examiner* — Eldon T Brockman
(74) *Attorney, Agent, or Firm* — Nixon & Vanderhye P.C.

(57) ABSTRACT

A blower for a respiratory apparatus includes an impeller configured to rotate to pressurize the supply of gas. The impeller includes a shroud with a plurality of vanes extending from a surface of the shroud toward the gas inlet. Each vane radiates outwards from a hub in the shroud that is configured to receive a motor shaft. The outer diameter of the shroud varies between maximum portions with a maximum outer diameter and minimum portions with a minimum outer diameter. The maximum portions are located at the vanes and the minimum portions are located between the (Continued)

vanes. In addition, each vane has an intermediate point located a predetermined distance from the hub that marks the beginning of a curvature of the vane in the direction of the impeller's rotation. The curvature of the vane is located between the intermediate point and the radially outermost end of the vane.

28 Claims, 30 Drawing Sheets

Related U.S. Application Data continuation of application No. 13/503,490, filed as application No. PCT/EP2010/066498 on Oct. 29, 2010, now Pat. No. 9,512,856.

(51) Int. Cl.
*F04D 29/42* (2006.01)
*A61M 16/08* (2006.01)
*A61M 16/16* (2006.01)
*F04D 29/30* (2006.01)
*A61M 16/10* (2006.01)

(52) U.S. Cl.
CPC ........ *A61M 16/0875* (2013.01); *A61M 16/16* (2013.01); *F04D 29/4246* (2013.01); *A61M 16/107* (2014.02); *A61M 2205/42* (2013.01); *A61M 2205/75* (2013.01); *F04D 29/30* (2013.01)

(56) References Cited

U.S. PATENT DOCUMENTS

| | | | |
|---|---|---|---|
| 3,746,467 A | 7/1973 | Buse | |
| 4,060,337 A | 11/1977 | Bell | |
| 4,944,310 A | 7/1990 | Sullivan | |
| 5,536,140 A | 7/1996 | Wagner et al. | |
| 5,605,444 A | 2/1997 | Paton | |
| 5,701,883 A | 12/1997 | Hete et al. | |
| 6,111,748 A | 8/2000 | Bhatia | |
| 6,231,053 B1 | 5/2001 | Wakamatsu | |
| 6,499,954 B1 | 12/2002 | Adonakis | |
| 6,881,033 B2 | 4/2005 | Makinson | |
| 7,210,903 B2 | 5/2007 | Lyons | |
| 8,567,190 B2 | 10/2013 | Sumser et al. | |
| 9,512,856 B2 | 12/2016 | Nibu et al. | |
| 10,137,264 B2* | 11/2018 | Darby | F04D 29/30 |
| 10,286,167 B2* | 5/2019 | Bothma | G01F 1/0755 |
| 10,293,125 B2 | 5/2019 | Jeha et al. | |
| 2001/0036405 A1 | 11/2001 | Yokoyama | |
| 2002/0119044 A1 | 8/2002 | O'Connor | |
| 2002/0163139 A1 | 11/2002 | Poquet et al. | |
| 2003/0007327 A1 | 1/2003 | Fujiwara | |
| 2003/0082016 A1 | 5/2003 | Eavenson | |
| 2005/0089409 A1 | 4/2005 | Boohar | |
| 2005/0103339 A1 | 5/2005 | Daly | |
| 2005/0163614 A1 | 7/2005 | Chapman | |
| 2006/0078423 A1 | 4/2006 | Zheng | |
| 2007/0131228 A1 | 6/2007 | Croll et al. | |
| 2008/0076962 A1 | 3/2008 | Miyagawa et al. | |
| 2008/0309027 A1 | 12/2008 | Rogeon et al. | |
| 2009/0044835 A1 | 2/2009 | Peters | |
| 2009/0136341 A1 | 5/2009 | Kenyon | |
| 2010/0166539 A1 | 7/2010 | Ibaraki et al. | |
| 2011/0110774 A1 | 5/2011 | Horng | |
| 2012/0285454 A1 | 11/2012 | Nibu et al. | |
| 2014/0216460 A1* | 8/2014 | Bothma | G01F 1/075 128/204.18 |
| 2017/0082116 A1 | 3/2017 | Nibu et al. | |
| 2019/0262561 A1* | 8/2019 | Bothma | F04D 25/082 |

FOREIGN PATENT DOCUMENTS

| | | |
|---|---|---|
| CN | 101450237 A | 6/2009 |
| CN | 101820805 A | 9/2010 |
| DE | 30 11 287 A1 | 10/1981 |
| DE | 102007028742 A1 | 12/2008 |
| EP | 0 872 643 | 10/1998 |
| EP | 1270037 A1 | 1/2003 |
| EP | 1 527 996 | 5/2005 |
| GB | 707616 | 4/1954 |
| GB | 772 888 | 4/1957 |
| GB | 1 345 442 | 1/1974 |
| GB | 1 407 408 | 9/1975 |
| JP | 61-87567 A | 5/1986 |
| JP | 8-128609 | 5/1996 |
| JP | 3049251 U | 6/1998 |
| JP | 2001-057220 A | 2/2001 |
| JP | 2004-524088 A | 8/2004 |
| JP | 2006-223339 A | 8/2006 |
| JP | 2006-283689 A | 10/2006 |
| JP | 2007-512047 A | 5/2007 |
| JP | 2008-73212 | 4/2008 |
| JP | 2008-511358 A | 4/2008 |
| KR | 10-2006-0089125 A | 8/2006 |
| KR | 20090007771 A | 1/2009 |
| WO | 2002/066107 A1 | 8/2002 |
| WO | 2005/051468 A1 | 6/2005 |
| WO | 2006/024735 A2 | 3/2006 |
| WO | 2006/0245321 A1 | 3/2006 |
| WO | 2006/088007 A1 | 8/2006 |
| WO | 2006/125252 A1 | 11/2006 |
| WO | 2007/004898 A1 | 1/2007 |
| WO | 2007/134405 A1 | 11/2007 |
| WO | 2008/102216 A1 | 8/2008 |

OTHER PUBLICATIONS

Further Examination Report dated Jul. 29, 2013 issued in New Zealand Application No. 598931 (2 pages).
Further Examination Report dated Aug. 6, 2014 issued in New Zealand Application No. 598931 (2 pages).
Communication dated Dec. 22, 2017 issued in European Application No. 10 796 302.7 (4 pages).
Office Action dated Mar. 15, 2018 issued in Chinese Application No. 201610255157.8 with English translation (15 pages).
Notification for Reasons of Refusal dated Jan. 9, 2018 issued in Japanese Application No. 2015-113397 with English translation (12 pages).
Office Action dated Nov. 14, 2017 issued in Japanese Application No. 2017-001121 with English translation (12 pages).
Communication dated Sep. 29, 2017 issued in European Application No. 09174494.6 (4 pages).
Office Action dated Apr. 14, 2017 issued in Japanese Application No. 2015-113397 with English translation (11 pages).
Final Rejection dated Sep. 6, 2016 issued in Japanese Application No. 2015-113397 with English translation (5 pages).
The Fourth Office Action dated Nov. 13, 2015 issued in Chinese Application No. 201080059533.7 with English translation (7 pages).
Office Action dated May 17, 2016 issued in Japanese Application No. 2015-113397 with English translation (6 pages).
Patent Examination Report No. 3 dated Dec. 11, 2014 issued in Australian Application No. 2010311388 (7 pages).
Patent Examination Report No. 1 dated Jun. 11, 2013 issued in Australian Application No. 2010311388 (3 pages).
Patent Examination Report No. 1 dated Nov. 17, 2015 issued in Australian Application No. 2015202731 (3 pages).
Chinese Office Action dated Mar. 17, 2015 in Chinese Application No. 201080059533.7 with English translation (17 pages).
Office Action dated Aug. 4, 2014 in Chinese Application No. 201080059533.7 with English translation (14 pages).
Extended European Search Report for corresponding EP Application No. 09174494, dated Mar. 31, 2010, 5 pages.
International Search Report for PCT/EP2010/066498, dated Dec. 30, 2011.
Written Opinion for PCT/EP2010/066498, dated Dec. 30, 2011.

(56) References Cited

OTHER PUBLICATIONS

Patent Examination Report No. 2 dated Jul. 21, 2014 in Australian Application No. 2010311388 (6 pages).
Office Action dated Sep. 6, 2016 issued in Japanese Application No. 2015-113397 with English translation (4 pages).
First Office Action dated Jun. 2, 2020 issued in Chinese Application No. 201910034841.7 with English translation (18 pages).

* cited by examiner

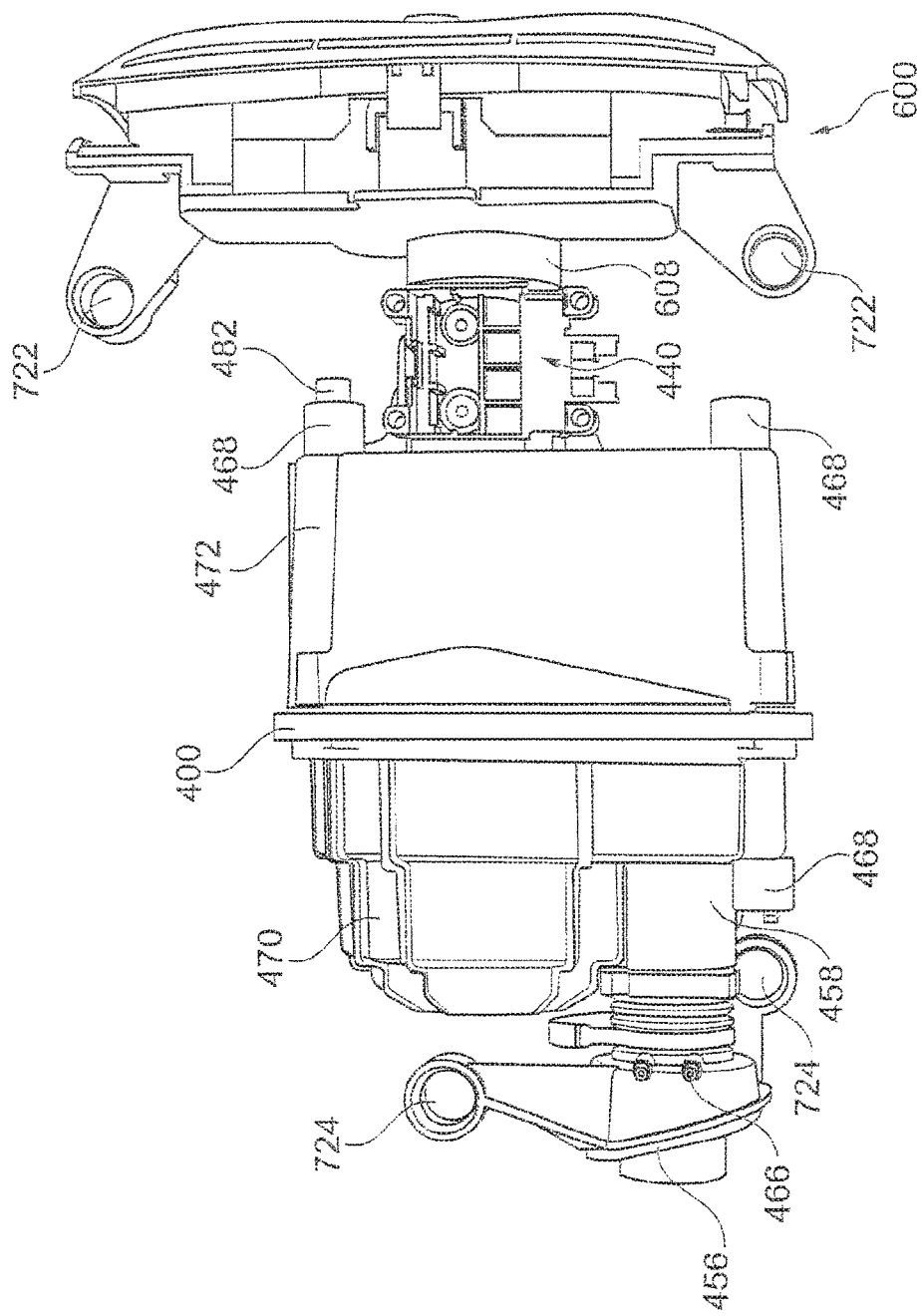

PATIENT VENTILATION DEVICE INCLUDING BLOWER WITH SCALLOPPED SHROUD

This application is a continuation of U.S. application Ser. No. 15/334,350, filed Oct. 26, 2016, now allowed, which is a continuation of U.S. application Ser. No. 13/503,490, filed Apr. 23, 2012, now U.S. Pat. No. 9,512,856, which is the U.S. national phase of International Application No. PCT/EP2010/066498 filed 20 Oct. 2010 which designated the U.S. and claims priority to EP Patent Application No. 09174494.6 filed 29 Oct. 2009, the entire contents of each of which are hereby incorporated by reference.

The invention relates to a patient ventilation or breathing device and components therefore for use in all forms of respiratory apparatus ventilation systems including invasive and non-invasive ventilation, positive airway pressure therapy, Continuous Positive Airway Pressure (CPAP), and particularly Bi-Level therapy and treatment for sleep disordered breathing (SDB) conditions such as Obstructive Sleep Apnea (OSA), and for various other respiratory disorders and diseases. The invention particularly relates to a blower, to a blade, to a gasket, to a cable, to an impeller, to a gas inlet and inlet member, to an improved air path or fluid flow path and components thereof, and/or to a modular ventilation or breathing device as referred to above and particularly incorporating one or more of the other aspects of the invention.

Respiratory disorders and diseases such as sleep disordered breathing (SDB) conditions such as Obstructive Sleep Apnea (OSA) etc. are known and various therapies for treating patients suffering of such disorders or diseases have been developed. Therapies for treating such disorders and diseases include, invasive and non-invasive ventilation, positive airway pressure therapy, Continuous Positive Airway Pressure (CPAP), Bi-Level therapy and treatment.

For example, Nasal Continuous Positive Airway Pressure (CPAP) treatment of Obstructive Sleep Apnea (OSA) was invented by Sullivan (see U.S. Pat. No. 4,944,310). An apparatus for treating, e.g., OSA typically comprises a blower that provides a supply of air or breathable gas to a patient interface, such as a mask, via an air delivery conduit.

Such therapy is generally applied for many hours and even up to 24 hours per day while the night time is a preferred application period. Thus, patients typically sleep while wearing the device. It is therefore desirable to have a system which is quiet and comfortable. In addition, it is desirable to have a system which is effective and reliable and which allows a fast reaction on changing patient parameters. Moreover, it is desirable to provide a system which is easy to manufacture, assemble and maintain. Also, it is desirable to provide a system which is more flexible as regards its modes and way of use. In order to improve the patients' mobility it is furthermore desirable to provide a flexible and mobile breathing device.

Patient ventilation or breathing devices for application of such therapies are known in the art. Although many improvements have been made in the recent years known systems still suffer from slow response times, high weight and large dimensions, a complex structure, as well as from high power consumption.

Such devices, i.a., generally comprise blowers or air pumps for delivering air to the patient at a (or differing) required pressure(s). Blowers are typically classified as centrifugal, axial or mixed flow. Generally, blowers comprise two main parts: a rotating part, namely an impeller and shaft; and a stationary part that defines a fluid flow path, typically a chamber such as a volute. Rotation of the impeller imparts kinetic energy to the air. The stationary part redirects the air expelled from the impeller into an enclosed outlet passage. During this redirection, resistance is encountered to flow because of the pressure generated by downstream resistance or a downstream pressure source. As the flow is slowed against this resistance, a portion of the kinetic energy is converted to potential energy in the form of pressure.

Generally, the faster the impeller is rotated, the higher the pressure that will be developed. A less effective blower generally will have to rotate its impeller faster to generate the same pressure as a more effective blower. Generally, running a given blower slower makes it quieter and prolongs its life time. Needless to say, there are further influences on a blowers effectiveness such as, e.g., size and weight distribution. Hence, it is generally desirable to make blowers more effective at generating a supply of air at positive pressure. In addition, it is a general desire to make blowers more quiet. Moreover, there is the need of providing a system, particularly a blower which has good acceleration properties and allows good response characteristics, particularly for providing alternating pressures, and simultaneously achieves a high flow and pressure output.

With reference to FIGS. 1 and 2, derived from prior art discussion in WO-A-2007/134405, three directions of a blower are defined, i.e., radial R, tangential T and axial A. Prior art centrifugal blower 10 includes an outlet 20, an inlet 30, an electric motor 40, an impeller 50 and a shaft 60. Arrows 70 indicate the general direction of airflow. Air enters the blower at the inlet 30 and is accelerated by the rotating impeller. The rotation imparted by the impeller generally directs the airflow in a tangential direction T. The volute then constrains the airflow to spiral the volute. The airflow then exits the blower in a generally tangential direction T via the outlet 20.

In some blowers, such as axially developed volute blowers, the volute geometry directs the tangential spiraling airflow in a slight axial direction A prior to exiting the blower in a generally tangential direction T.

The performance of a blower is often described using fan curves, which show the flow rate of air versus outlet pressure of air. Many factors affect the fan curve including impeller diameter and the number and shape of the impeller blades. The design process is a complex balance between competing priorities such as desired pressure, flow rate, size, reliability, manufacturability and noise. While many combinations of size, shape and configuration of components may produce a flow of pressurized air, such a result may be far from optimal, or be impractical.

A disadvantage of prior art blowers is they tend to suffer from noise emission. It has been observed that beside the acoustic noise there is also noise on the flow signal which may lead to difficulties or even errors in proper detection of the flow signal and thus to disadvantageous settings of the breathing device.

Although many attempts have been made in the art in order to improve blowers, there remains the need for an improved, simple, reliable, safe, effective and efficient blower which overcomes the disadvantages of the prior art.

In addition and in combination with the general design of the blower as referred to above, the design of the impeller has huge impact on the overall functionality, noise and effectiveness of the blower. Thus, there is the need for an improved, simple, reliable, safe, quiet, effective and efficient impeller which overcomes the disadvantages of the prior art.

In addition and in combination with the general design of the blower and/or the impeller as referred to above, the design and arrangement of the fluid flow path, along which the breathable gas is directed, and its components in a ventilation or breathing device and of the components of the ventilation or breathing device has huge impact on the overall functionality, noise and effectiveness of the ventilation or breathing device. This particularly applies for devices or therapies where additional gases, such as oxygen, are to be added to the flow of breathing gas. In this context, it is an additional aim to provide a safe and reliable provision of oxygen in order to reduce the risk of fire should sparking occur within the apparatus. Thus, there is the need for the provision of an improved, simple, safe, reliable, effective and efficient fluid flow path and its components.

For example, WO-A-2007/004898 relates to a breathing assistance apparatus including a manifold that is provided with or retrofittable to gas supply and humidifying devices. The manifold allows gases from an oxygen concentrator to be combined with the flow through a gases supply and humidifying device, most usually air. The combined output of oxygen and other breathing gases (air) is then humidified. With this breathing assistance apparatus and manifold oxygen is added to the input air stream of a gases supply via an oxygen inlet port extending from the side of the manifold and its ambient air inlet aperture.

U.S. Pat. No. 5,701,883 discusses an oxygen mixing arrangement for or in a pressure support ventilator, in which a modular oxygen-providing assembly is selectively insertable into a greater respiration apparatus. A valving arrangement and metering for supplying the oxygen is used which is added downstream from a valving arrangement used for venting patient exhaust flow and for controlling system pressure by venting excess gas flow to the ambient atmosphere.

These known devices still do not allow a safe, easy and reliable mixing of e.g. oxygen with the breathing gas flow.

WO-A-2008102216 relates to a gas supply unit for supplying pressurised gas to a patient, wherein it comprises: a pneumatic housing for supplying a flow of gas to the patient; a control housing (20) for controlling the flow of gas to be supplied to the patient; and a power supply housing (30) for supplying power to the unit (1). The three housings are distinct from one another and are designed for being removably coupled together to form a single unit.

The known concepts and designs of fluid flow paths and breathing devices still need further improvement, particularly as regards ease of manufacture, maintenance, functionality and/or safety.

In summary, there is the need for an improved patient ventilation or breathing device and its components which overcomes the disadvantages of the prior art. In particular, there is the need for a reliable, safe, easy to manufacture, quiet, efficient and effective device and its components which is flexible and easy to handle and to maintain.

It is an object underlying the present invention to provide an improved patient ventilation or breathing device as well as improved components for a patient ventilation or breathing device, particularly with regard to the disadvantages of the prior art and the needs referred to above.

These and further objects, as are apparent from the above discussions of the prior art and its drawbacks as well as from the below discussion of the invention and its advantages, are fulfilled by the combination of features of the independent claims (and aspects as discussed below) while the dependent claims refer to preferred embodiments and aspects of the present invention.

The invention relates to a patient ventilation or breathing device and components therefore for use in all forms of respiratory apparatus ventilation systems including invasive and non-invasive ventilation, positive airway pressure therapy, Continuous Positive Airway Pressure (CPAP), and particularly Bi-Level therapy and treatment for sleep disordered breathing (SDB) conditions such as Obstructive Sleep Apnea (OSA), and for various other respiratory disorders and diseases. The invention particularly relates to a blower and to a blade for use with and/or in combination with such blower. The invention alternatively or additionally relates to an impeller, particularly for use with blowers as referred to above and particularly for use with a blower according to the present invention. The present invention alternatively or additionally relates to an improved air path or fluid flow path and components thereof and therefore for use in ventilation or breathing devices as referred to above and particularly for use with a blower and/or impeller according to the present invention. Alternatively or additionally, the invention relates to a modular ventilation or breathing device as referred to above and particularly incorporating a blower, impeller and/or flow path according to the present invention. Alternatively or additionally, the present invention relates to a gasket and a cable to be used in ventilation or breathing devices as referred to above and particularly for use with the further aspects of the present invention. Alternatively or additionally, the invention also relates to a gas inlet and inlet member to be used in ventilation or breathing devices as referred to above and particularly for use with one or more of the further aspects of the invention such as the blower, impeller, gasket, modular ventilation or breathing device, and/or cable according to the present invention. Additionally, the present invention relates to patient ventilation or breathing devices incorporating the above inventions.

An aspect of the invention is directed to a blower or air pump for quietly and effectively providing a supply of air at positive pressure. Such blower is preferably a blower for a patient ventilation or breathing device, particularly for use in treatment of respiratory diseases or disorders as discussed in the introductory portion of the present invention as well as for use with the further aspects of the present invention. Such blower comprises a stationary part which may be a housing and, more particularly, may take the form of a volute. The blower further comprises a rotating portion to be coupled to a drive means, preferably an electric motor.

The blower furthermore comprises an air inlet and an air outlet. The air inlet may be axially arranged, wherein the air outlet may be tangentially arranged. The air outlet is split into at least two channels, preferably two channels which may be parallel. Preferably, the air outlet is of substantially radial cross-sectional shape wherein the outlet may be split such that, e.g, each of the two channels has a semi-circular cross-section. Alternatively, each of, e.g., four channels may have the cross section of a quadrant. The split of the air outlet is achieved by means of at least one blade dividing the outlet into the at least two, preferably parallel, channels. The blade, which forms part of the stationary portion, preferably extends parallel to the direction of the air flow through the outlet and/or to the longitudinal axis of the air outlet. The blade preferably extends in a plane defined by two axes, one being generally parallel and one being generally perpendicular to the axis of the volute. Preferably, the air inlet is defined as a cylinder or tube like inlet member extending from the interior of the blower.

According to a preferred embodiment, air enters the blower at the inlet and is accelerated by the rotating impeller. The rotation imparted by the impeller generally directs the air flow radially outwards in a tangential direction T. The volute then constrains the air flow to spiral the volute. The air flow then exits the blower in a generally tangential direction T via the split outlet.

Preferably, the outlet channel and the channels achieved by the split of said channel by means of the blade according to the invention, respectively, include a turn of the flow path about preferably an angle between about 70° to 110° and preferably of about 90°. Preferably, the turn is such that the turn of the flow path in the outlet channel is such that the air exits the outlet channel in a direction parallel to the axial direction, preferably parallel to the air inlet and preferably in the contrary direction to the air inlet. In other words, the air preferably enters the blower in one direction and exits the blower in the opposite direction.

In this embodiment, the blade preferably extends along the turn of the flow path in the outlet and preferably comprises two portions, each having a longitudinal axis, wherein these longitudinal axes enclose an angle lying in the plane of the blade and corresponding to the angle of the turn of the blower outlet. Preferably, said angle lies in the range of about 70° to 110° and preferably is about 90°.

Preferably, the blade is formed integral with the blower housing or at least one part thereof such as with the volute or one part of its housing, e.g., by means of plastic injection moulding. Preferably, the material of the blower is a biocompatible plastic of low flammability. However, it will be appreciated that other ways of manufacture and other materials may be applied.

The present invention alternatively and additionally relates to a blade for use with a, preferably radial, blower for providing supply of positive pressure, and preferably with a blower according to the present invention. The blade is adapted to fit into an air outlet of the blower and to split the outlet into at least two, preferably parallel, channels. According to a preferred embodiment, the blade preferably extends along the whole length of the outlet channel. Preferably, the blade comprises at least two portions or sections, each having a longitudinal axis extending in the plane of the blade, wherein the two longitudinal axes are inclined vis-à-vis one another in the plane of the blade and include an angle of about 70° to 110°, preferably of about 90°. Preferably, the blade is L-shaped. The blade according to the present invention is preferably made of the same material as (the stationary part of) the blower. Such blade preferably corresponds to the blower's blade referred to above apart from being integrally formed with a part of a blower housing.

The blower according to the present invention is advantageous and particularly has reduced noise emission. This has been proven by comparative tests between identical blowers under identical operating conditions with and without a blade according to the present invention. At the same time, the flow and pressure of the air flow pumped by the blower is not negatively impaired by the present invention. Preferred forms and features of the blower or blade, as referred to above relate to additional improvements vis-à-vis blowers without a blade. The solution according to the present invention is simple, reliable, and easy to manufacture.

In one form of the invention suitable for respiratory devices the blower comprises at least one impeller preferred embodiments of which will be discussed further below.

In one form, the blower has one stage, in other forms of the invention, the blower has more than one stage. In forms of the invention where multiple stages are used along an axis, the motor may be positioned in the centre and similar numbers of impellers may be positioned on either side of the motor along the axis.

Preferably, a motor is provided on the blower side axially opposite to the axially arranged inlet opening.

An additional and/or alternative aspect of the present invention relates to an impeller, particularly for use with blowers for use in medical devices and particularly for use in all forms of respiratory apparatus ventilation systems as referred to in the introductory portion of the present invention and particularly for use with the blower and/or the further aspects of the present invention.

The impeller preferably comprises a plurality of vanes extending from a disk-like shroud. The shroud, located downwardly or away from the air inlet in the direction of air flow, preferably has a generally disk-like shape.

The shroud preferably has a wavy or saw tooth shaped outer circumference in an axial or bottom view wherein the outer diameter of the shroud varies between a maximum outer diameter and a minimum outer diameter. Preferably, the maximum outer diameter is reached in a vicinity of the outer tips of the vanes while the minimum outer diameter is reached between two adjacent vanes, preferably between each pair of adjacent vanes.

The vanes extend, preferably vertically, from the shroud and are preferably formed integrally with the shroud. The impeller has an axis of rotation and is preferably of general rotational symmetry with regard to said axis.

Preferably, the vanes are radially arranged and extend from an inner diameter to an outer diameter. Preferably, the vanes have a substantially uniform height from their starting point at their inner diameter close to the impeller's axis of rotation until a first intermediate diameter; and a decreasing height from said first intermediate diameter towards their end at an outer diameter, the first intermediate diameter lying between the inner and outer diameters. Preferably, the blades are substantially straight from their starting point at their inner diameter close to the impeller's axis of rotation until a second intermediate diameter; and are curved from said second intermediate diameter towards their end at the outer diameter, the second intermediate diameter lying between the inner and outer diameters. Preferably, the second intermediate diameter preferably lies between the first intermediate diameter and the outer diameter. Alternatively, the second intermediate diameter preferably lies between the inner diameter and the first intermediate diameter or equals the first intermediate diameter. The curvature can be either positive or negative while it is preferably that the curvature is negative, i.e., away from the direction of rotation.

The geometry of the increase in height is preferably aligned with the geometry of the housing or stationary part and preferably corresponds thereto.

The impeller according to the present invention preferably has an inertia or moment of inertia of below about $3.2$ g cm$^2$ and preferably of below about $2.5$ g cm$^2$. Preferably the moment of inertia lies in a range between about $1.2$ and $3.2$ g cm$^2$ and preferably between about $1.2$ and $2.5$ g cm$^2$ and preferably is about $2.2$ g cm$^2$.

The impeller according to the present invention is preferably made of plastic, preferably $O_2$ resistant plastic and/or preferably unfilled plastic material.

The impeller according to the present invention is advantageous and particularly has reduced noise emission, a large pressure delivery for a given motor speed, allows supply of a given pressure at a relatively low motor speed, and has a fast response time. Furthermore, the impeller according to the present invention preferably provides a rigid impeller with comparatively low inertia. The impeller according to the present invention is particularly suitable for high-speed rotation, e.g. of about 50 k r/min. The impeller is particularly quiet, high efficient, allows fast motor acceleration to respond to the patient needs and exhibits very low stress at high speed. This particularly enables it to cycle between high and low speeds for ventilation and VPAP/BiPAP with very low risk of fatigue failure due to low alternating stress level.

The present invention additionally and alternatively relates to a gasket and an air path for use in ventilation or breathing devices as referred to above and particularly for use with a blower, impeller and/or the further aspects of the present invention.

The gasket according to the present invention is, i.a., adapted to sealingly separate a high pressure area of a ventilation and breathing device from a low or ambient pressure area. The gasket preferably furthermore allows an advantageous arrangement of different areas and/or components of a blower and particularly of the blower, the flow path and/or muffling chamber(s).

The gasket preferably has a core of a comparatively hard material, when compared to an outer material of the gasket, and preferably a core being made of aluminium. Said core is provided with one or more structural elements, particularly for allowing air to be pumped from a low pressure area to a high pressure area by means of, e.g., a blower, preferably a blower according to the present invention. The gasket in accordance with the present invention is furthermore preferably provided with structural elements which are suitable for providing a suspension to a blower, for sealingly connecting the gasket to a first and/or second part of a housing defining an air path.

Said gasket is provided with a skin or coating of elastic plastic material. Said material is comparatively softer than the core of the gasket and preferably is silicone. Silicone is particularly preferred since it enhances $O_2$ resistance, is biocompatible and has advanced dampening and sealing characteristics. Preferably, substantially the entire core of the gasket is provided or coated with such skin. In this context, 'substantially' is understood to mean more than 80% and preferably more than 90% and further preferred more than 95% and up to 100% of the core's surface area. In particular, depending on the way of coating, certain portions of the core may remain uncoated. This is particularly the case if the core is held or supported by support means during coating so that no coating or skin will be applied at the contact portions between support member and core.

Such gasket is preferably advantageous in that it allows a sealing separation of a high pressure and low pressure area and defining at least two compartments in the ventilation and breathing device. Preferably, the gasket is adapted to sealingly contact a first part of a housing which is provided with two chambers being open to one side of said first housing part wherein both chambers open towards the same side of the first housing part. One of said chambers defines a high pressure area and the second chamber defines a low pressure area, the first part of the housing and thus each chamber of the housing sealingly contacting one side of the gasket. In addition, the gasket of the present invention provides support and suspension for a blower to be mounted to the gasket. Here, the gasket inherently provides parts, preferably substantial parts of the required fastening, supporting and dampening means for such blower. Thus, the blower, and its motor, can be mounted to the gasket on one side thereof wherein the core of a relatively hard material provides a supporting structure while the elastic plastic skin of the gasket is adapted to provide connection and support means which particularly allow a sealed and dampened connection between gasket and blower.

At the same time, the blower and motor is advantageously positioned so that air can be sucked in or ventilated from the low pressure chamber through the gasket into the blower and then, at elevated pressure, to the high pressure area. Preferably, the high pressure area or chamber and the low pressure area or chamber are provided next to one another in a first part of a housing and are both sealingly closed at one of their sides by means of the gasket.

The gasket according to the present invention preferably has flat or substantially planar extensions while it is understood that the gasket is not exactly planar but provided with various structural elements, such as lips, rims, flanges, or elevations, for sealing connection with one or more parts of a housing, for positioning said housing and/or for supporting, dampening and positioning of parts attached to the gasket, e.g., the blower. Preferably, the gasket is adapted to sealingly close two housing parts, preferably each located at one side of the gasket. The first part of the housing preferably defines or is separated into a high pressure compartment and a low pressure compartment. The second part of the housing preferably also comprises two chambers or compartments one of which houses and supports the blower while the second one provides a path for the pressurised air be lead from the high pressure chamber defined in the first part of the housing through the gasket and towards the outlet of the device, e.g., into a hose directing the pressurized air to a patient. The first and second chambers defined by the first part of the housing and the gasket are preferably filled with a dampening or muffling material and are preferably foam filled and even more preferably silicone foam filled.

The air path is thus preferably defined by the gasket and at least one part of a housing, preferably two parts, being in sealing contact with the gasket.

In order to allow circulation of air from the low pressure chamber into the blower, which is located on the other side of the gasket vis-à-vis such low pressure chamber, and then from the blower into the high pressure chamber, which is again located on the other side of the gasket vis-à-vis the blower and then preferably back to the other side of the gasket into an pressurized air leading path, the gasket preferably comprises three, and preferably at least three, openings to allow air to flow from one side of the gasket to the other.

In the region of at least one, preferably two, of such holes the skin of the gasket provides combined sealing and connection means, particularly for sealingly supporting and dampening the blower. The sealing and connection means is preferably adapted as an opening rim, preferably ring-shaped, into or through which a part of the blower, preferably the inlet and/or outlet channel, can be pushed. The rim then sealingly connects to the blower. Preferably, the rim is supported on or to the core of the gasket by means of a suspension and/or dampening structure, such as a bellow, which is also formed by the skin or coating. While it is understood that the provision of one gasket with one planar core is preferred, there may alternatively be provided e.g. two or more separate cores and/or core(s) which may extend in different planes.

The gasket according to the present invention provides various combined and improved functionalities such as support of the housing parts and/or the blower, dampening of the housing parts and/or the blower, sealing different parts of the housings, such as the different pressure areas, and muffling. At the same time the gasket preferably is, particularly due to the silicone skin and its structural arrangement, of increased $O_2$ safety, being non-aging and allowing improved connection of, e.g., the housing and the blower as well as positioning thereof. In particular, the gasket according to the present invention significantly improves the design, size and arrangement of the air path and its components and supports and improves the ease and quality of assembly.

Particularly by the provision of the improved functionalities in accordance with the gasket of the present invention there is provided a structure reducing leakage along the air path, which assists in reduction of number of the parts and improves the quality and time required for assembly and which assists an improved size and modularity of the ventilation device. In particular, the gasket according to the present invention allows a separation of the air path from other parts of the ventilation or breathing device, such as from the electronics, thereby increasing hygiene and safety. Moreover, the gasket according to the present invention allows the provision of a separable and exchangeable air path, particularly of a small air path including few components and allowing an improved air flow with good noise reduction.

The gasket according to the present invention thus allows an arrangement in which a, preferably sensorless, blower unit is arranged outside the air path, improving hygene and safety and additionally leading to a reduction of costs, parts, required space etc.

The present invention additionally and alternatively relates to a cable to be used in ventilation or breathing devices as referred to above and particularly for use with a blower, impeller, gasket and/or the further aspects of the present invention.

The improved, preferably self-sealing, cable according to the present invention comprises a silicone coating. Preferably, there are provided two or more, preferably four or more, and even more preferred six or more metal wires, preferably stranded wires or litz wires. These metal wires are located next to one another, preferably generally in one plane or in a circular or oval arrangement while being distanced from one another. These wires are provided with one silicone coating which is directly applied to the wire, i.e., with no intermediate sheath or the like between the wire and the silicone coating.

The self-sealing cable according to the present invention is of particular advantage in that it provides electronic insulation of the different metal wires vis-à-vis one another and the surrounding, exhibits an improved $O_2$ safety and can be clamped between two parts in a self-sealing manner. In other words, the self-sealing cable according to the present invention can extend through the contact region between, e.g., two housing parts connected to one another and can extend from an inner side of such housing to an outer side thereof in a sealed manner without the need for any additional sealing material and the like. The self-sealing cable according to the present invention is in sealing contact with the parts, here the parts of a housing, between which it extends without the need of any particular additional sealing means or the like. The silicone coating preferably has a certain minimum thickness, e.g., of at least 0.5 mm measured along the shortest distance from the outer circumference or surface of the cable to one of the wires.

Such cable is preferably adapted for use with a blower and preferably with the blower according to the present invention and allows power supply, control and the like of said blower. Even more preferred, the self-sealing cable according to the present invention is used in combination with the gasket according to the present invention and preferably also the blower according to the present invention so that the blower can be located in the air path while the cable extends from the motor inside the air path to the outside of this air path in a self-sealing manner, thereby increasing the freedom of construction, ease of manufacture and assembly and the like. Although not specifically required, certain dimensions of contact regions for leading the self-sealing cable according to the present invention in a sealing manner through the contact region of two contacting parts may be of further advantage. In particular, a predefined gap between the two parts is provided with the general shape of and slightly smaller dimensions than the cable.

The invention additionally and alternatively relates to an inlet member including an inlet filter for ventilation or breathing devices as referred to above and particularly for use with a blower, impeller, gasket and/or the further aspects of the present invention. According to a preferred embodiment, the inlet member forms part of the air path as described above.

Such inlet member preferably comprises an inlet housing comprising at least a first part and a second part. Preferably, the housing additionally comprises a third part. The inlet member housing comprises an air inlet, preferably provided in and/or between two of the first part and/or the second part of the housing as well as an air outlet, preferably comprised in the second and/or third part of the housing. The inlet member further comprises an inlet or filter path extending from the air inlet to the air outlet. Preferably, the filter path constitutes part of the air path of a ventilation or breathing device and/or the air outlet of the filter is adapted to release filtered air into a ventilation or breathing device and its air path, respectively. The inlet member comprises an inlet filter for filtering the air flowing along the inlet path. The inlet member and the inlet filter, respectively, are preferably located at the low pressure side of a ventilation or breathing device. The air inlet allows ambient air to enter the inlet member and the filter and is not limited to one individual opening. Rather, the air inlet may comprise a plurality of separate openings to the ambience such as slots and/or holes.

Preferably, the inlet member comprises, in addition to the air inlet, an additional or second inlet, e.g., for the provision of oxygen. Such second inlet is preferably provided in or by the second part of the inlet housing and is accessible from the outside via a corresponding opening or cut out provided in the first part of the inlet housing. According to a preferred embodiment, the second inlet is provided as a separate part, connectable to one of the inlet housing parts, preferably the second inlet housing part, which separate part preferably extends to the second outlet to be described in more detail below.

The filter element is preferably arranged inside the inlet housing and more preferred between the air inlet and the air outlet of the filter. Alternatively, the filter element may also constitute or cover the air inlet. The filter element extends along the whole cross section of the air inlet path such that all air flowing through the air inlet member flows through the filter element. Said filter element comprises a frame as well as a filter material connected to the frame. The filter frame is preferably partly overmoulded with a soft material, of e.g. about 70 Shore A, for improving handling and enhancing sealing of the filter frame in the inlet filter path. Preferably, the filter frame is provided with a sealing lip. The filter element and thus its frame and filter material, preferably generally extend in one or at least one plane. The filter frame is preferably biased. Preferably, it has a slight radius resulting in a tension when assembled in a substantially plane position, thereby improving the proper sealing of the filter element in the inlet flow path. Preferably, the filter element comprises a cut-out, recess or opening, particular for allowing the extension of the additional or second inlet or the corresponding second inlet path past the filter element, without the gas or oxygen provided via the second inlet having to flow through the filter.

The second or oxygen inlet path, which preferably has a channel like configuration, extends from the second or oxygen inlet, preferably forming part of the second part of the inlet housing or being a separate part attached thereto, along the filter element to the outlet provided in or at the second part of the housing. The oxygen inlet path is thus preferably part of the second part of the inlet housing. Preferably, the inlet path protrudes from the second part of the inlet housing and extends up to or through the first part of the inlet housing. Preferably, the first part of the inlet housing is provided with an opening or recess for allowing or facilitating accessibility of the oxygen inlet. The oxygen inlet is preferably provided with a connection means for connecting an oxygen supply.

Preferably, the second part of the inlet housing comprises at least one outlet, preferably at least a first outlet and a second outlet. The first outlet is in fluid connection with the first (air) inlet and thus the inlet air flow. The second outlet is in fluid communication with the second (e.g. oxygen) inlet and thus the oxygen flow. Preferably, the first and second outlets are coaxially arranged. Preferably, the second outlet has a circular cross section while the first outlet has a ring shaped cross-section or geometry. Preferably, with regard to the direction of the air and/or oxygen flow, the second or oxygen outlet is set back with regard to the first or air outlet. Preferably, the second outlet is located upstream of the first outlet seen in the direction of air/oxygen flow, preferably immediately, i.e., less than 5 mm, upstream.

The first and second outlet are preferably provided in the second part of the housing. The air outlet and the oxygen outlet, are preferably arranged such that an air flow through the air inlet and through the filter is mixed with the oxygen supplied through the second or oxygen inlet, preferably due to the arrangement of the air and oxygen outlets as referred to above.

The air outlet and, if provided, also the oxygen outlet preferably lead to or open into an inlet chamber provided by, behind, and/or in the second part of the housing. Such inlet chamber preferably constitutes an inlet muffling chamber and/or a fluid flow path and/or a mixing chamber for properly mixing the air flow with the oxygen flow. According to a preferred embodiment, such muffling chamber is defined and/or closed by a third inlet housing part.

The inlet member is of particular advantage and allows the filtering of the air as well as the mixture of air and oxygen close to the air inlet and at the low pressure side of a ventilation or breathing device. Therefore, the provision of specifically pressurized oxygen or an individual adaption of the oxygen pressure to the breathing pressure becomes obsolete. Both, air and oxygen, preferably in a mixed form, can thus be supplied to the patient at optimized therapy pressure. Preferably, the inlet member of the breathing device functions as a muffler thus decoupling and dampening the noise emitted from the breathing device and the blower towards the inlet side. Thus, the inlet member according to the present invention additionally exhibits advantageous sound dampening properties and particularly reduces the overall noise of a ventilation or breathing device.

The housing of the inlet member preferably comprises structural elements for connection and securing the inlet member to a or inside a breathing or ventilation device. According to a preferred embodiment, the first inlet housing part particularly serves the purpose of protecting the inlet filter or the filter element from damages, for dampening noise, for securing the filter, and/or for aligning the visible exterior design of the inlet member with the ventilation device housing and appearance of a ventilation device to which the inlet member is to be connected.

The inlet member particularly allows an easy and safe inlet member handling. In particular, the filter element can be easyly handled and replaced, e.g., by the patient, a nurse or a service team member and is easy to ship and store. The inlet member according to the present invention furthermore reduces and preferably avoids bypass flow and serves a pre-muffler/silencer while allowing an optimized pressure decoupling between the delivery pressure to the patient and the oxygen supplied pressure. The inlet filter preferably seals the air inlet path so that all incoming air is filtered. Preferably the inlet filter is a dust and/or pollen filter.

The invention additionally and alternatively relates to a modular ventilation or breathing device as referred to above and particularly for use with a blower, impeller, gasket, air path and/or inlet member according to the present invention.

The respiration or ventilation device according to the present invention is preferably of an advantageous modular structure and comprises a housing module, preferably provided with operator input and display means. Additionally, there is provided an electric module, preferably comprising a skeleton carrier for carrying, i.a., a control unit and further electronics required, and for providing structural support as well as for allowing defined positioning of the modules and parts of the ventilation device. The ventilation device further comprises an air path module comprising an air path housing, comprising an air path inlet and an air path outlet, in which a blower is located. Preferably, the air path is the air path according to the present invention, wherein the air path housing comprises two parts each of which is sealingly connected to one side of the gasket according to the present invention while the gasket and/or the air path housing carries a blower including a motor, preferably the blower according to the present invention.

Preferably, the air path module includes an inlet member, preferably the inlet member in accordance with the present invention and/or a patient connector.

The electric module is preferably further adapted to be connected to and support the housing of the ventilation device as well as to support and/or position the air path module. In addition, the skeleton carrier and/or the electric module is preferably adapted for and comprises means for allowing a proper alignment and positioning of the different parts and modules of the ventilation device such as the parts of the housing module and/or the air path element. The electric module preferably comprises the power supply, battery or accumulator pack, control unit and/or a display unit.

In particular, as has become clear from the above discussion of the gasket and the air path, the blower and its motor is/are simply plugged or laid into the air path housing without the need for any screws or additional fastening members. Rather, the necessary suspension elements are provided integrally with air path module and the housing module. All that needs to be provided are silicone cushions for dampening the blower and motor in the housing. In addition, the device is adapted such that the electric module is simply laid onto the air path element without the use of further screws or other additional fastening means.

Once the inlet member and/or a patient connector is connected to the air path element, such as by plugging one into the other, preferably via a plug-in connector and/or flow sensor connector, and the air path is laid into the lower part of the housing module, and the electric module is placed over it, the combined electric module, the air path module including the inlet member, which are connected to one another without the use of screws or additional separate fastening means, the upper part of the housing is placed over them. Then the, preferably two, parts of the housing module are screwed to one another, thereby simultaneously fixing and securing the position of the different modules (air path module, electric module and housing module).

This configuration particularly allows an easy and advantageous way of manufacturing of the ventilation device as well as of its assembly. A reduced number of parts can be provided which are individually manufactured, prepared and mounted. These modules can then be easily assembled to constitute the ventilation device according to the present invention. Preferably, only a reduced number of fastening means such as screws, needs to be applied since the modular design of the ventilation device allows advantageous simultaneous fastening of the different modules. The device of the present invention is therefore of particular advantage since it allows an easy and fast assembly as well as disassembly and thus an improved maintenance or repair. Individual components can be easily replaced. Particularly all components being in contact with air inhaled or exhaled by a patient can be easily replaced.

The modular ventilation device of the present invention is also of particular advantage from the point of cleanliness and/or security. In particular, the device according to the present invention allows a clear separation between air path, including eventual oxygen supply, and electronics and/or housing. No part of the device housing constitutes part of the flow path. Not part of the electric or electronics and thus no circuit board or electric part lies in the air path. Preferably, the only sensor to be provided in the air path is the flow sensor which is preferably located between inlet member and flow path housing. Thus, preferably no dust and/or lint is lead to the electronics together with the air flow. Preferably, the patient is not exposed to the danger of inhaling smoke of burning of electronic parts.

Another aspect of the invention relates to a method for supplying air at positive pressure to a patient for treatment including providing air to a blower of the invention, pressurizing said air and supplying the air at positive pressure to a patient. Preferably, said method is used for providing a therapy as discussed in the introductory part of the application, such as a Bi-PAP therapy. Another aspect of the invention relates to the use of one or more of the aspects of the invention in the application of such method or therapy. Another aspect of the invention relates to the assembly of a modular patient ventilation device according to the present invention.

The ventilation device of the present invention is of particular advantage, as becomes clear from the overall discussion of advantages and benefits of the different aspects of the invention. In particular, there is provided an effective and efficient ventilation device which allows the provision of an optimized, fast therapy at reduced power consumption. Thus, the device can suitably be used with a battery pack—instead of being dependent on the generally power supply.

Additional and/or alternative preferred aspects of the present invention relate to the following items:

1. A blower for providing a supply of air at positive pressure having a stationary portion and a rotating portion, an air inlet and an air outlet, wherein the air outlet is split into at least two, preferably parallel, channels.
2. Blower according to item 1, wherein the stationary portion is a housing, preferably having the shape of a volute, and preferably forming part of the flow channel.
3. Blower according to item 1 or 2, wherein the rotating portion is an impeller.
4. Blower according to any one of the preceding items, wherein the rotating portion is coupled to a drive means, preferably an electric motor.
5. Blower according to any one of the preceding items, wherein the air inlet is generally axially arranged with regard to the axis of rotation of the rotating portion.
6. Blower according to any one of the preceding items, wherein the air outlet is tangentially arranged with regard to the axis of rotation of the rotating portion.
7. Blower according to any one of the preceding items, wherein the air outlet is of substantially radial cross sectional shape and/or is preferably split such that each of the two channels has a semi-circular cross-section.
8. Blower according to any one of the preceding items, wherein the air outlet directs the air flow generally tangentially out of the volute.
9. Blower according to any one of the preceding items, wherein the air outlet has at least a or a first portion being arranged substantially tangentially with regard to a radius around the axis of rotation of the rotating means.
10. Blower according to any one of the preceding items, wherein the air outlet has at least a or a second portion extending generally parallel to the axis of the air inlet.
11. Blower according to any one of the preceding items, wherein the split of the air outlet is achieved by means of at least one blade dividing the outlet into at least two, preferably parallel, channels.
12. Blower according to any one of the preceding items, wherein the blade forms part of the stationary portion and extends parallel to the direction of the air flow through the outlet and/or to the longitudinal axis of the air outlet.
13. Blower according to any one of the preceding items, wherein the blade extends in a plane defined by two axes, one being generally parallel and one being generally perpendicular to the axis of the stationary portion and/or of the axis of rotation of the rotating portion.
14. Blower according to any one of the preceding items, wherein the blower is a radial blower.
15. Blower according to any one of the preceding items, wherein the outlet channel and/or the channels achieved by the split of said outlet channel and/or the blade include a turn of the flow path of about 70° to 110°, preferably of about 90°.
16. Blower according to any one of the preceding items, wherein the blade is L-shaped
17. Blower according to any one of the preceding items, wherein the blade is formed integral with at least a part of the stationary portion, preferably of the blower housing or preferably of the volute
18. Blower according to any one of the preceding items, wherein the outlet channel and/or the blade is arranged and located such that it extends from the volute and/or in or into the outlet channel from a starting point lying on a tangent to a radius around the axis of rotation of the rotating part of the blower
19. Blower according to any one of the preceding items, wherein the outlet channel and/or the blade is arranged and located such that it extends from the volute and/or in or into the outlet channel from a starting point lying on the inner radius of the volute or housing.

20. Blade for use with a, preferably radial, blower for providing a supply of air at positive pressure, particularly according to any one of items 1 to 19, the blade being adapted to fit into an air outlet of the blower and to split the outlet into at least two, preferably parallel channels.

21. Impeller for use in a blower for providing a supply of air at positive pressure, particularly a blower according to any one of items 1 to 19, the impeller having an intertia of less than about 3.2 g cm$^2$, preferably of about 2.5 g cm$^2$.

22. Impeller according to item 21, wherein the moment of inertia lies in a range between about 1.2 and 3.2 g cm$^2$ and preferably between about 1.2 and 2.5 g cm$^2$ and preferably is about 2.2 g cm$^2$.

23. Impeller for use in a blower for providing a supply of air at positive pressure, particularly a blower according to any one of items 1 to 19, and particularly an impeller according to item 21 or 22, the impeller comprising a plurality of vanes extending from a shroud, wherein the shroud has a substantially wavy shaped outer circumference.

24. Impeller according to item 23, wherein the wavy shaped outer diameter extends between a minimum diameter Dmin and a maximum diameter Dmax, wherein the minimum diameter Dmin is in the range of about 24 to 32 mm, preferably about 28 mm, and wherein the maximum diameter Dmax is in the range of about 38 to 46 mm, preferably about 42 mm, and/or wherein the difference between the minimum and maximum diameter is about 4 to 22 mm, preferably about 10 to 18 mm.

25. Impeller according to item 23 or 24, wherein the maximum outer diameter is reached in a vicinity of the outer tips of the vanes and/or wherein the minimum outer diameter is reached between two adjacent vanes, preferably between each pair of adjacent vanes.

26. Impeller according to any one of items 23, 24 or 25, wherein the vanes have a portion with constant height and a portion of varying height 27. Impeller according to any one of items 23 to 26, wherein the vanes have a substantially uniform height from their starting point at their inner diameter until a first intermediate diameter; and a decreasing height from said first intermediate diameter towards their end at their outer diameter, the first intermediate diameter lying between the inner and outer diameters.

28. Impeller according to any one of items 23 to 27, wherein the blades are substantially straight from their starting point at their inner diameter until a second intermediate diameter; and are curved from said second intermediate diameter towards their end at their outer diameter, the second intermediate diameter lying between the inner and outer diameters.

29. Impeller according to any one of items 23 to 28, wherein a second intermediate diameter of the vanes preferably lies between a first intermediate diameter and the outer diameter.

30. Impeller according to any one of items 23 to 29, wherein the vanes are curved, the curvature preferably being negative, i.e., away from the direction of rotation.

31. Gasket for use in a breathing or ventilation device for providing a supply of air at positive pressure and for sealingly separating different areas of a flow path, preferably high pressure areas of a ventilation and breathing device from low or ambient pressure areas, the gasket comprising a core of a comparatively hard material and an outer layer being of a comparatively soft material as compared to the core.

32. Gasket according to item 31, wherein the core is made of aluminium and/or wherein the outer layer is made of silicone, said outer layer covering substantially the entire gasket.

33. Gasket according to any one of items 31 to 32, wherein the core and/or the outer layer is/are provided with one or more structural elements, particularly for allowing sealing contact, positioning, suspension and/or dampening of a blower and/or a housing defining an air path.

34. Gasket according to any one of items 31 to 33, wherein the gasket is of substantially planar shape.

35. Gasket according to any one of items 31 to 34, wherein the gasket has two sides, a first side for sealingly contacting and closing a first part of a housing and a second side for sealingly contacting and closing a second part of a housing thereby defining different areas or compartments such as high pressure areas and low pressure areas.

36. Gasket according to any one of items 31 to 35, wherein the gasket comprises at least two and preferably at least three, also preferred three, openings or holes for allowing an air flow to be directed from one side of the gasket to its other side.

37. Gasket according to any one of items 31 to 36, wherein the gasket comprises openings or holes being provided with support structures, established by the outer layer.

38. Flow path for a breathing or ventilation device for providing a supply of air at positive pressure, the flow path comprising first flow path housing part having an air outlet and being in sealing contact with a first side of a gasket according to any one of items 31 to 37 and a second flow path housing part having an air inlet and being in sealing contact with a second side of said gasket.

39. The flow path according to item 38, further comprising a blower, preferably according to any one of items 1 to 19, being supported by said gasket and being located inside the first housing part.

40. The flow path according to any one of items 38 or 39, the first flow path housing having a generally cup like structure, preferably being separated into at least two chambers by a separation wall, wherein the gasket sealingly closes the cup like structure and preferably each of the at least two chambers and/or the second flow path housing having a generally cup like structure, preferably being separated into at least two chambers by a separation wall, wherein the gasket sealingly closes the cup like structure and preferably each of the at least two chambers.

41. The flow path according to any one of items 38 to 40, the blower and its motor being supported in the flow path on one end of the motor by means of the first flow path housing and on the fluid inlet and/or the fluid outlet of the blower by means of the gasket, preferably by support structures provided at the openings for allowing air to flow form one side of the gasket to the other side.

42. The flow path according to any one of items 38 to 41, wherein the flow path is arranged such that breathable gas flowing along the flow path crosses the gasket at least twice and preferably three times, preferably by flowing through at least two and preferably three openings or holes provided in the gasket.

43. Self sealing cable, particularly for use with a blower, impeller, gasket or air path according to any one of items 1 to 42, the cable comprising a plurality of metal wires, the cables being provided with one silicone coating only.

44. Cable according to item 43, the wires being stranded wires or litz wires.

45. Cable according to item 43 or 44, comprising at least three, preferably five or more wires.

46. Cable according to any one of items 43 to 45, the silicone coating serving as a coating for each individual wire, as positioning means for each wire vis-à-vis its neighbouring wires, and as self sealing skin allowing the cable to be sealingly clamped between two components, preferably without the need for additional sealing material.
47. Cable according to any one of items 43 to 46, wherein the silicone coating has a thickness of at least 0.5 mm, preferably of at least 0.6 mm and preferably of at least about 0.7 mm, measured along the shortest distance from the outer surface of the cable to one of the wires.
48. Inlet member for a ventilation or breathing device, comprising a first inlet for receiving a first fluid flow, preferably an ambient air flow, and a second inlet for receiving a second fluid flow, preferably an oxygen flow, the inlet member defining a first and second fluid flow path and comprising a first and second outlet, respectively, the first outlet being of a ring like shape, the second outlet being arranged coaxially to the first inlet and/or being surrounded by the generally ring shaped first outlet.
49. Inlet member according to item 48, comprising a housing having at least one inlet housing part being provided with the first fluid flow path outlet and the second fluid flow path outlet.
50. Inlet member according to item 48 or 58, comprising a filter element extending over the whole cross section of the first fluid flow path.
51. Inlet member according to item 48, 49 or 50, having a/the filter element comprising a frame and a filter material, which has a generally planar extension and generally extends in at least one plane wherein the filter frame preferably defines and surrounds the at least one a plane in which the filter material extends.
52. Inlet member according to any one of items 50 to 51, wherein the filter frame is at least partly overmoulded with a material being softer than the material of the filter frame.
53. Inlet member according to any one of items 50 to 52, wherein the filter frame is provided with handling members and/or a sealing structure such as a sealing lip, preferably made of a soft material according to item 53.
54. Inlet member according to any one of items 50 to 53, wherein the filter frame is biased and preferably has a slight radius resulting in a tension when assembled in a substantially plane position which supports proper sealing of the filter element in the inlet flow path.
55. Inlet member according to any one of item 48 to 54, comprising an inlet housing comprising at least a first part and a second part and preferably a third part, wherein the inlet member housing comprises an air inlet, preferably provided in and/or between two of the first part and/or the second part of the housing as well as an air outlet, preferably comprised in the second and/or third part of the housing.
56. Inlet member according to any one of item 48 to 55, wherein the second inlet and the associated second fluid flow path is provided in or by the second part of the inlet housing and is accessible from the outside via a corresponding opening or cut out provided in the first part of the inlet housing.
57. Inlet member according to any one of item 48 to 55, wherein the second inlet and the associated second fluid flow path is provided as a separate part, connectable to one of the inlet housing parts, preferably the second inlet housing part, which separate part preferably extends to and is in fluid connection with the second outlet.
58. Inlet member according to any one of item 48 to 57, having at least one inlet housing part being defining at least a second inlet chamber forming part of a first and second inlet flow channel, the second inlet chamber being arranged downstream, seen in direction of the fluid flow, of the first and second outlets and providing a combined fluid flow path for the fluid flow through the first and the fluid flow through the second opening.
59. Inlet member according to any one of items 48 to 58, having at least one inlet housing part being defining at least a second inlet chamber forming part of a first and second inlet flow channel, the second inlet chamber being covered by a third inlet housing part or lid comprising an outlet of the inlet member.
60. Inlet member according to any one of items 48 to 59, provided with at least one inlet chamber being filled with a muffling material, preferably silicone foam.
61. Inlet member according to any one of items 48 to 59, constituting a first inlet flow path from first inlet 612 through filter 620 into a first inlet chamber 622 and through outlet 632 into a second inlet or muffling chamber 624 until outlet 612 and/or a second inlet flow path from second inlet 618 through channel 662 through second outlet 632 into second inlet or muffling chamber 624 until outlet 612, wherein the first and second inlet flow paths are joined as from the first 630 and second 632 outlet, respectively, and/or as from second inlet or muffling chamber 624.
62. Modular ventilation, comprising a housing module, an electric module and an air path module.
63. Modular ventilation device according to item 62, the air path module comprising the flow path according to any one of items 38 to 42, preferably including the inlet member of any one of items 48 to 61 connected thereto.
64. Modular ventilation device according to item 62 or 63, the electric member comprising a skeleton carrier providing structural support and positioning aid for the air path module and the housing module.
65. Modular ventilation device according to any one of items 62 to 64, the housing module comprising a first housing part and a second housing part, connected to one another by means of at least two, preferably at least three and more preferably five fastening screws, wherein the modules are arranged such that the fastening screws simultaneously fasten the first and second housing parts of the housing module, the electric module and/or the air path module with regard to one another.
66. Modular ventilation device according to any one of items 62 to 65, wherein the air path module is laid into the housing module without the need of further fixation and is fastened between one of the two parts of the housing and the electric member upon connecting the first and second housing part to one another.
67. Modular ventilation device according to any one of items 62 to 66, wherein the suspension elements required for positioning, supporting and/or dampening the air path module are provided integrally with air path module and/or the housing module, respectively.
68. Modular ventilation device according to any one of items 62 to 67, wherein the inlet member and/or a patient connector is connected to the air path element, such as by plugging one into the other, preferably via a plug-in connector and/or flow sensor connector.
69. Modular ventilation device according to any one of items 62 to 68, wherein the air path module is laid into the lower part of the housing module, and the electric module is placed over it, such that the combined electric module, the air path module including the inlet member, are connected to one another without the use of screws or additional separate fastening means.
70. Modular ventilation device according to any one of items 62 to 69, wherein the, preferably two, parts of the housing module are screwed to one another, thereby simultaneously fixing and securing the position of the different modules, such as the air path module, electric module and housing module.
71. Modular ventilation device according to any one of items 62 to 70, wherein no part of the device outer housing or housing module constitutes part of the flow path.
72. Modular ventilation device according to any one of items 62 to 71, wherein no part of the electric or electronics and thus no circuit board or electric part lies in the air path.
73. Modular ventilation device according to any one of items 62 to 72, wherein the only sensors to be provided in the air path are provided outside the flow path member, e.g. the flow sensor which is preferably located between inlet member and flow path member and the pressure sensor which is preferably located between the patient connector and the flow path member.
74. Modular ventilation device according to any one of items 62 to 73, further comprising a fan, preferably placed on the lower part of the housing module.
75. Modular ventilation device according to item 74, wherein the fan is at least partly located over a corresponding opening or air inlet provided in the lower part.
76. Modular ventilation device according to item 74 or 75, wherein the fan is supported, preferably clamped, in the device between the lower part and the electric module.
77. Modular ventilation device according to any one of items 74, 75 or 76, wherein the fan preferably comprises an elastic, preferably silicone, jacket or sheath extending around at least part of the, preferably rigid, fan housing.
78. Combination of a blower according to any one of items 1 to 19 with a blade according to item 20, with an impeller according to any one of items 21 to 30, with a gasket according to any one of items 31 to 37, with a flow path according to any one of items 38 to 42, with a cable according to any one of items 43 to 47, with an inlet member according to any one of items 48 to 61, and/or with a modular ventilation or breathing device according to any one of items 62 to 77.
79. Method for supplying air at positive pressure to a patient for treatment including providing air to a blower of the invention, pressurizing said air and supplying the air at positive pressure to a patient, preferably for applying a Bi-PAP therapy, using a blade according to item 20, and/or an impeller according to any one of items 21 to 30, and/or a gasket according to any one of items 31 to 37, and/or a flow path according to any one of items 38 to 42, and/or a cable according to any one of items 43 to 47, and (or an inlet member according to any one of items 48 to 61, and/or a modular ventilation or breathing device according to any one of items 62 to 77 and/or a combination according to item 78.
80. Use of one or more of the items of the invention, such as a blade according to item 20, an impeller according to any one of items 21 to 30, and/or a gasket according to any one of items 31 to 37, and/or a flow path according to any one of items 38 to 42, and/or a cable according to any one of items 43 to 47, and/or an inlet member according to any one of items 48 to 61, and/or a modular ventilation or breathing device according to any one of items 62 to 77 and/or a combination according to item 78 in the application of a method or therapy according to item 79.
81. Assembly of a modular patient ventilation device according to one of items 62 to 77.

Other aspects, features, and advantages of this invention will become apparent from the following detailed description when taken in conjunction with the accompanying drawings, which are a part of this disclosure and which illustrate, by way of example, principles of this invention.

The invention will further be discussed by exemplary reference to the preferred embodiments shown in the drawings. In the drawings, FIG. 1 shows a plan view of a generic prior art blower assembly;

FIGS. 17a-17b show three dimensional views of the first (FIG. 17a) and second (FIG. 17b) part of the flow path housing taken along line A-A (FIG. 17a) and B-B (FIG. 17b) of FIG. 16a;

FIG. 18 shows a three dimensional view of an air path according to the present invention;

FIGS. 20a-20d show an inlet member according to the present invention, wherein FIG. 20a shows a three dimensional side view, FIG. 20b a top view, FIG. 20c a bottom view and FIG. 20d a side view seen in an opposite direction of the view shown in FIGS. 20a-20d of said inlet member;

FIGS. 23a-23c show a three dimensional filter element according to the present invention (FIG. 23a) while FIGS. 23b and 23c show views of the filter element attached to the second inlet housing part;

Figure 3:
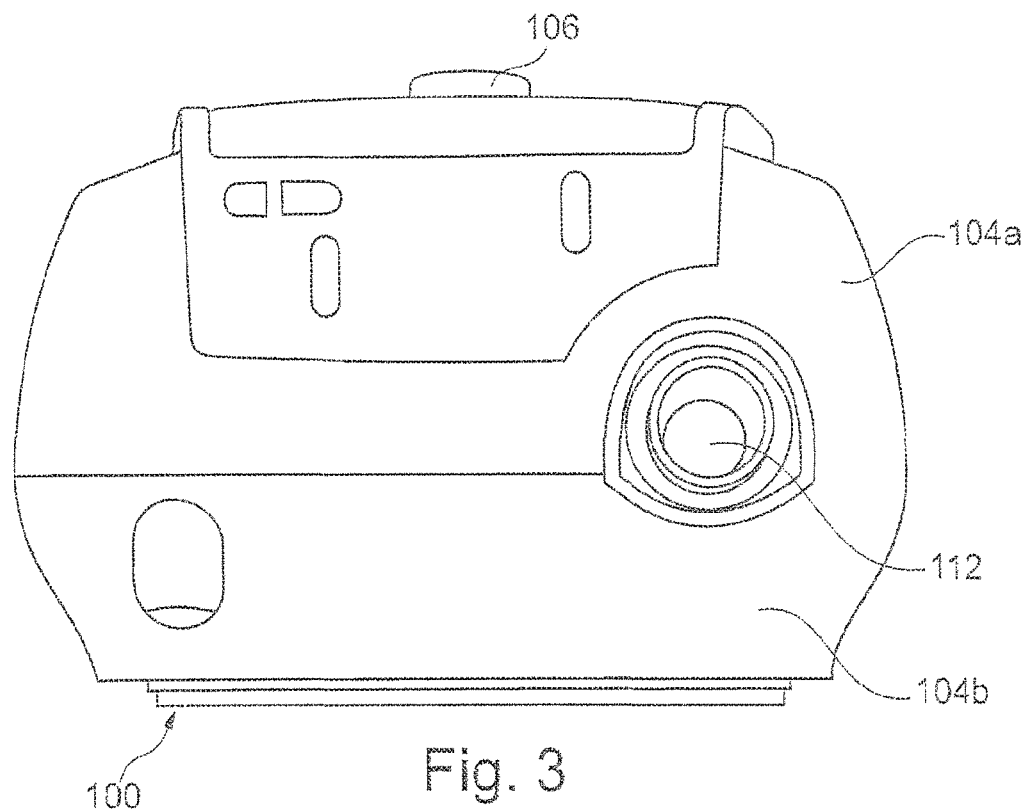
FIG. 3 shows a three dimensional front view of a ventilation device according to the present invention.
Figure 4:
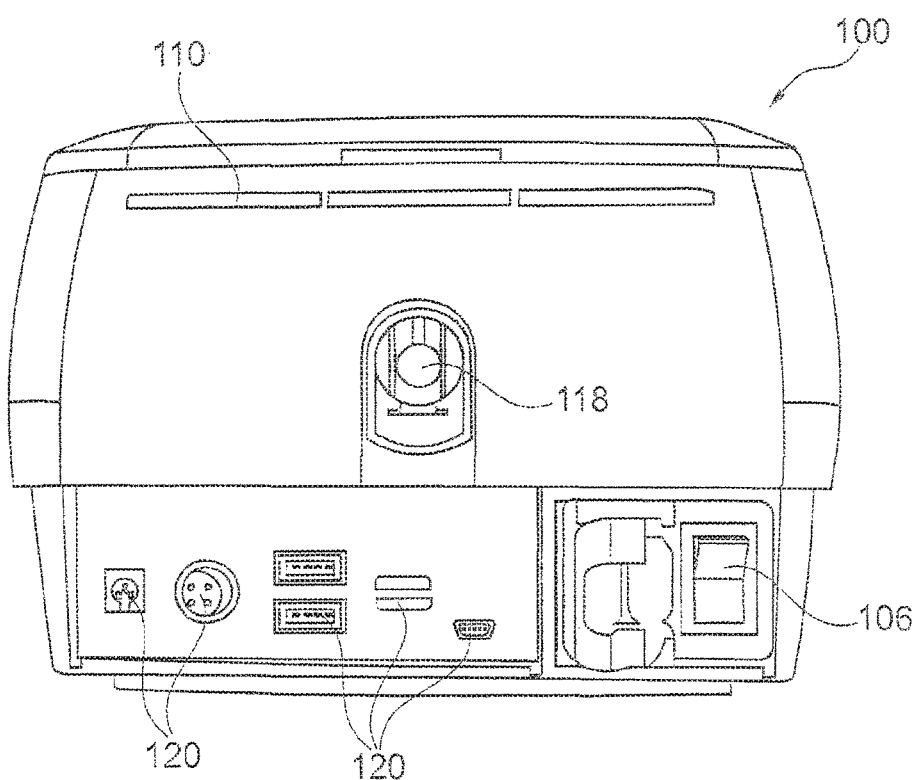
FIG. 4 shows a three dimensional back view of the ventilation device shown in FIG. 3
Figure 5:
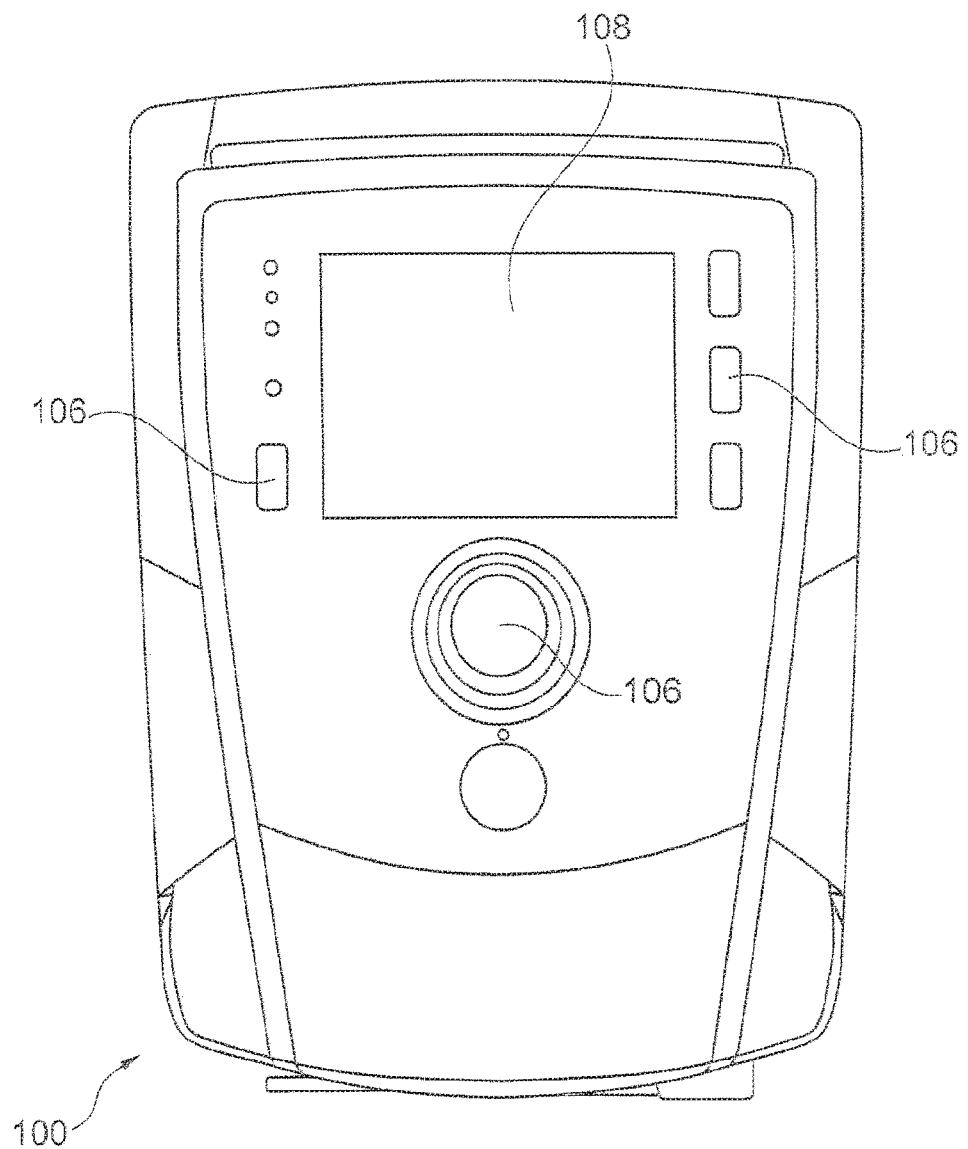
FIG. 5 shows a three dimensional top view of the ventilation device shown in FIGS. 3 and 4.

FIGS. 3, 4 and 5 show a three-dimensional front, back and top view of a ventilation device according to the present invention. The ventilation device 100 comprises a housing 104 provided with various input means 106 such as turn buttons, push buttons, and the like as well as a display or window unit 108 for displaying information, such as settings etc., to the user. The ventilation device further comprises one or more air inlet openings, generally referred to as inlet 110, and an air outlet 112, preferably provided with means of for connecting further components of a breathing or ventilation system such a respiratory tube or hose for delivering pressurized air to a patient and/or a humidifier.

The ventilation means 100 furthermore comprises a filter, preferably provided by an inlet member, provided behind the air inlet 110 for filtering ambient air entering the air inlet 110 of the ventilation device 100 and then being directed though the filter. The ventilation means preferably comprises an oxygen inlet 118 as well as means for connecting a supply of oxygen and for allowing, e.g., additional oxygen to enter the ventilation device 100. Such oxygen is, preferably in an inlet member and thus inside the ventilation device 100, added to the incoming air sucked in via the inlet 110 and through the filter and preferably mixed therewith. In a preferred embodiment, the filter, and preferably also the inlet member, is an integral part of ventilation device 100, preferably its air path.

Housing 104 of ventilation device 100 comprises, according to a preferred embodiment, an upper housing part 104a and the lower housing part 104b. The ventilation device 100 may further comprise additional ports or connection means 120 which allow connection of cables, such as power cables, USB cables, sensor cables and the like, i.e., constituting interfaces for connection of further devices for exchanging information and for providing power input. In addition, alternatively, a ventilation device 100 may comprise means for receiving a battery pack for providing the necessary power for mobile operation of the ventilation device.

Such device, as well as preferred individual components thereof, is discussed in the following, while it is understood that the individual components discussed below can equally be used alone or with similar or different devices.

Figure 10:
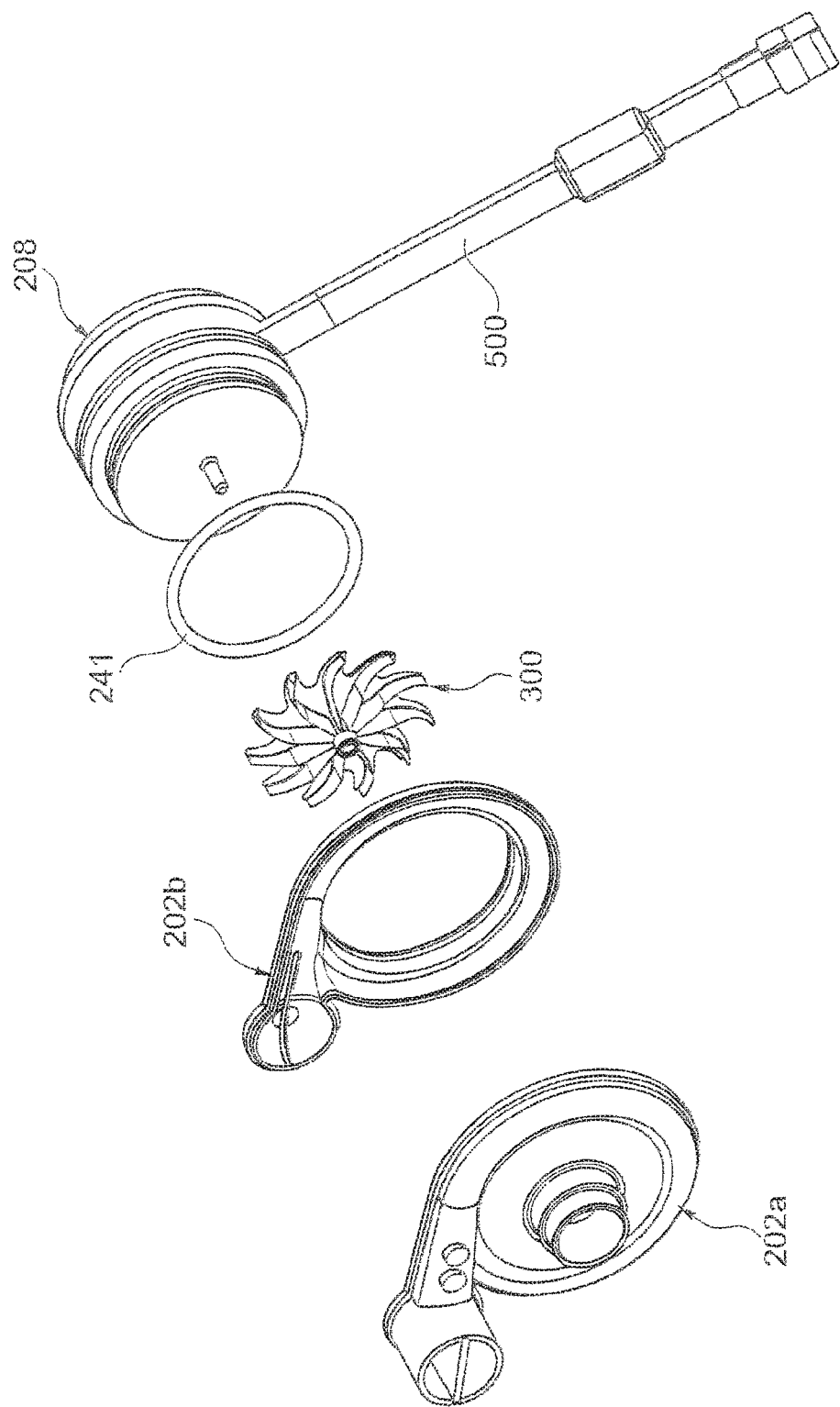
FIG. 10 shows an exploded three dimensional view of the blower shown in FIGS. 6 to 9.

FIGS. 6 to 9 show various three-dimensional views of a preferred blower according to the present invention or of parts and components thereof. FIG. 10 shows an exploded view of the blower shown in FIGS. 6 to 9.

Blower 200 comprises a housing 202 having the general shape of a volute. Preferably, the housing comprises two parts 202a, 202b, which are connected, e.g., mechanically and/or by means of ultrasonic welding. The housing 202 constitutes the stationary portion of the blower 200. The blower 200 further comprises a rotating portion comprising at least one impeller and a shaft to be driven by electric motor 208. In an embodiment, the electric motor 208 may be a brushless d.c. motor. In the illustrated embodiment, the blower has one stage while it is well understood that the blower may comprise two or more stages. The rotating portion of blower 200 is not shown in FIGS. 6 to 9. However, according to a preferred embodiment, impeller 300 according to the present invention constitutes the rotating portion of blower 200 according to the present invention.

Figure 2:
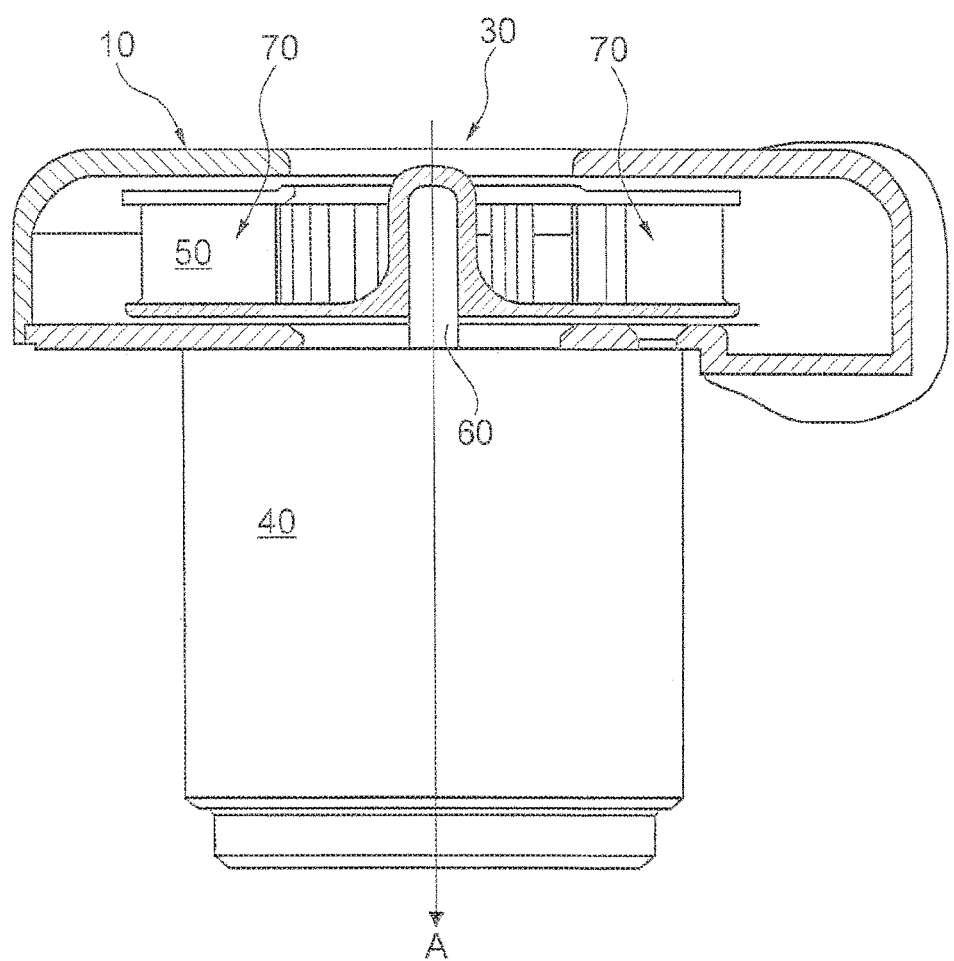
FIG. 2 shows an elevation view of the generic prior art blower assembly shown in FIG. 1.
Figure 6:
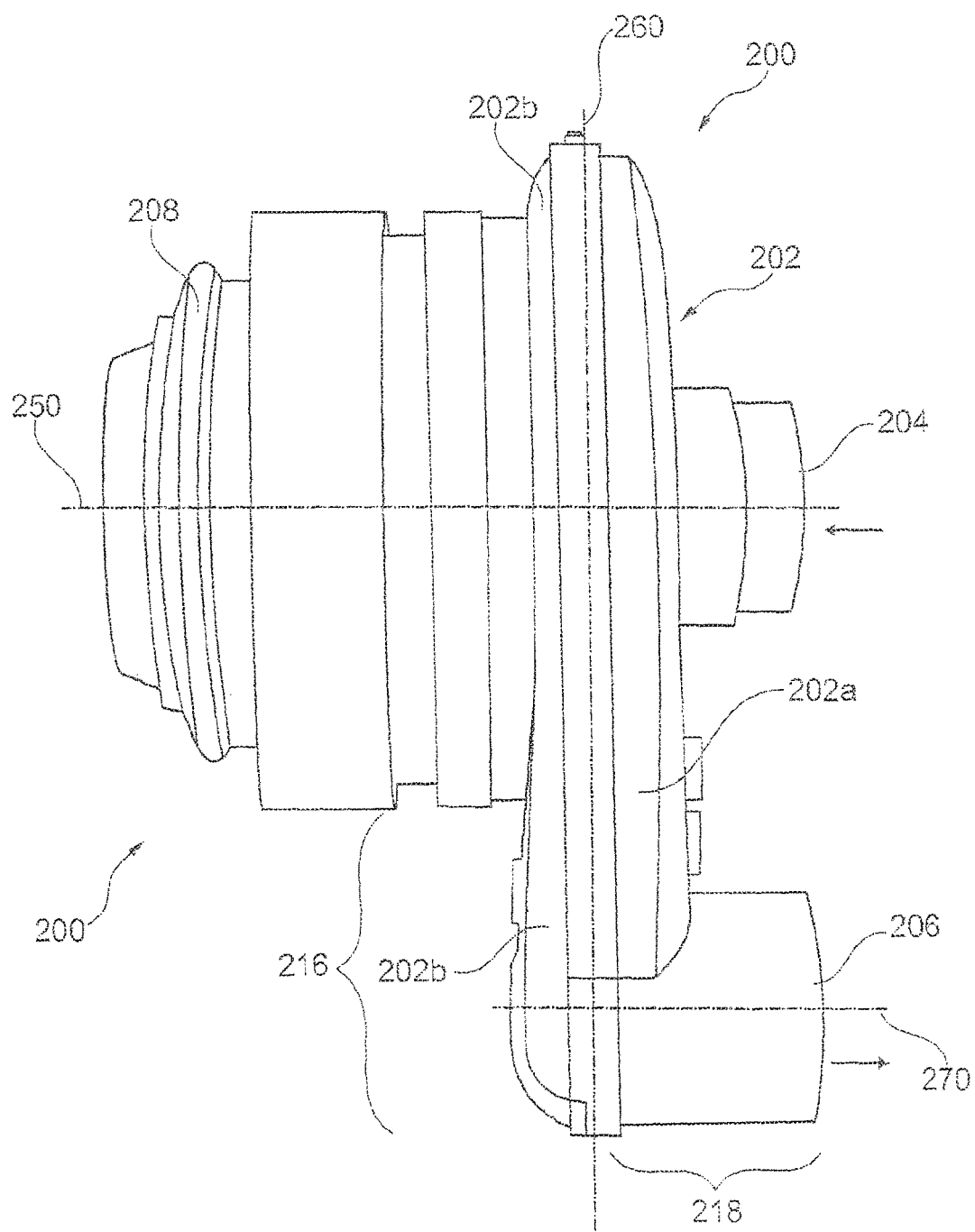
FIG. 6 shows a three dimensional top view of a preferred blower according to the present invention including a motor attached to the blower.
Figure 7:
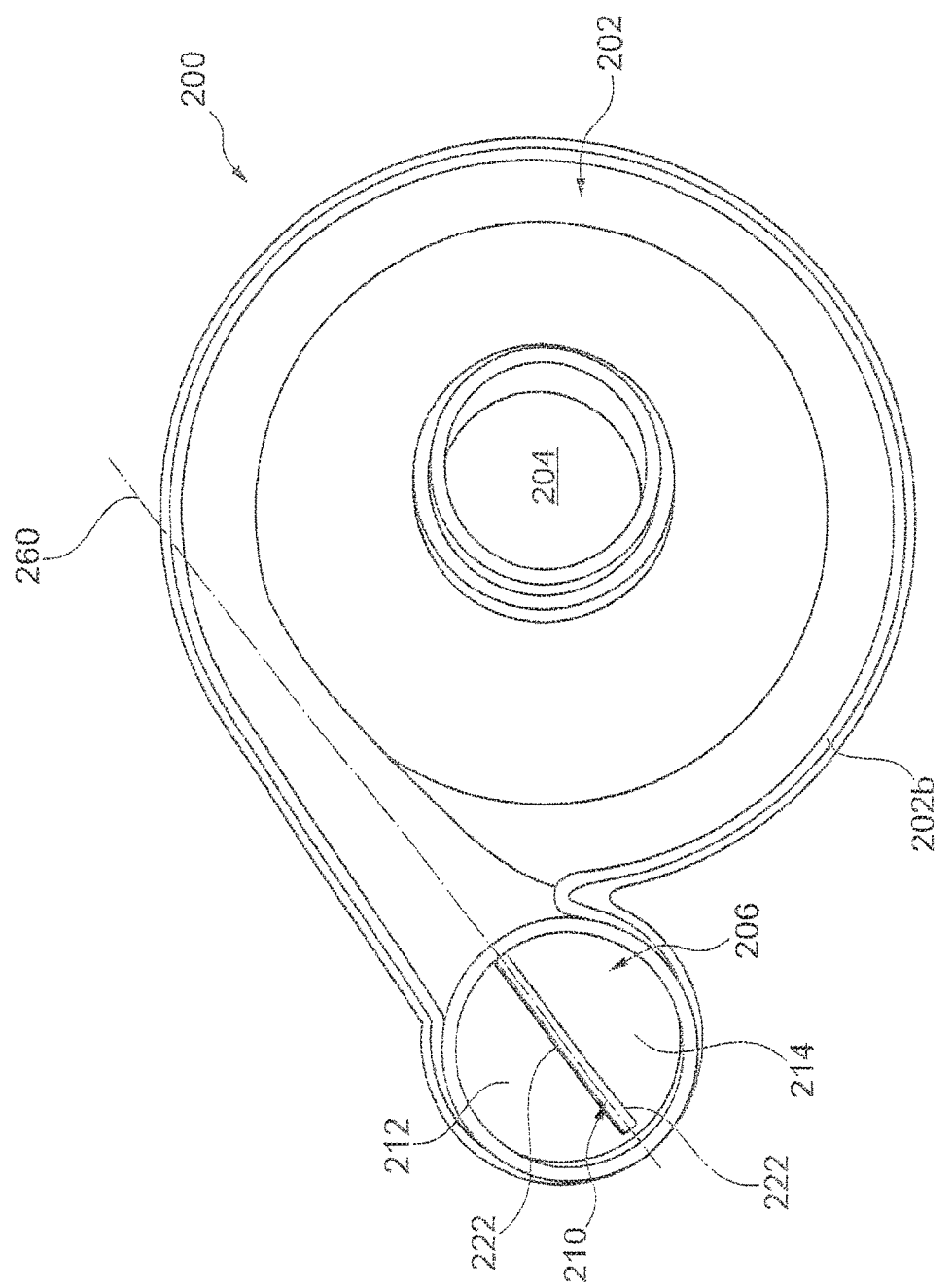
FIG. 7 shows a three dimensional side view of the blower according to FIG. 6 (motor not shown) facing the outlet channel of the blower.

The blower comprises an air inlet 204, preferably having a tubular shape, as well as an air outlet 206. Air inlet 204 is axially arranged, i.e., so that air enters the blower at the inlet 204 in a generally axial direction A (compare FIG. 2). The term axial used herein with regard to the blower relates to the longitudinal axis of the stationary portion, e.g., around which the volute winds, and/or around which rotating portion rotates. That axis is shown in FIG. 6 as axis 250. Arrows indicate the general direction of air flow.

Figure 1:
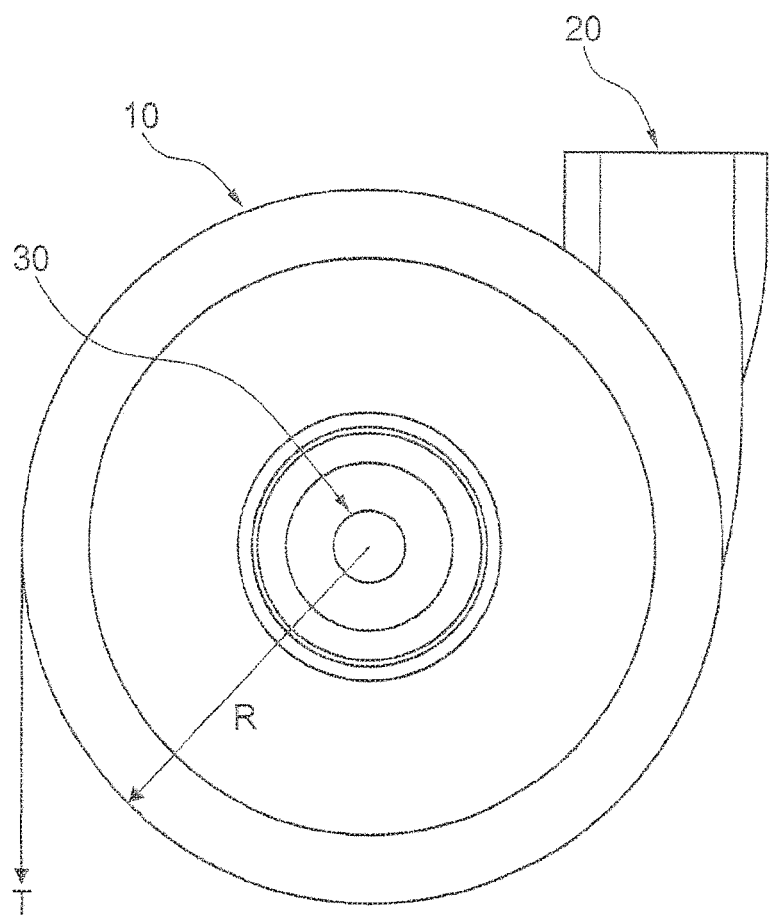

The rotation imparted by the impeller generally directs the air flow radially outwardly in a tangential direction T (compare FIG. 1) wherein the volute then constrains the air flow to spiral the volute. The air flow then exits as the blower or volute in a generally tangential direction T via the outlet 206.

Preferably, the volute geometry directs the tangential spiralling air flow in a slight axial direction prior to exiting the blower in a generally tangential direction.

In the shown embodiment, outlet 206 comprises a first axis 260 being generally tangentially arranged with regard to the blower and particularly its volute shape and/or rotation of impeller. Tangential axis 260 is preferably arranged essentially perpendicular to axial axis 250. Preferably, axis 250 and tangential axis 260 are distanced (shortest way) by less than 50 mm, and preferably by a length which generally corresponds to the radius of the blower, volute, and/or impeller. As indicated above, axis 260 preferably is a tangent to a radius 232 around the axis of rotation of the rotating part of the blower.

The outlet channel 206 of the blower 200 is, as shown, preferably L-shaped and comprises a first outlet portion or first outlet channel 216 extending along tangential axis 260 and a second outlet portion 218 extending in general perpendicular thereto and preferably parallel to axial axis 250. However, it will be appreciated that according to different embodiments, the outlet channel is not L-shaped but may be straight and/or curved.

The axis of the second portion 218 of the outlet is herein referred to as axis 270 and is preferably parallel to axial axis 250. However, it will be well understood that axis 270 of the second outlet portion 218 may have different directionalities. According to a preferred embodiment, axis 260 and 270 include an angle of preferably about 70° to 110° and preferably of about 90°.

Figure 8:
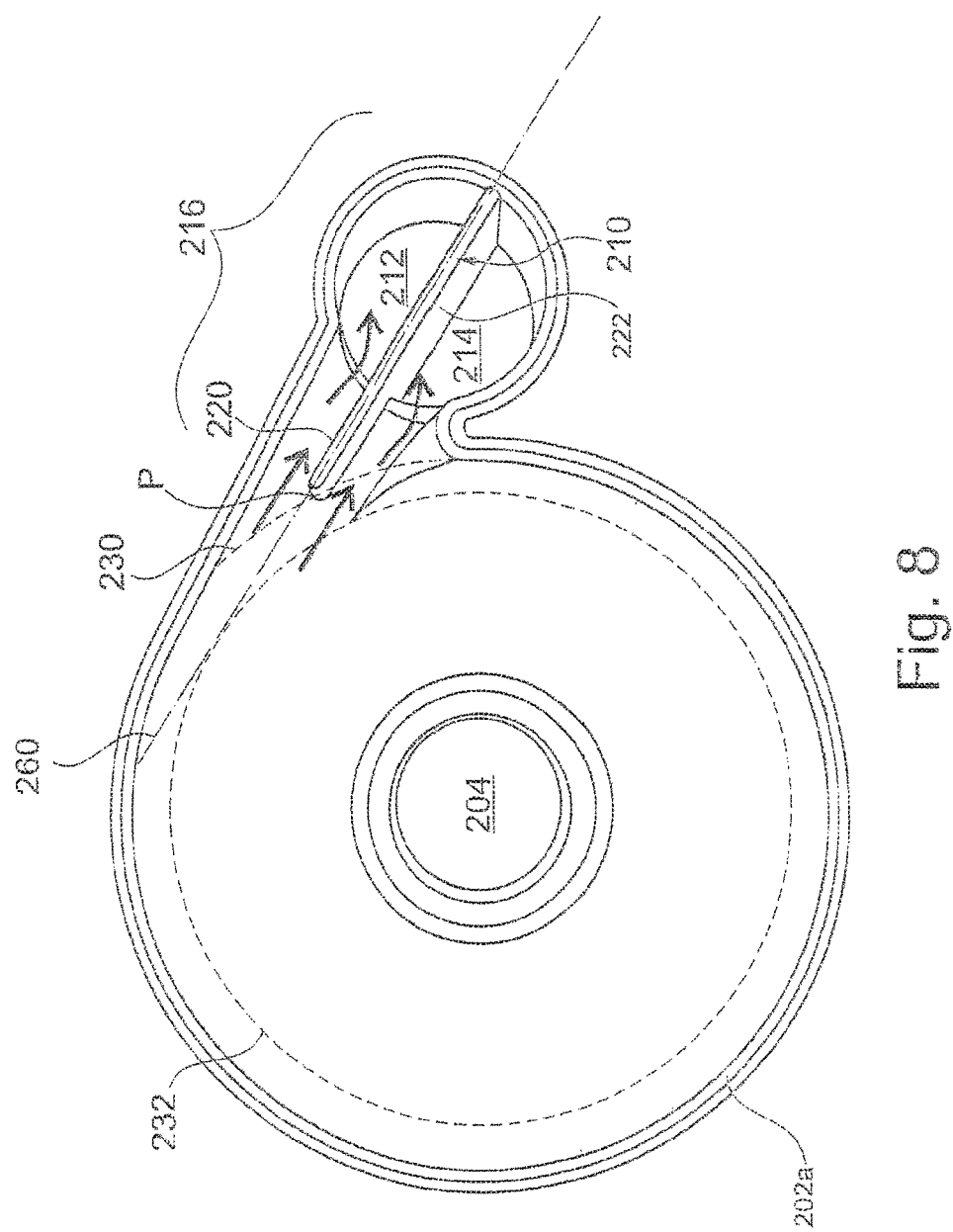
FIG. 8 shows a three dimensional view of a first part of the blower housing of the blower of FIG. 6 from the inside of the blower.
Figure 9:
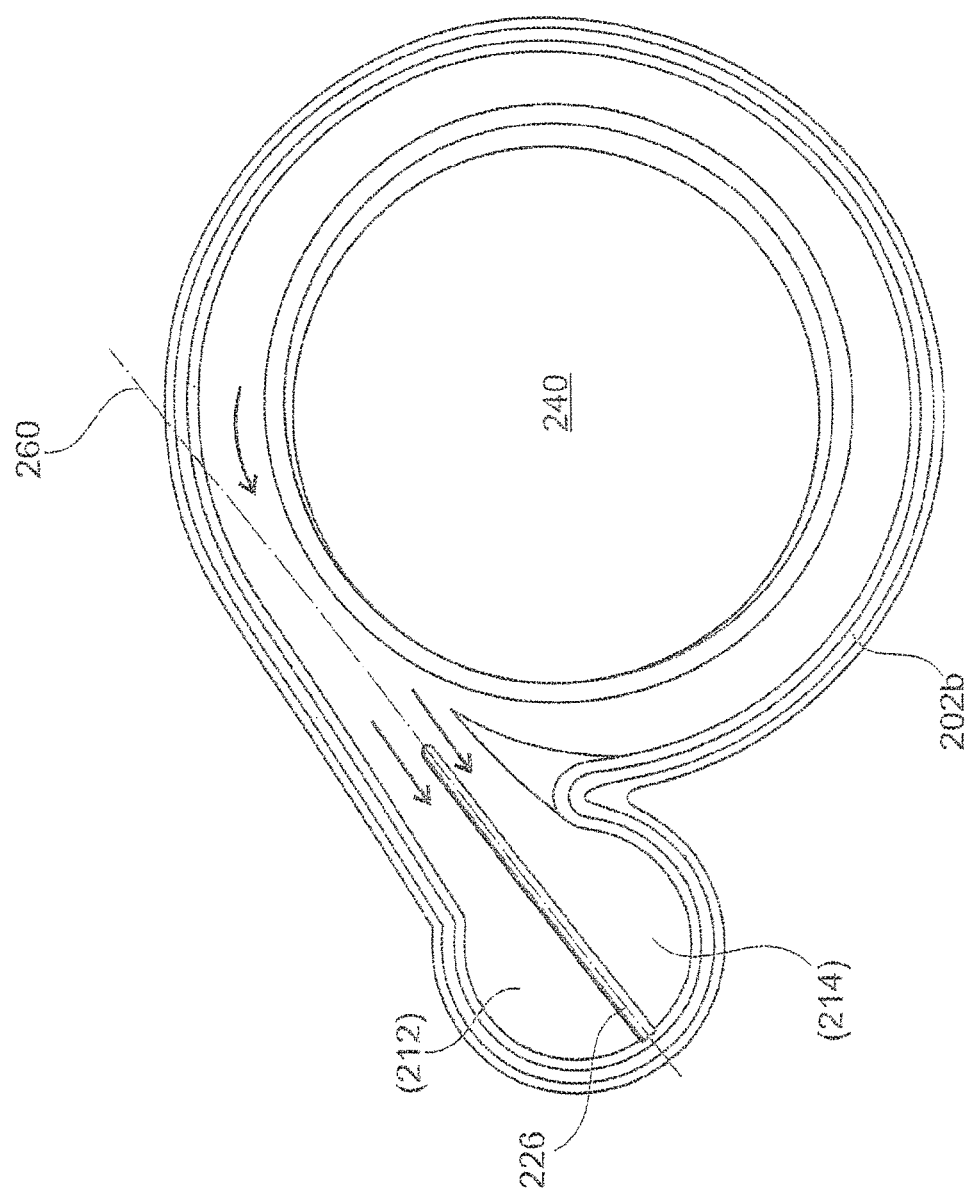
FIG. 9 shows a three dimensional view of a second part of the blower housing of the blower of FIG. 6 from the inside of the blower.

Preferably, the length of the first portion 216 of the outlet lies in the range from about 12 to 23 mm and preferably of about 18 mm along axis 260. According to a preferred point of reference, the length of the first portion 216 along axis 260 starts from the intersection of axis 260 with the outer radius of the blower, as is indicated in FIG. 8. In FIG. 8 the outer radius of the inside of blower 200 is indicated as 230, while the starting point of the first portion 216 is indicated as 'p'. First portion 216 preferably ends at the cross-section of the axis 260 of the first portion of the outlet 216 and the axis 270 of the second portion of the outlet 218.

Preferably, the blower is made of plastic material.

Preferably, the diameter of the outlet 206 is about 12 to 23 mm and preferably about 17 mm, the diameter of the inlet 204 is about 10 to 20 and preferably about 15 mm, the radius of the blower is about 57 to 67 and preferably about 62 mm; the shortest distance between axis 250 and 270 is about 37 to 47 mm and preferably about 42 mm. Preferably, the inlet 204 of the blower is of generally tubular shape and extends from the blower housing 202a. Inlet 204 preferably has a length of about 5 to 15 mm, preferably of about 10 mm. Preferably, inlet opening 204 and outlet opening 206 lie in one plane.

According to the present invention, the air outlet 206 is split into at least two channels 212, 214, which are preferably parallel. Preferably, the air outlet 206 is of substantially circular cross-sectional shape wherein the outlet is split such that each of the two channels 212, 214 has a semi-circular cross-section and particularly has a substantially identical cross section. The two channels preferably extend along the length of the outlet 206 and preferably along first portion 216 and/or second portion 218, preferably along both portions.

The present invention additionally and alternatively relates to a blade 210 as well as to a blower 200 provided with such blade 210. Blade 210 is preferably made of the same material as the blower and is preferably integrally formed with one of the two housing parts 202a or 202b of the blower housing or volute 202. Alternatively a portion of the blade 210 may be integrally formed in each of the two housing parts 202a and 202b. However, it will be well understood that blade 210 may also be provided separately and to then be connected to one or two of housing or volute parts 202a, 202b.

Blade 210 preferably extends substantially along the length of outlet 206, and preferably along the length of the first part 216 and the second part 218 of outlet 206. Blade 210 splits outlet 206 into two channels, namely a first channel 212 and a second channel 214 both of which individually extend along outlet 206 and first and second outlet portion 216, 218. Thus, blade 210 preferably comprises a first portion 220 and a second portion 222 corresponding to the first and second part 216, 218 of outlet 206.

Blade 210 preferably extends parallel to the direction of the air flow through the outlet and/or to the longitudinal axis 260 or axes 260, 270 of the air outlet 206. Blade 210 preferably extends in a plane defined by two axes, one being generally parallel and one being generally perpendicular to the axis of the volute.

Blade 210 is preferably located and arranged such that it extends in or into the outlet channel from a starting point 'p' as defined above. Preferably, blade 210 starts at said starting point 'p' or distanced from that starting point, preferably by about ±3 mm. As will be understood, if blade 210 extends too far into the volute, blade pass noise will be increased. If blade 210 starts too far from the volute, efficiency will be less.

Preferably, outlet 206 has a substantially circular cross-section while blade 210 splits outlet 206 along its diameter into the first and second channel 212, 214, which may be of equal shape and cross-sectional diameter, preferably of semi-circular cross-section.

Blade 210 is preferably substantially planar and extends along the axis of outlet flow 260 and/or 270 depending on the design of outlet 206. Therefore, in line with outlet 206, blade 210 comprises a first part 220 and a second part 222 which extend along longitudinal axes preferably being identical to axis 260, 270 of outlet 206. Preferably, blade 210 is substantially L-shaped.

According to a preferred embodiment, the blade has a thickness of about 0.5 to 1.5 mm, preferably about 0.8 to 1 mm, a width of about 10 to 20 mm, preferably 13 to 17 mm (depending on the size of the outlet channel), and a length of about 20 to 30 mm, preferably of about 23 to 27 mm. The length of the blade is preferably at least about 5 to 10 mm and it preferably extends along the entire length of the outlet channel. The thickness of the blade may vary, e.g. for allowing improved demoulding after being injection moulded.

In the shown embodiment, blade 210 is integrally formed with blade housing part 202a by means of injection moulding. Blade housing part 202b comprised a recess 226 for receiving blade 210. Blade housing part 202b preferably comprises an opening 240 (see FIG. 9) for receiving a rotating member, e.g. impeller 300. In use (compare FIG. 6) opening 240 is closed by motor 208.

According to another preferred embodiment, a blade generally corresponding to blade 210 is alternatively or also provided in a blower inlet 204 for splitting the inlet channel 204, which preferably extends along axial axis 250, into two, preferably parallel inlet channels.

FIG. 10 shows an exploded three dimensional view of blower 200 and motor 208. As will be readily understood blower housing parts 200a and 200b including blade 210 can be individually assembled wherein a rotating portion, e.g., impeller 300, is attached to drive axis of motor 208 and inserted into blower 200 via opening 240 provided in housing part 202b. Said opening 240 is preferably closed and sealed by the front face of motor 208, preferably using a sealing member 241. Motor 208 preferably comprises a cable 500 to be discussed below.

It will be understood that the measures and dimensions referred to above are preferred and can be varied by up scaling or downscaling the size of the blower.

Although the shown embodiment comprises two outlet channels it will be understood that the outlet channel, according to further advantageous embodiments, may comprise more than two outlet channels, e.g., three or four outlet channels. Such outlet channels can be achieved by providing more than one, e.g. two or three generally parallel blades or by providing two blades which are arranged generally vertically to one another. The same applies to a preferred blower inlet.

FIGS. 11a, 11b, 12a, and 12b show various views of a preferred impeller according to the present invention. Impeller 300 is preferably made of one-piece moulded, preferably injection moulded, plastic construction; although other suitable materials or manufacturing techniques could be employed. The impeller 300 comprises a plurality of vanes 302 extending from a disk-like shroud 304.

Shroud 304 is, vis-à-vis the vanes 302, located further distanced from the air inlet or downstream when seen in the direction of the air flow. Vanes 302 extend from shroud 304 into an upstream direction. Shroud 304 preferably incorporates a hub or bushing 306 that is adapted to receive a motor shaft 224. Shroud 304 is preferably of a disk-like shape having a maximum outer diameter of about 38 to 46 mm, preferably of about 42 mm. The radially outer tips of the vanes 302 preferably extend to the outer diameter of shroud 304. Preferably, the outer diameter of shroud 304 has a wavy or saw tooth shape and varies between a minimum outer diameter Dmin and a maximum outer diameter Dmax. Preferably, the maximum outer diameter Dmax is provided adjacent the radially outside tips of the vanes 302 while the minimum outer diameter Dmin is provided between each of two neighbouring vanes or tips of vanes 302. Preferably, the maximum outer diameter Dmax lies in the range of about 38 to 46 mm and preferably about 42 mm and/or the minimum outer diameter lies in the range of about 24 to 32 mm and preferably about 28 mm. Additionally and/or alternatively, the difference between the maximum and minimum outer diameter is in the range of about 4 to 22 mm and preferably or about 10 to 18 mm.

Additionally and/or alternatively, vanes 302 are curved in radial direction and are preferably tapered in height in their radially outer portions. The reduced height at the tips of the vanes preferably reduces turbulences and/or noise as well as the inertia of the impeller 300. Preferably, vanes 302 have an inlet height, i.e. at their inner diameter with regard to impeller's 300 axis where the air flow enters the impeller which uniformly extends along a first portion of the vanes 302 towards their (radially) outer end or tip. In a second portion of the vanes 302, which is preferably radially outwardly of the first portion, the height of the vanes 302 is reduced from a first height to a second height, being lower than the first height, wherein the second height constitutes the outlet height at the radially outer end of the vanes 302. Preferably, the first part extends from a starting point at the vanes' inner diameter close to the impeller's axis of rotation until a first intermediate diameter Dint1. The reduction in height starts from the first intermediate diameter towards their end at an outer diameter. The first intermediate diameter lies between the inner and outer diameters. Preferably, the maximum height of a blade is about 4 to 6 mm and is preferably about 5 mm and/or the minimum height of a blade, preferably close to its tip at its outer diameter, is about 1.5 to 3.5 mm, preferably about 2.8 mm. The geometry of the increase/decrease in height is preferably aligned with the geometry of the housing or stationary part and preferably corresponds thereto. Preferably, the difference between the inlet height and the outlet height, additionally or alternatively to the above preferred height dimensions, of the vanes 302 lies in the range of about 2.5 to 4.5 mm and more preferred of about 2 to 2.5 mm. The height reduction is preferably linear and/or curved.

Preferably, the blades are substantially straight from their starting point at their inner diameter close to the impeller's axis of rotation until a second intermediate diameter Dint2; and are curved from said second intermediate diameter Dint2 towards their end at the outer diameter, the second intermediate diameter lying between the inner and outer diameter. In the shown embodiment, the second intermediate diameter Dint2 lies between the first intermediate diameter Dint1 and the outer diameter Dmax. However, the second intermediate diameter Dint2 may also lay between the inner diameter and the first intermediate diameter Dint1 or equal the first intermediate diameter Dint1. The curvature can be either positive or negative while it is preferably that the curvature is negative, i.e., against direction of rotation. The positive orientation of the curvature achieves an advantageous relation of pressure over flow, thus allowing a continuous and fast reaction of the blower/impeller on changes in flow.

The first intermediate diameter Dint1 is preferably about 20 to 24 mm and preferably about 22 mm and/or the second intermediate diameter Dint2 is preferably about 21 to 25 mm and preferably about 22 to 24 mm.

Figure 11B:
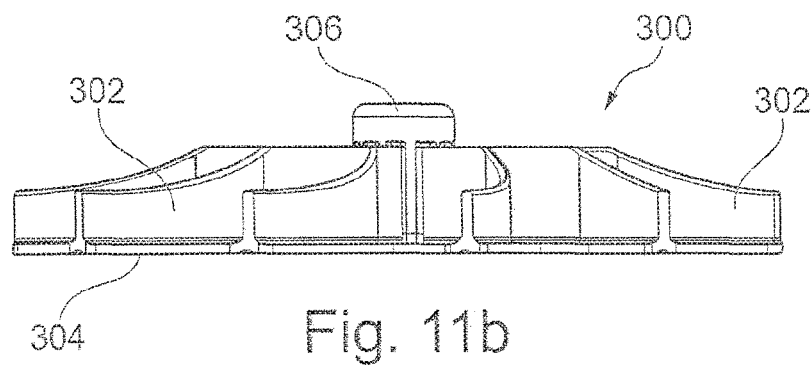
FIGS. 11a and 11b show a three dimensional top view (FIG. 11a), a side view (FIG. 11b), of a preferred impeller according to the present invention.
Figure 11A:
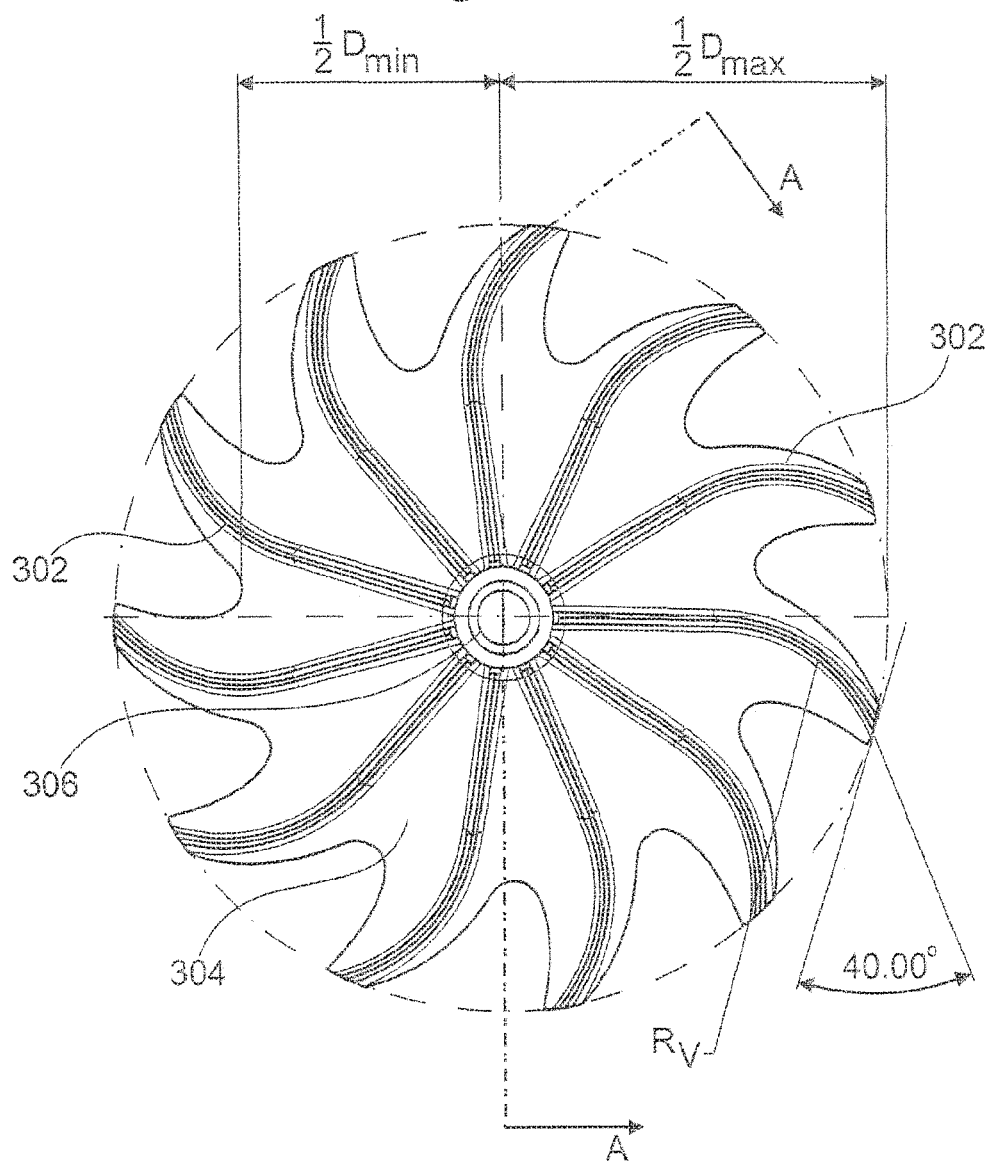
Figure 12B:
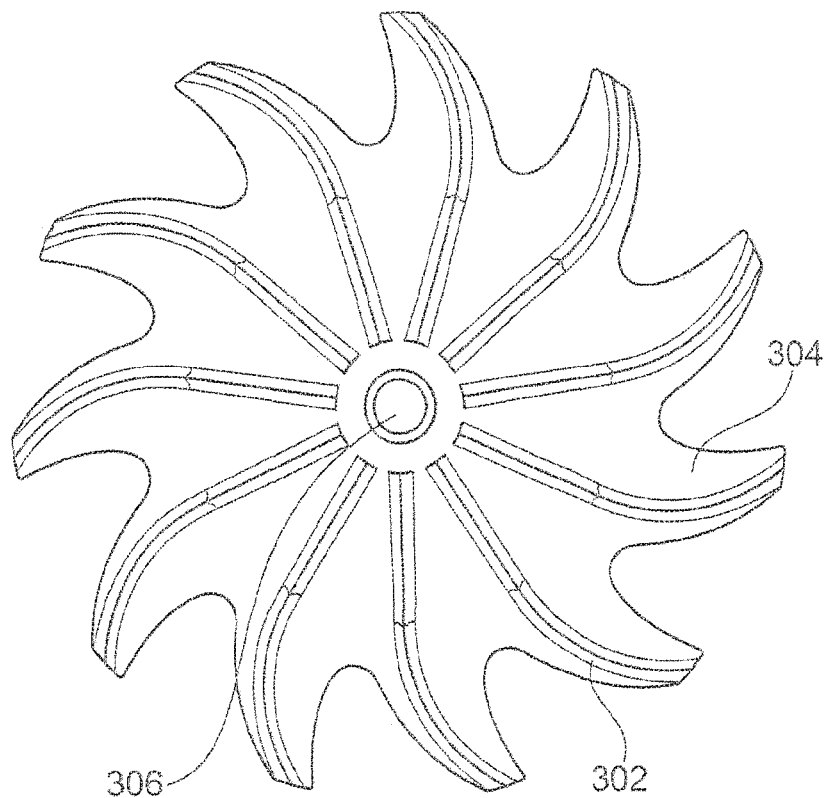
FIGS. 12a and 12b show a three dimensional partly cross sectional side view along line A-A of FIG. 11a (FIG. 12a) and a bottom view (FIG. 12b) of the impeller according to FIG. 11.
Figure 12A:
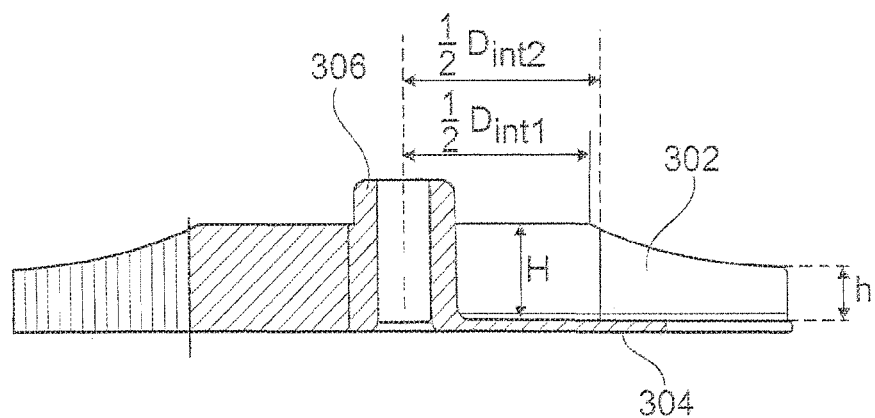

Preferably, the vanes 302 have an inclination with respect to an associated tangent at their tip of between 0° and 60°, e.g., about 40° (see FIG. 11*a*).

Preferably, impeller 300 has 4 to 100 blades 302, e.g., 11, while the number is preferably uneven.

The impeller according to the present invention preferably has an inertia of less than about 3.2 g cm$^2$, preferably less than about 2.5 g cm$^2$ and more preferred of about and/or less than 2.2 g cm$^2$. Preferably, the inertia lies in a range between about 1.2 g cm$^2$, preferably 1.7 g cm$^2$ and the above upper values.

The impeller according to the present invention is preferably made of plastic, preferably O$_2$ resistant plastic and/or preferably unfilled plastic material, such as a thermoplastic material.

The geometry and the design of the preferred impeller 300 according to the present invention particularly allows a significant noise reduction vis-à-vis impellors known in the art and additionally provides a comparatively low inertia. In addition, the effectiveness of impelling or pumping air is significantly reduced. It will be understood that the measures and dimensions referred to above are preferred and can be varied by up scaling or downscaling the size of the impeller. It is preferred that the impeller of this invention is used in combination with the blower of the invention.

Figure 13A:
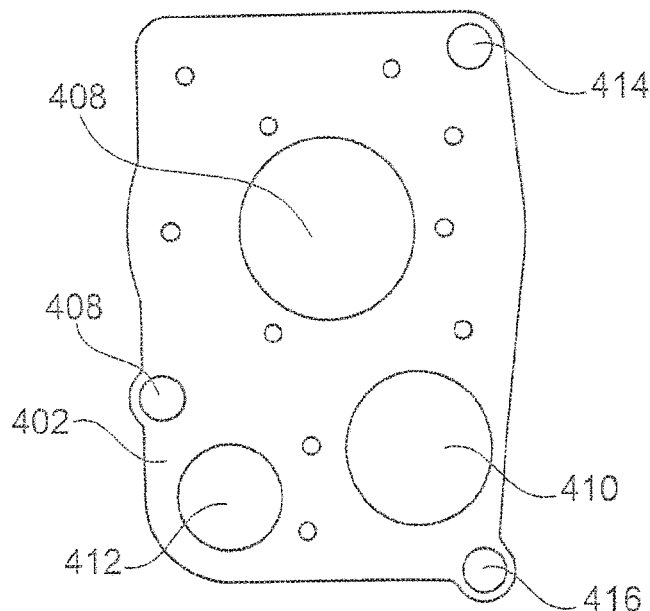
FIG. 13a-13c show a first (FIG. 13a) a second (FIG. 13b) and a third (FIG. 13c) three dimensional side view of a core of a gasket according to the present invention.
Figure 13B:
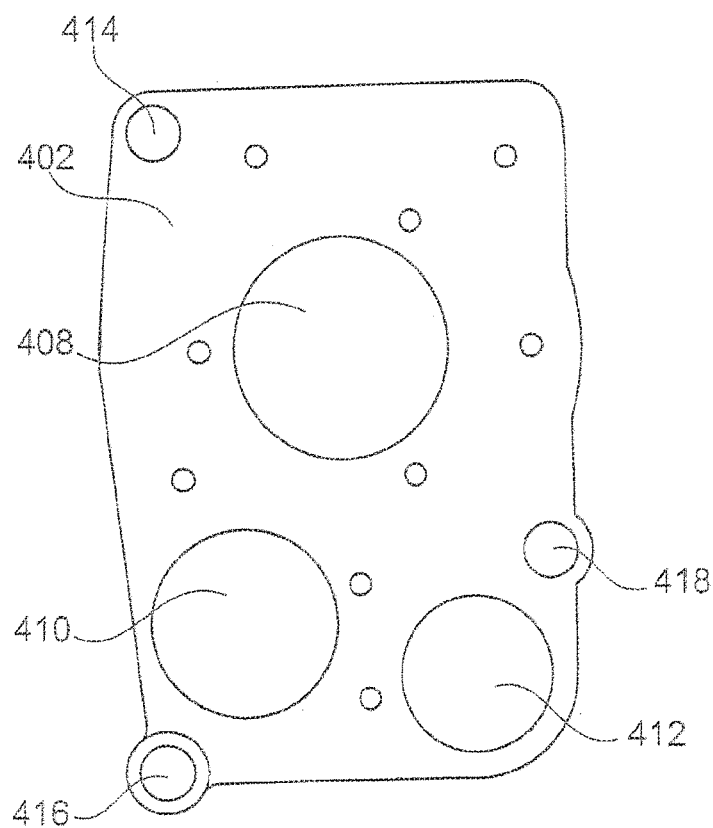
Figure 13C:
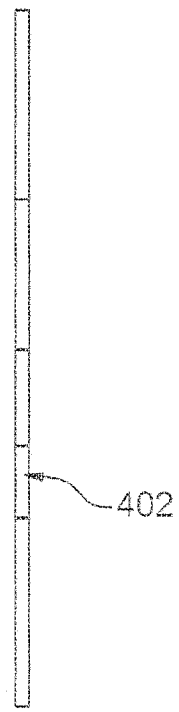

FIGS. 13*a*-13*c* show the core 402 of a gasket 400 according to the present invention. FIG. 13*a* shows a view on the gasket core 402 from a first side and FIG. 13*b* show a view of said gasket core from the opposite side. FIG. 13*c* shows a view of the core 502 of said gasket 500 from a third side (perpendicular to the views of FIGS. 13*a* and 13*b*).

Figure 14A:
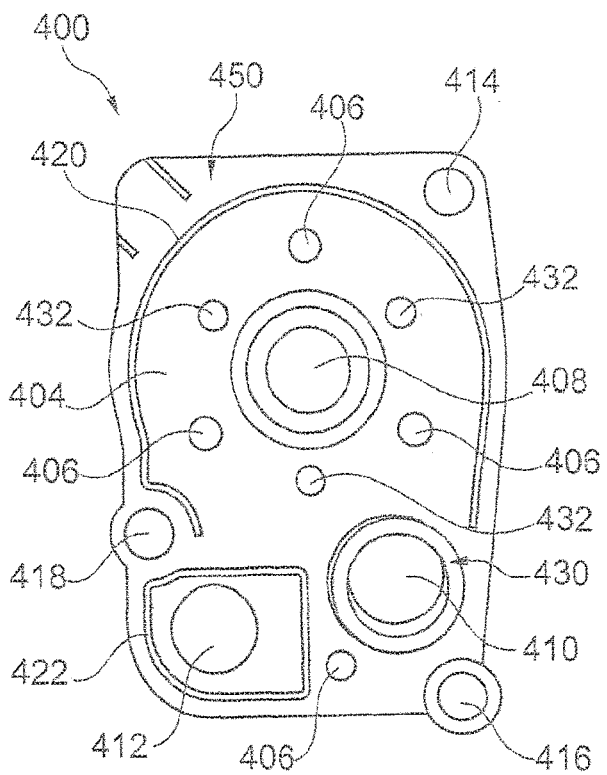
FIGS. 14a-14c show three dimensional side views (FIGS. 14a-14c) of a coated core corresponding to the views of the gasket core shown in FIGS. 13a-13c.
Figure 14C:
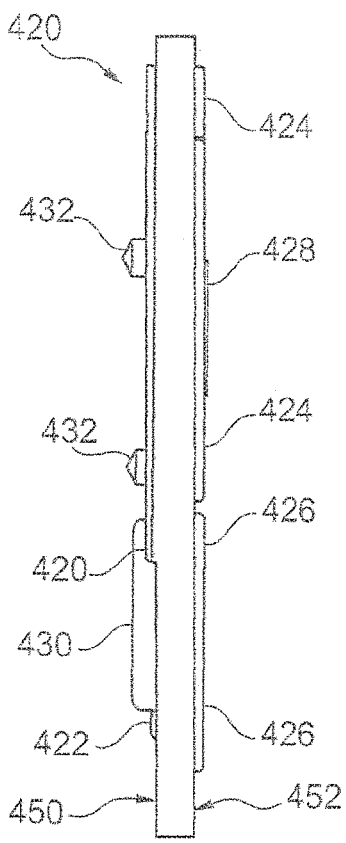
Figure 14B:
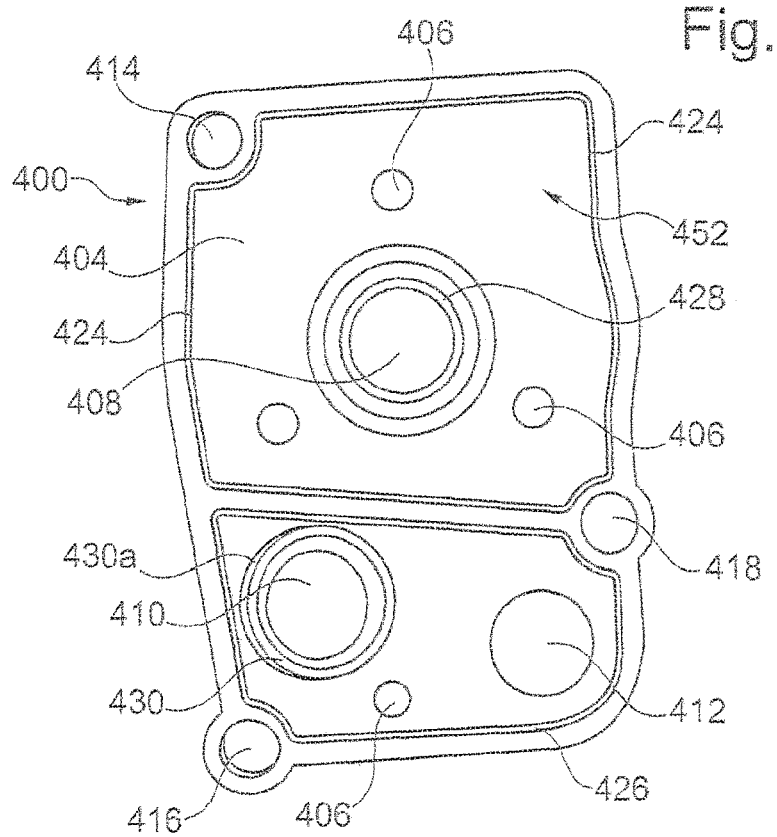

The core of the gasket is preferably made of a comparatively hard material, particularly when compared to an outer material of the gasket, and is preferably made of aluminium. Said core is provided with a plurality of structural elements for allowing air to flow through the gasket and/or for providing structural support, e.g., for a housing or a blower. Said gasket is provided with a skin or coating 404, preferably of elastic plastic material and preferably made of silicon. FIGS. 14*a*-14*c*, which are views of core 400 corresponding to the views shown in FIGS. 13*a*-13*c* with a silicon skin or coating 404 applied. According to a preferred embodiment, due to manufacturing reasons, certain areas of core 402 remain uncoated. These areas, which result from the support of the core 402 during the coating process are indicated as areas 406. It will be understood by the person skilled in the art that, depending on the coating or manufacturing process, different areas than those shown in FIG. 14 can remain uncoated. For example, areas 406 can be larger or smaller or there can be more or less or even none of such areas.

A gasket 400 comprises at least three holes or openings for defining an air path from a first side of gasket 400 to a second side of gasket 400 and/or visa-versa. In the shown embodiments, gasket 400 comprises a first hole 408 for allowing air to be sucked in from an air inlet at a low pressure area located on the second side of the gasket 400 into a blower located on the first side of the gasket. An opening or hole 410 is provided for establishing a passage of pressurized air supplied by a blower to flow from the first side 450 of the gasket (as shown in FIG. 14*a*) to a second side 452 of the gasket (shown in FIG. 14*b*). A third opening 412 is provided for allowing air to flow from a second side of the gasket (as shown in FIG. 14b) in a still pressurized state to the first side of the gasket (shown in FIG. 14a).

Preferably, gasket 400 contains further structural elements, such as recesses, holes or protrusions, for allowing proper alignment and/or connection of, e.g., a housing or parts of a housing with the gasket. In the shown embodiments, such a positioning and/or fastening means are realized as, e.g., holes 414, 416 and 418.

Preferably, gasket 400 is provided with additional structural elements for allowing proper positioning, sealing connection, dampening and/or supporting of parts attached to the basket or between the gasket and parts attached thereto. Such elements can be lips, rims, flanges, elevations, recesses or the like which can either be provided in the core 402 of the gasket and/or in the gasket's coating 404. In the shown embodiment, respective structural elements are provided as part of coating 404. For example, there are provided rims 420, 422, 424 and 426. According to a preferred embodiment these rims 420-426 allow proper alignment, additional support and/or improved sealing of elements contacting gasket 400. For example, rim 420 co-operates with a blower attached to the first side of gasket 400 while rims 422 and 424 and 426 are adapted to co-operate with channels or chambers of a housing or parts of a housing attached to the gasket 400. Here, co-operation includes mechanical and/or visual co-operation, the latter particularly allowing improved assembly.

In the shown example, there are further provided support structures 428 and 430 which are associated with the first and second holes, respectively. These structures 428, 430 are preferably adapted as structures defining a hole or opening being aligned with the first hole 408 and the second hole 410 as referred to above. In the following it will thus only be referred to the first and second hole 408, 410 for the ease of reference. Support structures 428 and 430 which can be also referred to as the first support structure 428 and the second support structure 430 are preferably substantially circular but may take other geometries. The opening 408, 410 provided by said first and second support structure 428, 430, respectively, is preferably defined by an inner circumference of said support structures 428, 430. Said inner circumference, which may be provided by a rim, is preferably elastically connected with gasket 400 and particularly with the core 402 of said gasket 400. Such elastic connection may be achieved, e.g., by a folded or bellow like structure, such as shown with regard to structure 428 and/or by providing a portion of a thickened and/or thinned cross-section, e.g., as shown with regard to structure 430. Here, structure 430 is provided, on the first side of gasket 400, with a thickened rim 430a which extends to the second side of gasket 400. On the second side of gasket 400, there may be provided an additional recess 430a.

In the shown preferred embodiment, support structures 428 and 430 provide a system for sealing connection and dampening of as well as for positioning a blower to be connected with the gasket 400, preferably a blower 200 according to the present invention. The inlet channel 204 of such blower then extends through first opening 408 while the outlet channel 206 extends through outlet 410. Gasket 400 is, on its first side 450 on which the blower is preferably located, preferably provided with additional positioning and support means 432 here adapted to be circular protrusions 432 protruding from the first side of coated core 400.

Figure 15A:
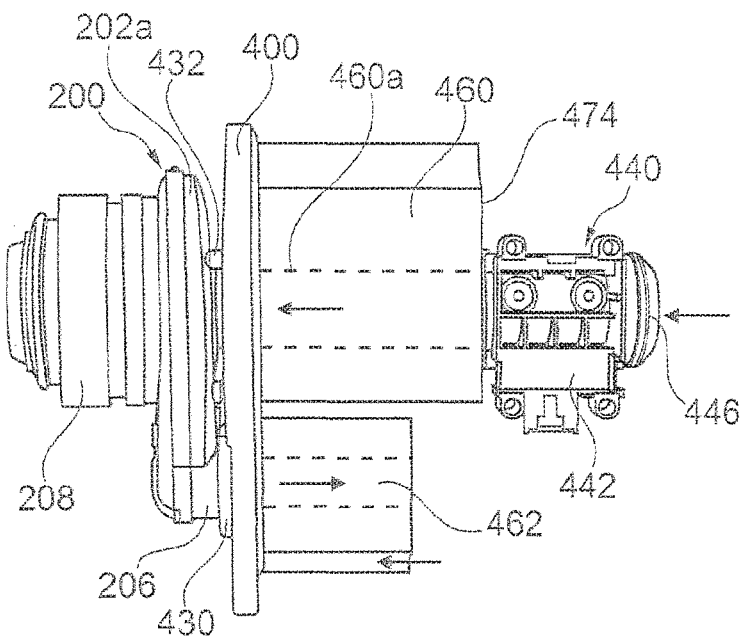
FIGS. 15a-15c show different three dimensional views (FIGS. 15a, 15b, 15c) of core 400 in combination with a blower, preferably a blower in accordance with the present invention, and with fluid flow part members.
Figure 15C:
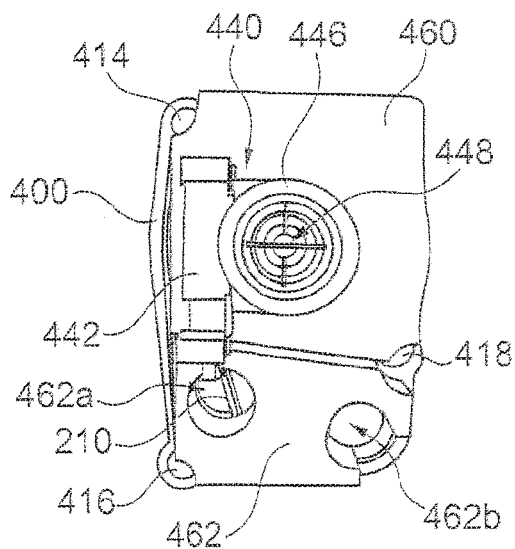
Figure 15B:
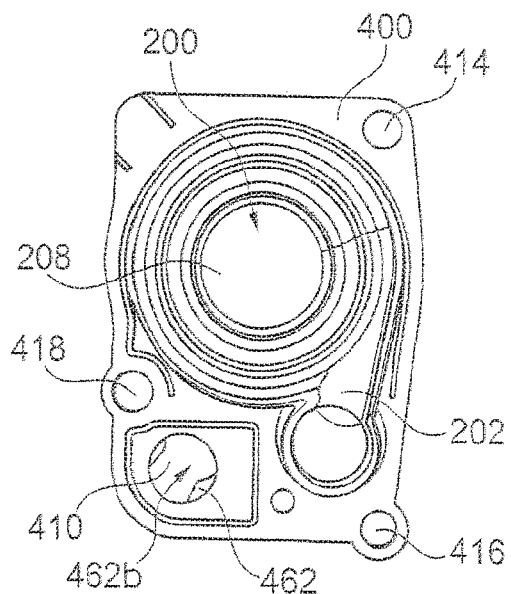

FIGS. 15a-15c show core 400 in combination with a blower 200 including motor 208, preferably a blower in accordance with the present invention, and with fluid flow path members 460 and 462. FIG. 15a shows a view generally corresponding to the one of FIG. 14c while the blower 200 is shown in a view corresponding to that of FIG. 6. As can be easily seen, blower 200 is attached to the first side 450 of gasket 400 with its inlet channel 204 extending through opening 408 and its outlet channel 206 extending through opening 410. As can also be seen, the blower 200 is supported by support member 430 and additionally rests on or contacts support members 432. Flow channel member 460 constitutes and defines a first flow channel 460a. Flow channel member 460 is located on a low pressure side of blower 200 and fills a low pressure chamber (to be discussed below) and constitutes a flow channel 460a. Flow channel member 460 is also referred to as low pressure flow channel member 460 and is preferably made of a foamed material, preferably a silicone foam and preferably of a closed-cell silicone foam. Flow channel member 462 defines a flow channel 462 located on a high pressure side of gasket 400 and preferably fills a high pressure chamber (to be discussed below). Preferably, high pressure flow channel member 462 defines a first flow channel 462a and a second flow channel 462b through which pressurized air flows in opposite directions. Flow channels 462a and 462b may be established as one channel making a, e.g., 180°, turn, or may be established as, e.g., two, individual flow channels being directed in opposite or different directions while the turn or connection between these channels is established by a flow directing means, e.g., part of a housing.

As can be taken from, e.g., FIGS. 15a and 15b, flow path 460a as preferably defined by flow channel member 460 extends from a connecting member 440 to through gasket 400 into blower 200. Connector 440 preferably comprises a sensor 442, preferably a flow sensor, provided on or attached to a dampening and connecting member 446. Connector 440 is preferably connected to housing 472 (see FIG. 16) to establish fluid connection with flow path 460a and is further adapted to be connected to inlet member 600 (see, e.g., FIG. 18) to establish fluid connection with the inlet flow path. Connecting member 446 is preferably made of elastic material and/or arranged to be connected to flow path housing 472 and/or inlet member 600 by means of a plug-in connection. Due to its elastic properties, connecting member 446 preferably also functions as a dampening member.

In the side view according to FIG. 15c (compare FIG. 16c) sensing means 448 of sensor 442 can be seen as well as flow channel parts 462a and 462b. Through flow channel part 462a outlet 206 and blade 210 of blower 200 are visible.

Figure 16A:
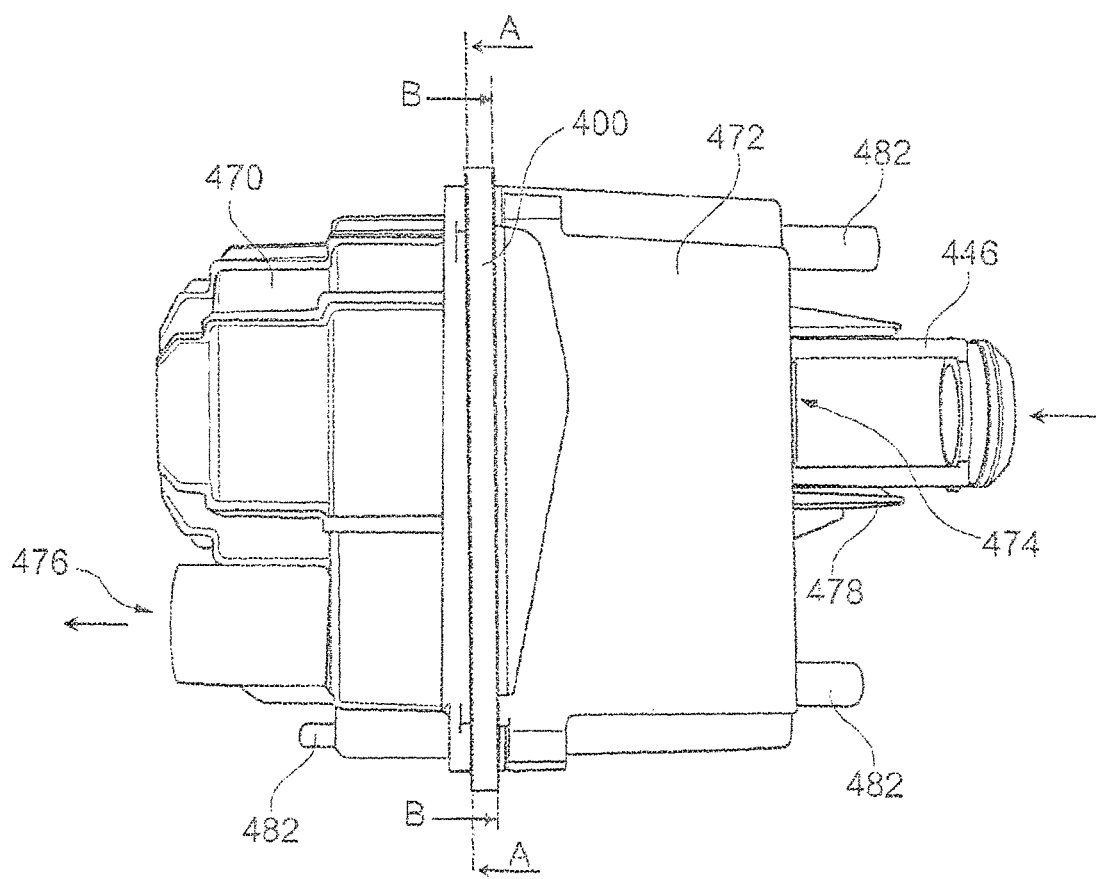
FIG. 16a-16c show three dimensional views corresponding to those of FIGS. 15a, 15b and 15c wherein housing parts are attached to the gasket.
Figure 16C:
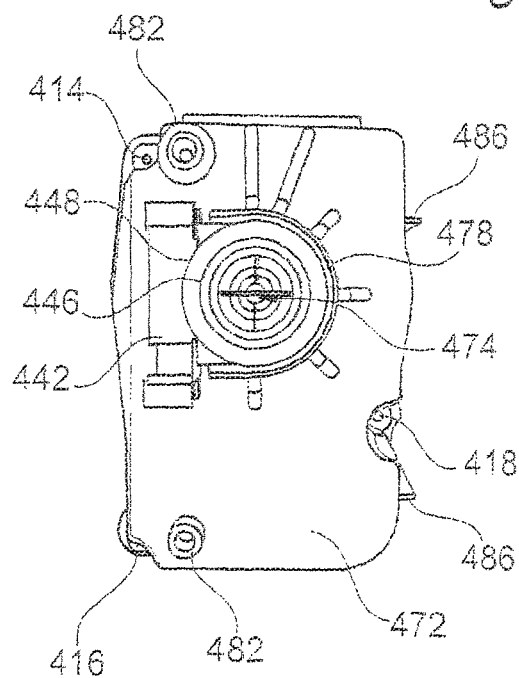
Figure 16B:
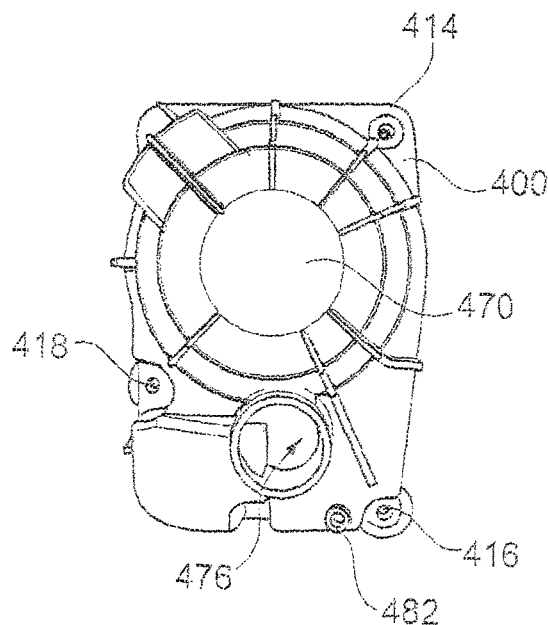

FIGS. 16a, 16b and 16c show views corresponding to those of FIGS. 15a, 15b and 15c wherein blower 200 and fluid channel members 460, 462 are covered by a first flow path housing part 470 and a second flow path housing part 472. First flow path housing part 470 is attached to the first side 450 of gasket 400 and second flow path housing part 472 is attached to the second side 452 of gasket 400 (compare FIG. 14). First and second housing parts 470, 472 are provided with connection means corresponding to holes 414, 416, 418 of gasket 400 including, e.g., protrusions, recesses and/or aligned bores for introducing fastening screws or bolts or the like. In FIGS. 16c and 16b, the respective means are identified using the same reference numerals as with regard to gasket 400, i.e., 414, 416 and 418.

The second flow path housing part 472 comprises an inlet 474 being in fluid communication with the first fluid flow path 460a, opening 408 and inlet channel 204 of blower 200, whereas the second housing part 470 comprises an outlet opening or channel 476 being in fluid communication with fluid flow path 462 (462a, 462b), openings 410 and 412 as well as with the outlet opening or channel 206 of blower 200.

At inlet 474 of second flow path housing part 472 there is preferably provided a support and/or noise shield 478. Preferably, shield 478 supports and/or shields noise emitted from an inlet connector 440 (only connecting member 446 forming part of connector 440 shown in FIG. 16a) for connecting second flow path housing part 472 with an air inlet member, preferably an inlet member 600 according to the present invention. Such connector 440 preferably comprises a flow sensor 442 for sensing the flow of the air or air and oxygen entering the flow path housing. To outlet 476 of first flow path housing part 470 there is preferably connected an outlet connector 458 (not shown in FIG. 16), preferably a silicone bellow connector or decoupler, for connecting the flow path housing to a patient connector 456 (not shown in FIG. 16).

Figure 17A:
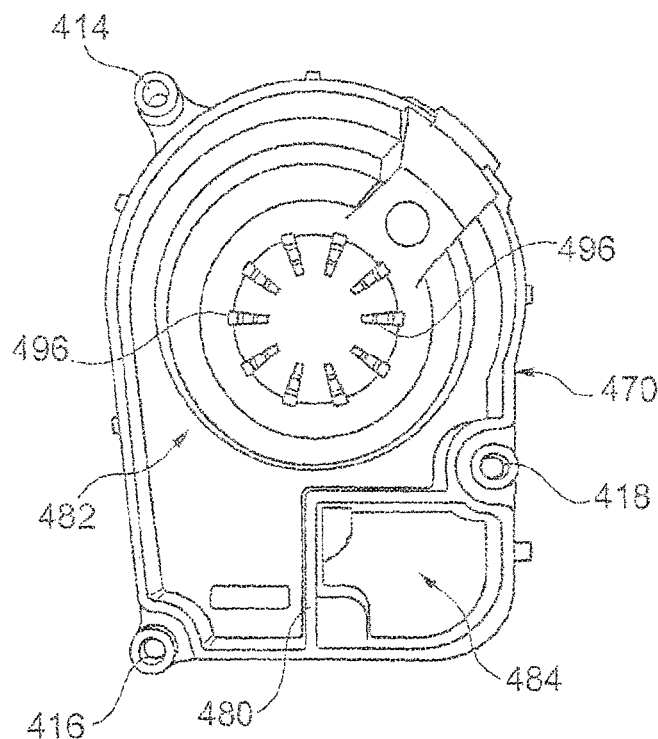
Figure 17B:
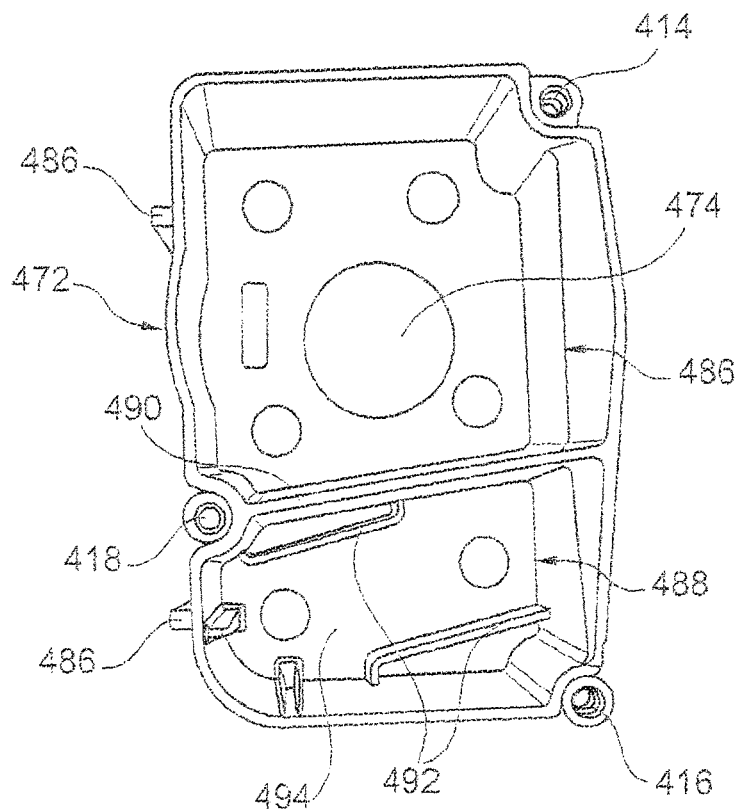

FIGS. 17a and 17b show views into the first and second part of housing 470, 472, respectively. In particular, FIG. 17a shows a view along line A-A indicated in FIG. 16a into first housing part 470, not including blower 200. FIG. 17b shows a view taken along line B-B of FIG. 16a into the second part of housing 472, not including flow channel members 460, 462. As can be seen in FIG. 17a, housing part 470 is separated into two chambers, here by means of a separation wall 480. A first chamber 482 is adapted to accommodate and support blower 200 and motor 208 while chamber 484 constitutes a high pressure chamber from which pressurized air is directed towards the patient. Chamber 482 of first part of housing 470 is preferably provided with supports means 496 for supporting blower 200, and particularly the end of motor 208.

FIG. 17b shows the second housing part 472 also being divided into two chambers, a low pressure chamber 486 and a high pressure chamber 488. Preferably, these chambers are defined and separated by means of a separation wall 490. Low pressure chamber 486 comprises an inlet chamber 464 and is adapted for accommodating or being filled with the first flow channel member 460. Second chamber 488 constitutes a high pressure chamber and is adapted to house second flow channel member 462. Preferably, high pressure chamber 488 of the second housing part 472 comprises spacing means 492 for spacing flow channel member 462 vis-à-vis the back wall 494 of said high pressure chamber 488. According to a preferred embodiment, said structure allows the definition of a distance between back wall 494 and flow channel member 462 so that air flowing from the blower 200 in a pressurized state through channel 462a is redirected by the back wall 494 of the second housing 472 to then enter flow channel 462b in a direction generally opposite to the one through channel 462a. The pressurized air flow is then redirected through gasket 400 and through opening 412 into the high pressure chamber 484 of the first housing part 470. Preferably, high pressure chamber 484 is also filled with a flow channel member (not shown) providing a flow path. According to a preferred embodiment, outlet 476 of a first housing part 470 is displaced in the view according to FIG. 17a so that it is, in this view, hidden by the back wall of blower chamber 482.

The gasket and the further structures described above are arranged as such that the air flow, as indicated by arrows in FIGS. 15a and 16a, enters the air path at opening 474 to then flow through low pressure channel 460a and gasket 400 through opening 408 and entering blower 200 at inlet 204. The air is then accelerated and pressurized, as described above, and exits blower 200 at outlet opening 206 passing gasket 400 at opening 210 from the first side of the gasket to its second side. The pressurized air flow then flows through high pressure channel 462a in high pressure chamber 488, is then redirected by approximately 90° by back wall 494 of high pressure chamber 488 and flows along the space established between high pressure flow channel member 462 and back wall 494 by means of spacers 492. The flow of air is then again redirected to flow into high pressure flow channel 462b, preferably in substantially the opposite direction to the flow of air through first high pressure channel 462a and passes gasket 400 through opening 412 from gasket's second side to the first side of the gasket. The pressured air flow thus enters high pressure chamber 484 provided in the first housing part 470 and is directed to outlet 476 where the pressurized air exits the air path.

The gasket 400 according to the present invention, particularly in combination with further features of the air path such as the first housing part 470 and/or the second housing part 472 and preferably in additional combination with blower 200 and/or one or more of the air path members allows a compact, efficient and effective flow path arrangement which is easy to produce, to assemble and to maintain. In particular, the flow path as discussed above can be assembled as a single module which can be easily inserted into a ventilation device and individually exchanged to replace without major efforts. Air path assembly is particularly beneficial as regards the power and effectiveness of the blower required to provide a desired pressure to a patient and for reacting on changes in the desired flow and/or pressure. Furthermore, the air path of the present invention emits less noise both via the structural components and via the air flow.

FIG. 18 shows a three dimensional top view of a preferred air path according to the present invention. The air path starts with an inlet member, preferably inlet member 600 according to the invention and to be described below from which air flows through a connector portion 440 into flow path housing 470/472. Connector portion 440 is preferably provided as or comprises a flexible, preferably made of silicone, tube portion 446 which can be plugged into to flow path housing outlet 474 and/or inlet member 600. Connector portion 440 preferably comprises a flow sensor 442. At the outlet 476 of flow path housing 470 there is preferably provided a patient connector 456 which is preferably flexibly coupled to outlet 474 by means of a decoupling member or outlet connector 458, preferably a silicone bellow structure. Between the decoupling member 458 and the patient connector 456 or in decoupling member 458 there are preferably provided ports for or at least parts of a pressure sensor 466 for sensing pressure of the breathing gas applied to a patient.

FIG. 18 also shows support members 482 provided on housing parts 470, 472 for advantageously supporting the flow path in a breathing device (to be further discussed below). Said support members are provided with elastic dampeners 468, preferably made of silicone. Housing parts 470 and/or 472 preferably comprise rips 486 provided at one side thereof, preferably at its/their lower side when seen in the orientation of the housing in a breathing device in operation.

Figure 19A:
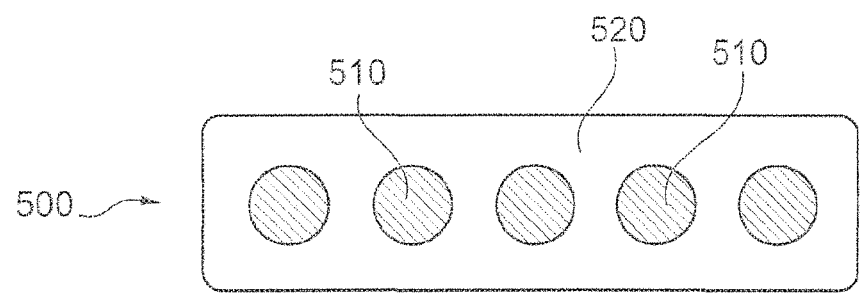
FIGS. 19a-19b show preferred embodiments (FIG. 19a, FIG. 19b) of a cable in accordance with the present invention.
Figure 19B:
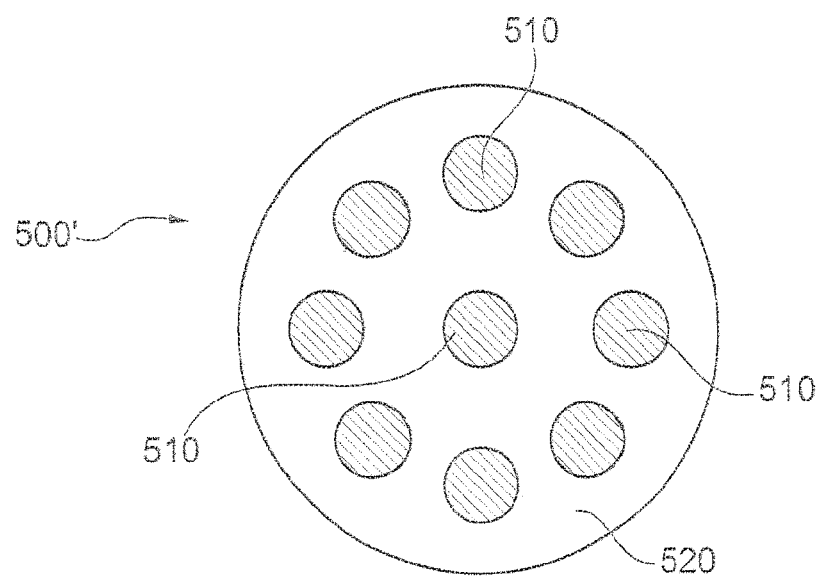

FIGS. 19a-19b show a cable in accordance with the present invention. The cable 500 comprises one or more, in the shown embodiments 5 metal wires, here stranded wires or litz wires 510. Stranded wires or litz wires 510 may be of equal or differing size or diameter. In the embodiment of FIG. 19a wires 510 are located next to one another. In the embodiment of FIG. 19b cable 500, here referred to as 500', comprises 9 wires 510 arranged in a different order such as in a circle around a centre wire 510. Apart from the alignment of wires 510, the embodiments shown in FIGS. 19*a* and 19*b* correspond to one another. Wires 510 are embedded in a silicone coating 520 which functions both as a coating for each individual wire 510, as positioning means for each wire 510 with regard to neighbouring wires 510 and/or as self sealing skin allowing the cable 500, 500' to be sealingly arranged between two or more separate components without the need for additional sealing material. Preferably, silicone coating 520 has a thickness of at least 0.5 mm, preferably of at least 0.6 mm and preferably of at least about 0.7 mm, measured along the shortest distance from the outer circumference or outer surface of cable 500, 500' to one of the litz wires 510.

The cable 500, 500' according to the present invention constitutes a self-sealing cable which provides insulation of different metal wires, such as different stranded or litz wires, vis-à-vis one another as well as vis-à-vis the surrounding. Any desired predefined schematic arrangement of wires 510 constituting cable 500, 500' can be manufactured in a predefined way which is individualized for the desired purpose. The silicone coating of the cable 500 and each of wires 510 allows an effective and improved sealing not only of cable 500 vis-à-vis its exterior. Cable 500, 500' can also advantageously be clamped between two parts of, e.g., a housing, wherein an improved sealing of the interior of the housing against the exterior of the housing (or vice versa) is achieved by a cable 500 according to the present invention. Cable 500 particularly allows to be run into or out of a high pressure chamber without negatively influencing the pressure relations existing in the chamber.

Figure 20A:
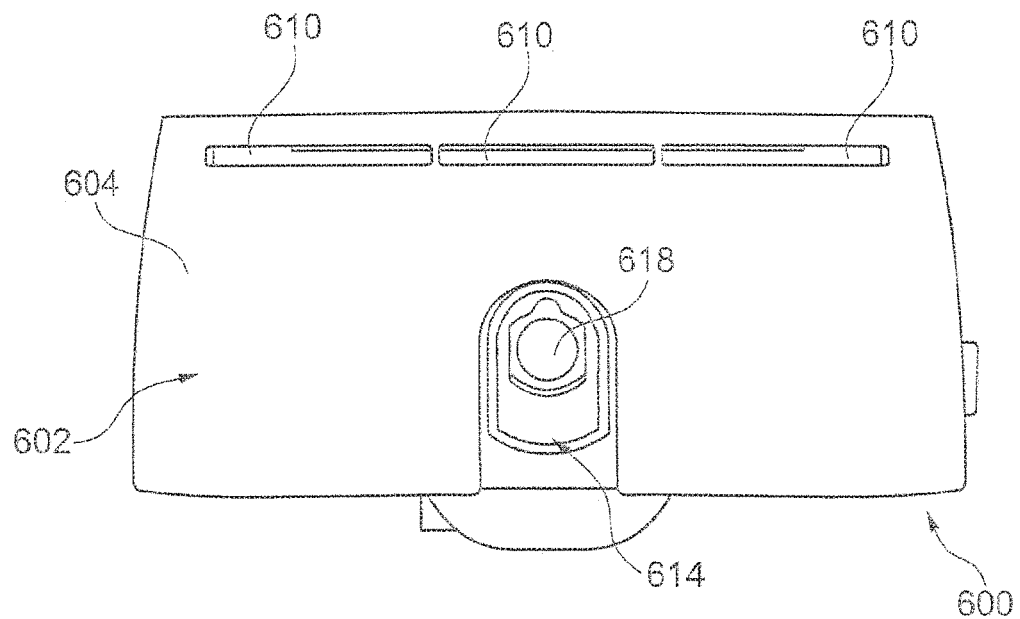
Figure 20D:
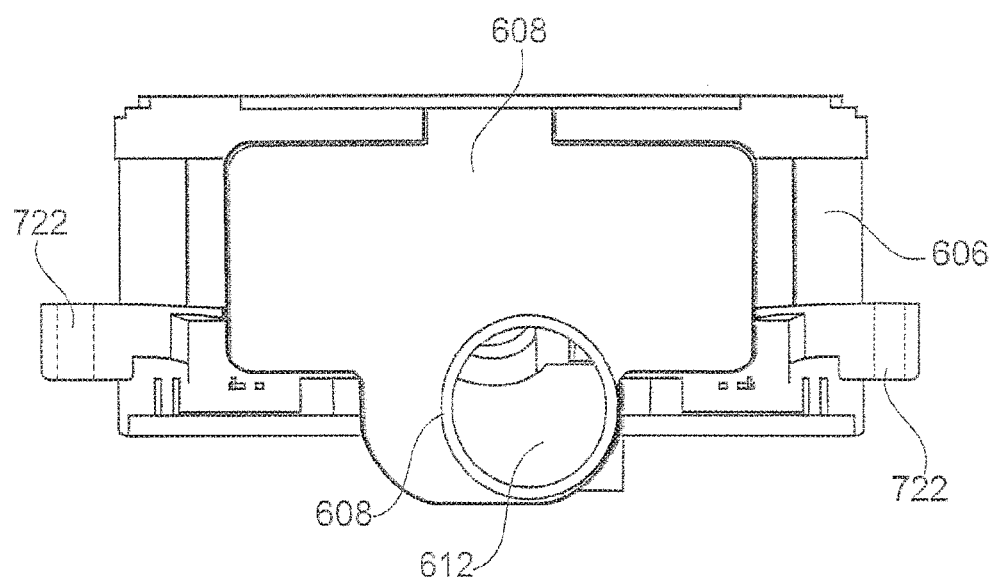
Figure 20B:
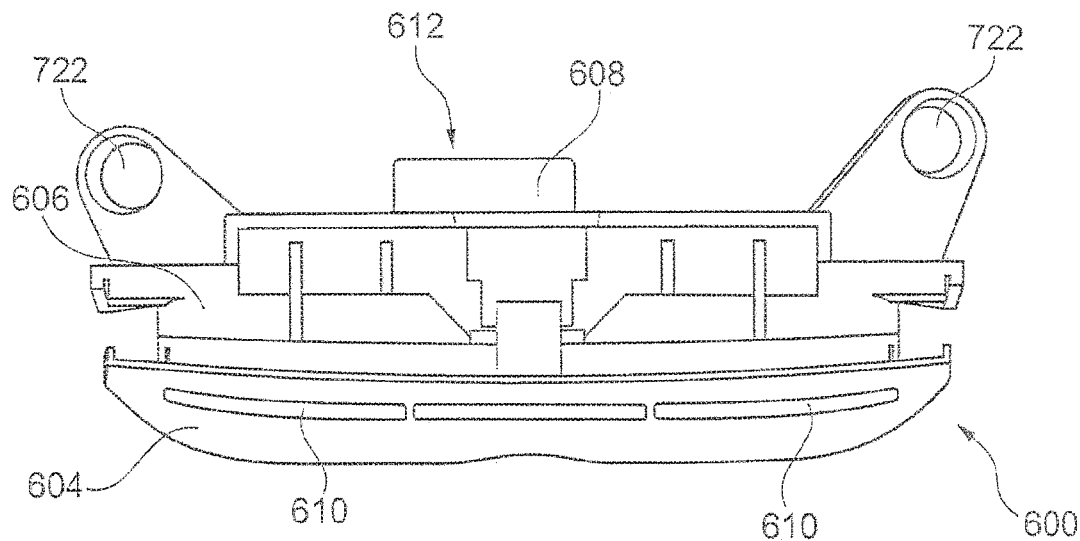
Figure 20C:
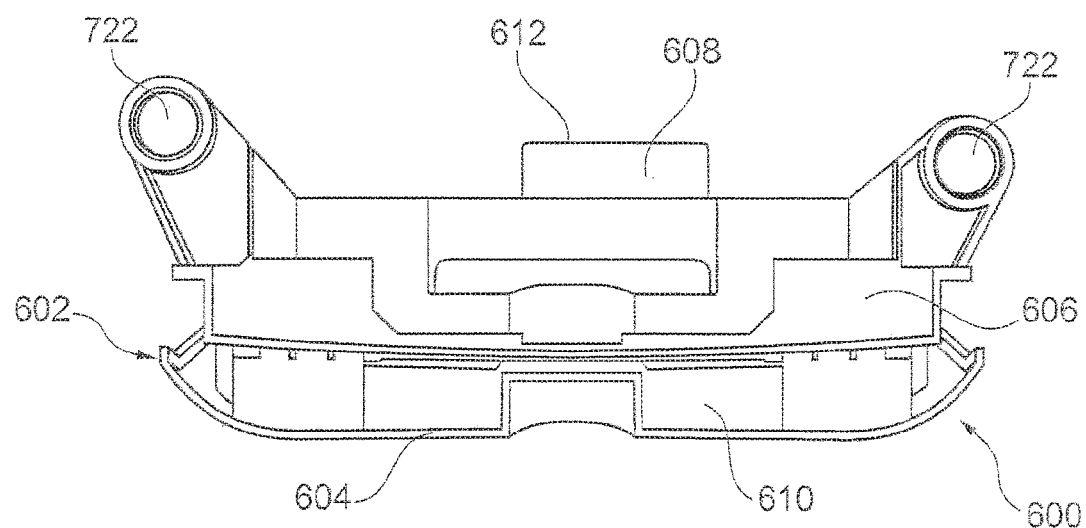

FIG. 20*a* shows a side view of an inlet member 600 according to the present invention as seen in a back view of a ventilation device, e.g., such as in FIG. 4. and FIG. 20*b* show a top view of said inlet member 600 and FIG. 20*c* shows a bottom view. FIG. 20*d* shows a side view seen in an opposite direction of the view shown in FIG. 20*a*.

Figure 21A:
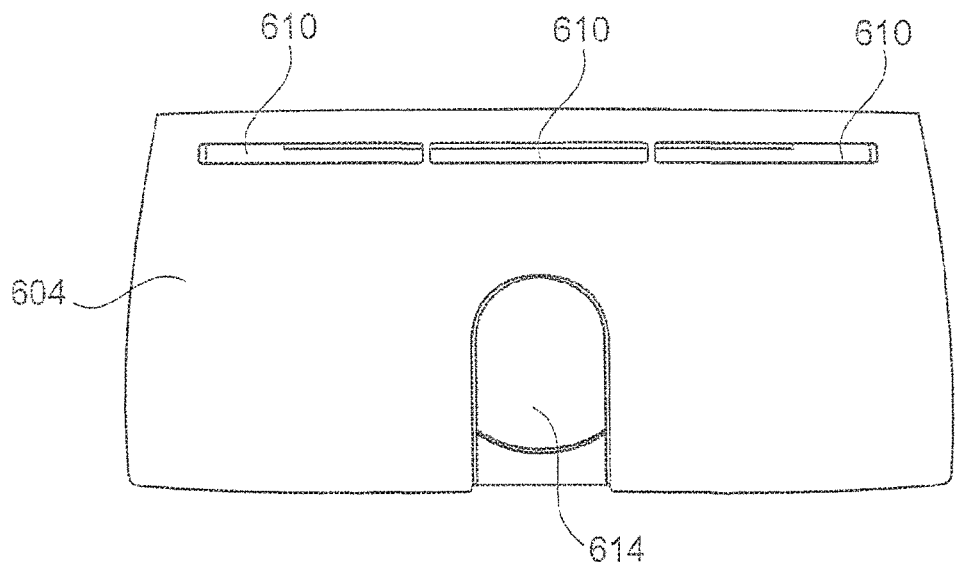
FIGS. 21a-21d show a preferred embodiment of a first inlet housing part while the three dimensional views shown in FIGS. 21a to 21d correspond to those of FIGS. 20a-20d.
Figure 21D:
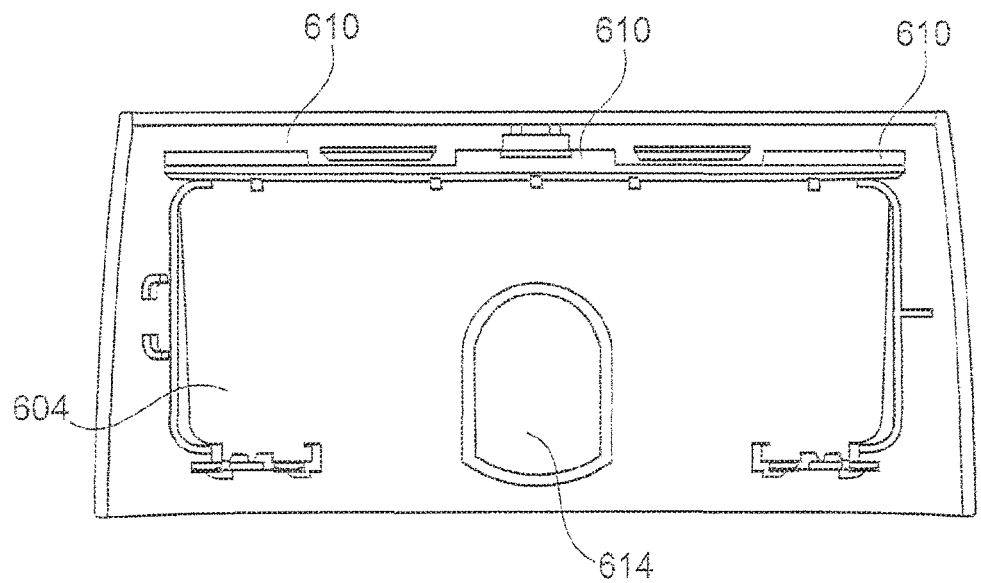
Figure 21B:
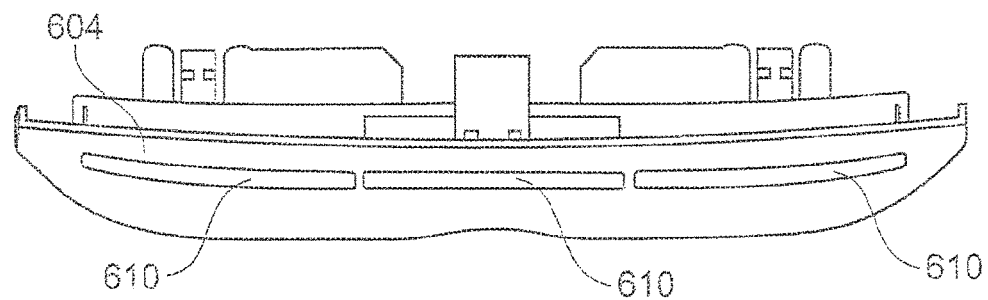
Figure 21C:
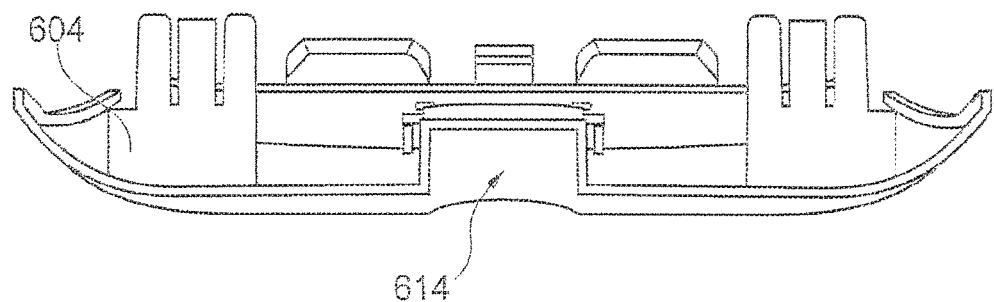
Figure 22A:
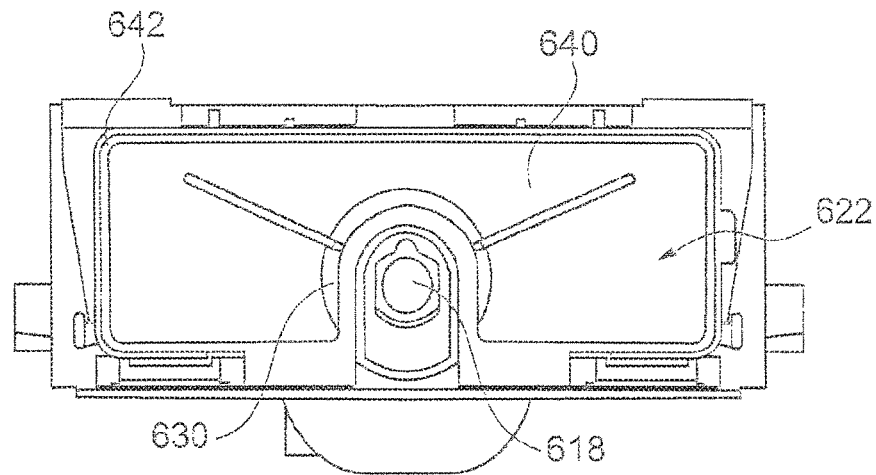
FIGS. 22a-22d show a preferred embodiment of a second inlet housing part while the three dimensional views shown in FIGS. 22a and 22d correspond to those of FIGS. 20a-20d.
Figure 22D:
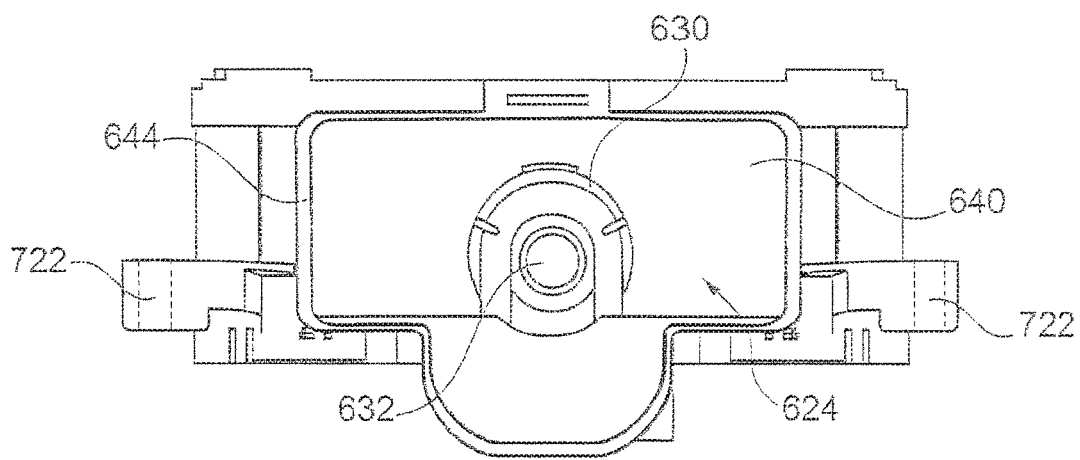
Figure 22B:
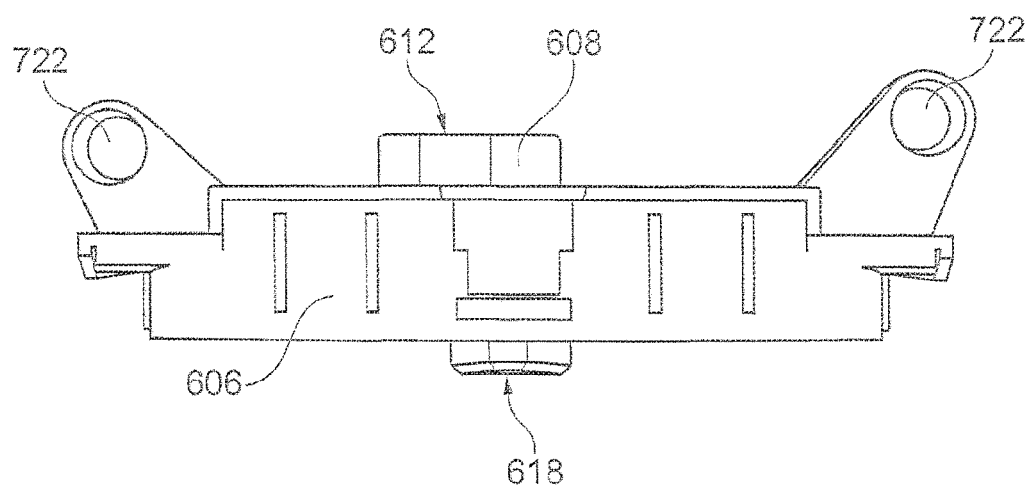
Figure 22C:
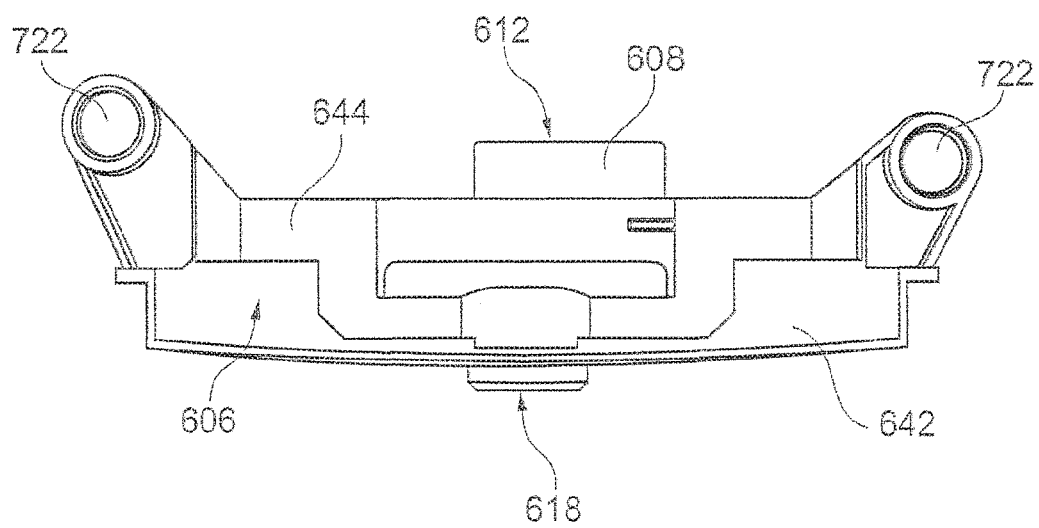

Inlet member 600 comprises an inlet housing 602 comprising at least a first inlet housing part 604 and a second inlet housing part 606. According to the shown embodiment, the housing comprises an additional third inlet housing part 608. The first part 604 of the filter housing comprises and/or defines air inlets 610 (which according to a preferred embodiment correspond to air inlet 110 of the ventilation device discussed with regard to, e.g., FIG. 4). According to a preferred embodiment, one or more air inlets 610, 110 comprise an air shield deflecting the air entering the housing and dampening noise from inside the ventilation device. Such air shield preferably extends from the inner side of the first part, preferably from a portion below the air inlet(s), at least partly along the opening, preferably extending across the opening at an angle to the plane of the opening. Seen in a direction of the air flow through the air inlet(s) the shield preferably at least partly crosses the air flow. Preferably, the inlet(s) define openings in a vertical surface of the first part. An outlet 612 is provided in the third part 608 of housing 602. The inlet member 600 also comprises a second inlet 618 (according to a preferred embodiment corresponding to inlet 118 discussed above, e.g., with regard to FIG. 4). Such second inlet 618, preferably for the supply of additional oxygen, is provided in the first 604 or second 608 inlet housing part. In the shown preferred embodiment the second inlet 618 is provided by a second inlet member 662 connected to the second inlet housing part 608 while first inlet housing part 604 is provided with an opening or cut out 614 allowing access to the second inlet from the exterior of inlet member 600. FIGS. 21*a* to 21*b* show a preferred embodiment of a first inlet housing part 606 while the views shown correspond to those of FIG. 20. FIGS. 22*a* to 22*d* show a preferred embodiment of a second inlet housing part 604 while the views shown correspond to those of FIG. 20. In FIG. 22*b* and FIG. 22*c* (top and bottom view) also the third inlet housing part 608 is shown, which, however, is not shown in FIGS. 22*a* and 22*d*.

First housing part 604 comprises an inlet opening, preferably extending along a large area, which is adapted to be covered by an inlet filter 620. First inlet housing part 604, inlet filter 620, second inlet housing part 606 and third inlet housing part 608 are arranged such that air flowing into the inlet member 600 through air inlet 610 flows along an inlet or filter path through filter 620 and then into an inlet chamber 622 defined between inlet filter 620 and an air outlet 612 defined in the third inlet housing part 608. From that inlet chamber 622 the inlet path further extends, preferably through a second inlet chamber 624 defined between/by the second part of the housing 606 and the third part of the inlet housing 608. Said second chamber 624 preferably functions as a muffling chamber and is preferably filled with an inlet flow path member 626 defining an inlet flow path. From the second chamber 624 the inlet path preferably extends out of the inlet member 600 through outlet opening 612.

Preferably, the oxygen inlet 618 opens into an oxygen channel in member 662 which extends from the oxygen inlet 618 through the opening 614 of the first inlet housing part 604 along the second housing part 606 wherein it preferably extends parallel and distinct to inlet filter 620 and the first inlet chamber 622.

A second inlet housing part 606 preferably comprises a first outlet opening 630 being in fluid communication with the inlet air flow and the first inlet chamber 622 as well as a second outlet opening 632 being in fluid communication with and constituting the end of the oxygen inlet channel. First or air outlet 630 and second or oxygen outlet 632 are preferably arranged in a substantially coaxial manner. Air outlet 630 and oxygen outlet 632 preferably open into the second inlet chamber 624. Preferably, air outlet 630 has a ring-shaped cross section or geometry while oxygen outlet 632 has a ring-shaped configuration, preferably surrounding second outlet opening 632. Thus, outlets 630, 632 are arranged such that the air flow through the air inlet 610 and through the filter 620 is mixed with the oxygen supplied through the oxygen inlet 618, with regard to the direction of air and oxygen flow, after the air inlet flow and the oxygen inlet flow have passed the second part of the inlet housing 606 through air outlet 630 and oxygen outlet 632, respectively, and, preferably, in second inlet chamber 624. Said mixing is supported by the directed flow provided by the geometry of the substantially coaxially arranged outlets and starts in the second inlet chamber 624 and is further promoted throughout the flow through the air path. Thus, an excellent mixing of air and additions, such as oxygen, is achieved until the airflow reaches the patient. Preferably, the ring-shaped air outlet 630 extends around oxygen outlet opening 632.

It will be well understood that the first part of the inlet housing 604, according to a preferred embodiment, primarily serves as a shield or cover for protecting inlet filter 620 from being damaged in use, for noise shielding and reduction and simultaneously serves for optically integrating inlet member 600 into a ventilation device, e.g., a device discussed with regard to FIGS. 2 to 5 of the present invention.

The basic structure of a preferred embodiment of the second inlet housing part 606 is preferably as follows.

Second inlet housing part 606 comprises a substantially planar base wall 640 from which, on at least one side thereof, side walls extend defining, together with base wall 640 an open chamber. In the shown embodiment, side walls 642 define, together with base wall 640 an open first inlet chamber 622. Side walls 644 define, together with base wall 640 an open second inlet chamber 624. As discussed above, first inlet chamber 622 is closed by filter element 620. Second inlet chamber 624 is closed by third inlet housing part 608. Preferably, third inlet housing part 608 is configured a substantially planar lid with a channel like, preferably substantially circular, protrusion defining outlet 612.

Figure 23A:
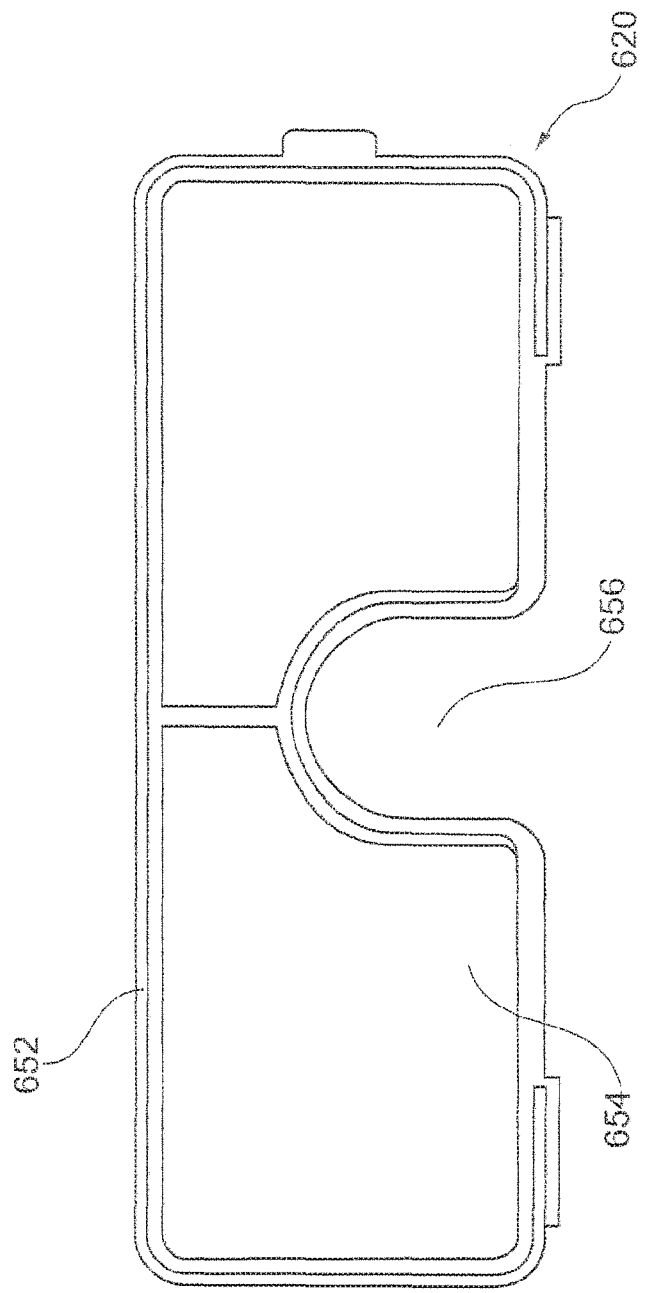
Figure 23B:
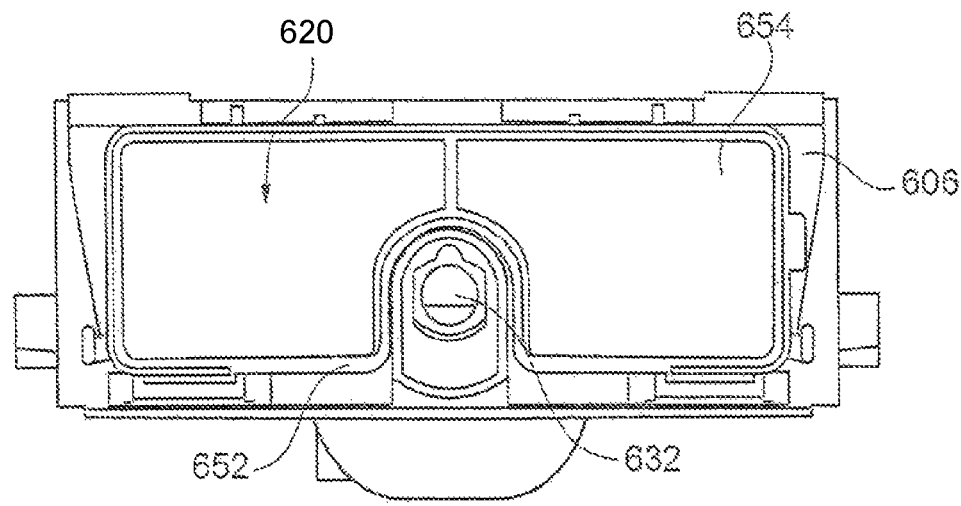
Figure 23C:
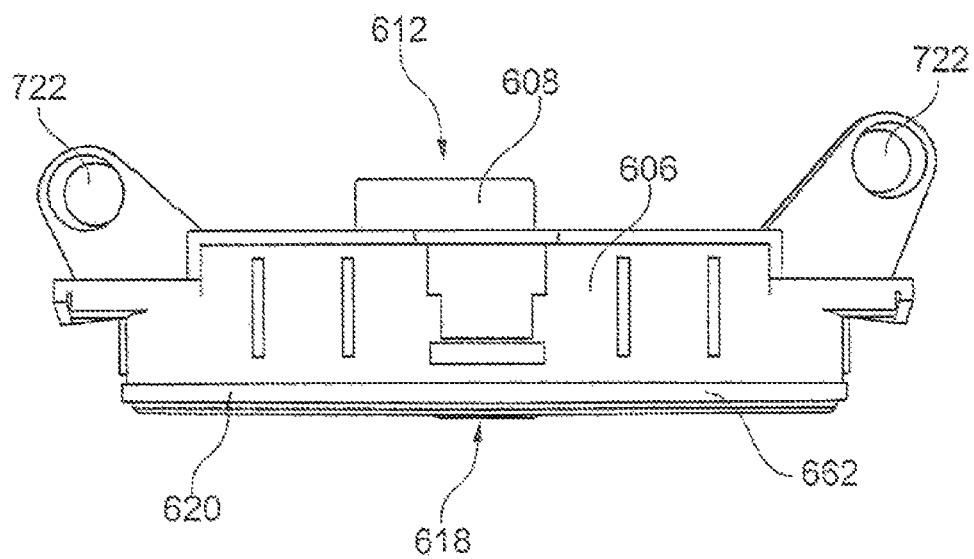

Filter element 620 is shown in FIGS. 23*a* to 23*c* of which FIG. 23*a* shows a preferred embodiment of filter 620 in a side view (compare FIGS. 20*a*, 20*b*). FIG. 23*b* shows filter element 620 in accordance with the view shown in FIG. 23*a* connected to second inlet housing part 606. FIG. 23*c* shows a top view according to FIG. 22*b* with second inlet housing part 606 and inlet filter 620. Filter element 620 comprises a frame 652 as well as a filter material 654 connected to the frame 652. The filter element 620 and thus its frame 652 and filter material 654, preferably generally extend in one or at least one plane. The frame 652 is preferably endless and more preferably of generally oval or rectangular configuration defining a plane, preferably plane of the filter element, in which the filter material 654 extends. The filter element preferably extends across the cross section of the air path between the air inlet and the air outlet to ensure that all air entering the device flows through the filter and is thus filtered. It will thus be appreciated that the filter element may take other forms than the ones referred to herein. It is, however, preferred that the filter element has a substantially planar extension or configuration. Preferably, the filter element 620 comprises a cut-out, recess or opening 656, particular for allowing the extension of the additional or second inlet or the corresponding second inlet path past the filter element (see FIGS. 23*a*, 23*c* and 22*b*), without having to flow through the filter. This particularly allows the parallel supply from ambient air and oxygen along to separate flow paths which can then be combined or mixed downstream of the filter element. This improves the possibility of proper mixing the ambient air with an additional supply of oxygen and at the same time reduces the loss of the supplied oxygen, e.g., via the air inlet. The oxygen inlet path, which preferably has a channel like configuration, thus extends from the oxygen inlet, preferably forming part of the second part of the inlet housing along the filter element to the outlet provided in the second part of the housing. The oxygen inlet path is thus preferably part of the second part of the inlet housing. Preferably, the inlet path protrudes from the second part of the inlet housing and extends up to or through the first part of the inlet housing. Preferably, the first part of the inlet housing is provided with an opening or recess for allowing easy accessibility of the oxygen inlet. The oxygen inlet is preferably provided with a connection means for connecting an oxygen supply (not shown).

The filter material is connected to the filter frame, preferably by means of gluing or bonding. However, it will be understood that different technologies may be applied. The filter frame is preferably made of a plastic material. According to a preferred embodiment, a sealing or positioning means such as a rim or lip is provided for allowing proper positioning and/or improved sealing contact of the filter frame with regard to the first and/or second part of the filter housing. Such sealing or positioning means can either be provided on the frame and/or on the first and/or second part of the housing. The filter frame is preferably made from elastic material, such as TPE. This preferably allows improved sealing of the filter in the housing and reduces bypass flow.

The second inlet chamber 624 preferably constitutes a muffling chamber which is preferably filled with a muffling material, preferably a foam material such as silicone foam, which preferably defines a part of an inlet flow channel. The muffling chamber 640 also comprises an outlet opening 612 adapted to be connected to a flow path of a breathing device, preferably a flow path of a breathing device according to the present invention. Since, according to a preferred embodiment, the flow of air and oxygen are mixed, preferably upon entry into the inlet muffling chamber and/or along the inlet fluid flow path, the inlet muffling chamber comprised only one outlet through which the combined flow of air and oxygen flows.

The inlet housing parts 604, 606, 608 preferably comprise fastening means for connecting the different housing parts with one another and/or with a breathing device. Preferably, such fastening means are known to the person skilled in the art such as snap-fit fastening means, hole and pin, or screw-hole connections.

Figure 24:
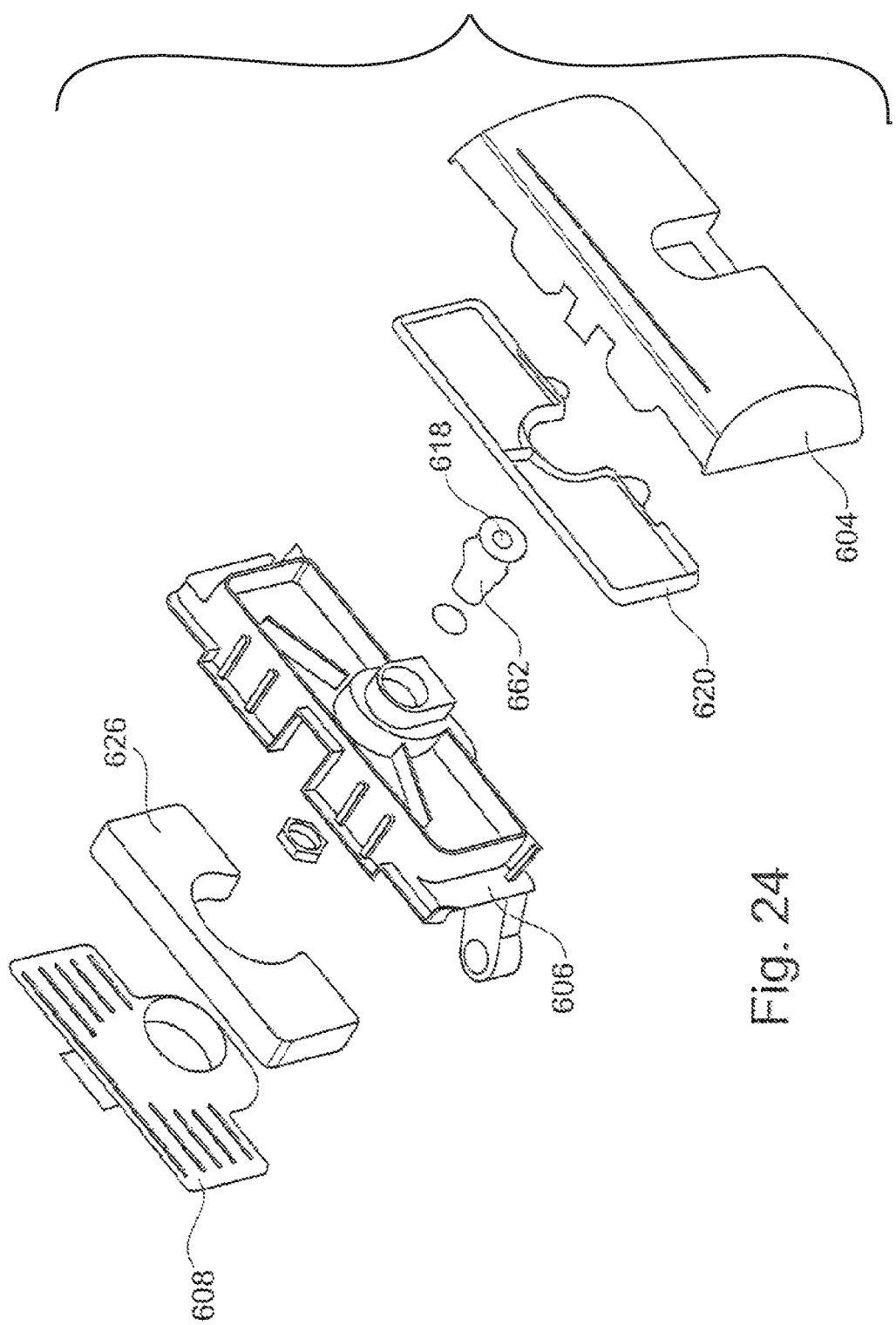
FIG. 24 shows an exploded three dimensional view of the inlet member according to FIGS. 19a to 22d.
Figure 25A:
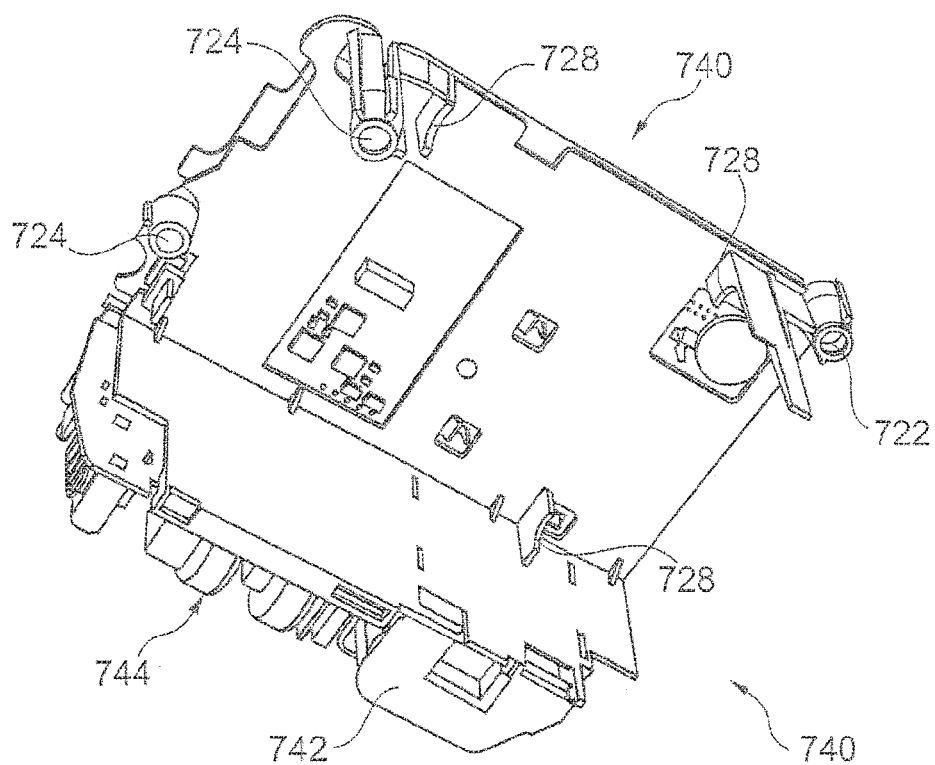
FIGS. 25a-25b show a three dimensional view of an electric module according to the invention.
Figure 25B:
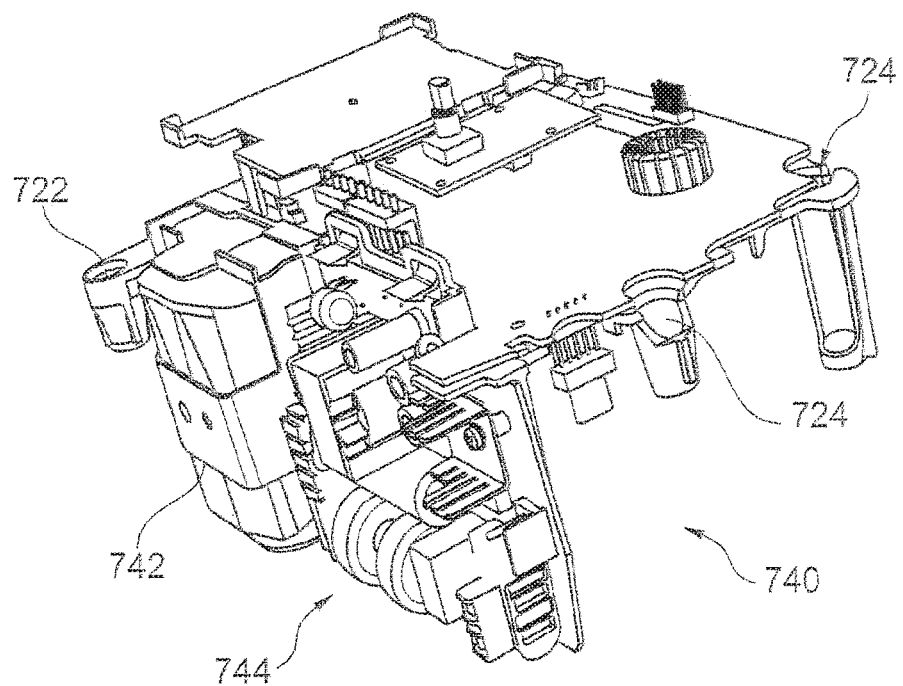
Figure 26A:
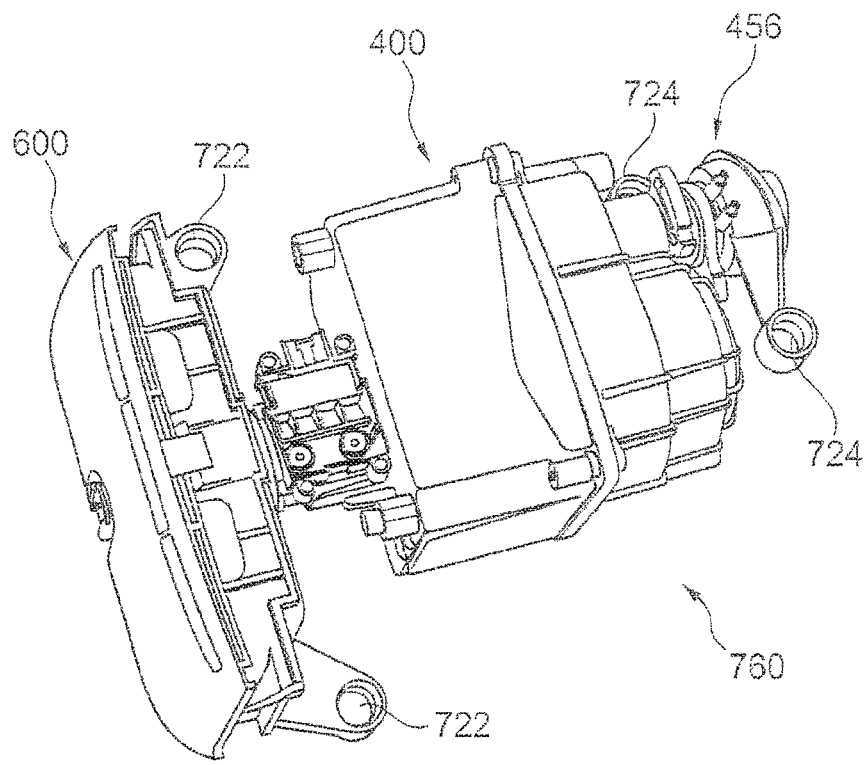
FIGS. 26a-26b show a three dimensional top (FIG. 26a) and bottom (FIG. 26b) view of an air path module according to the invention.
Figure 26B:
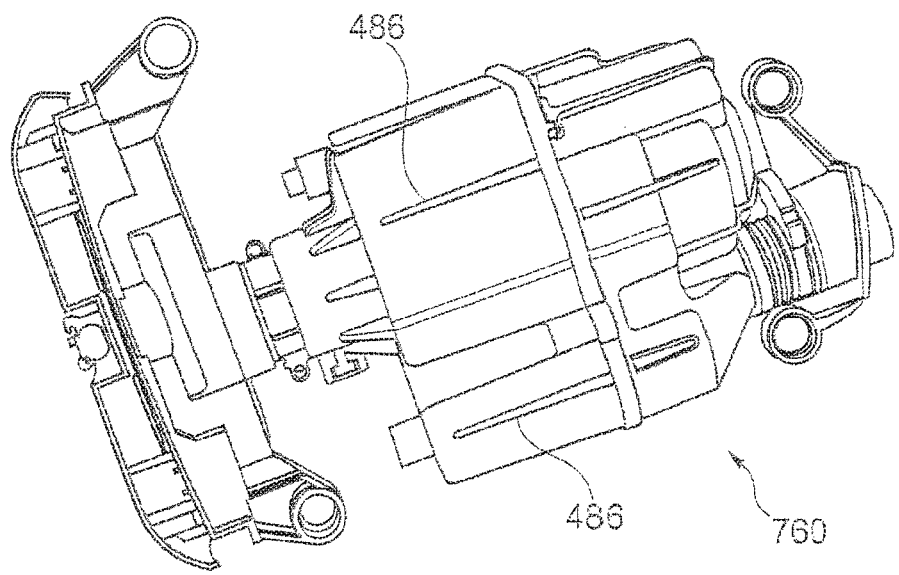
Figure 27:
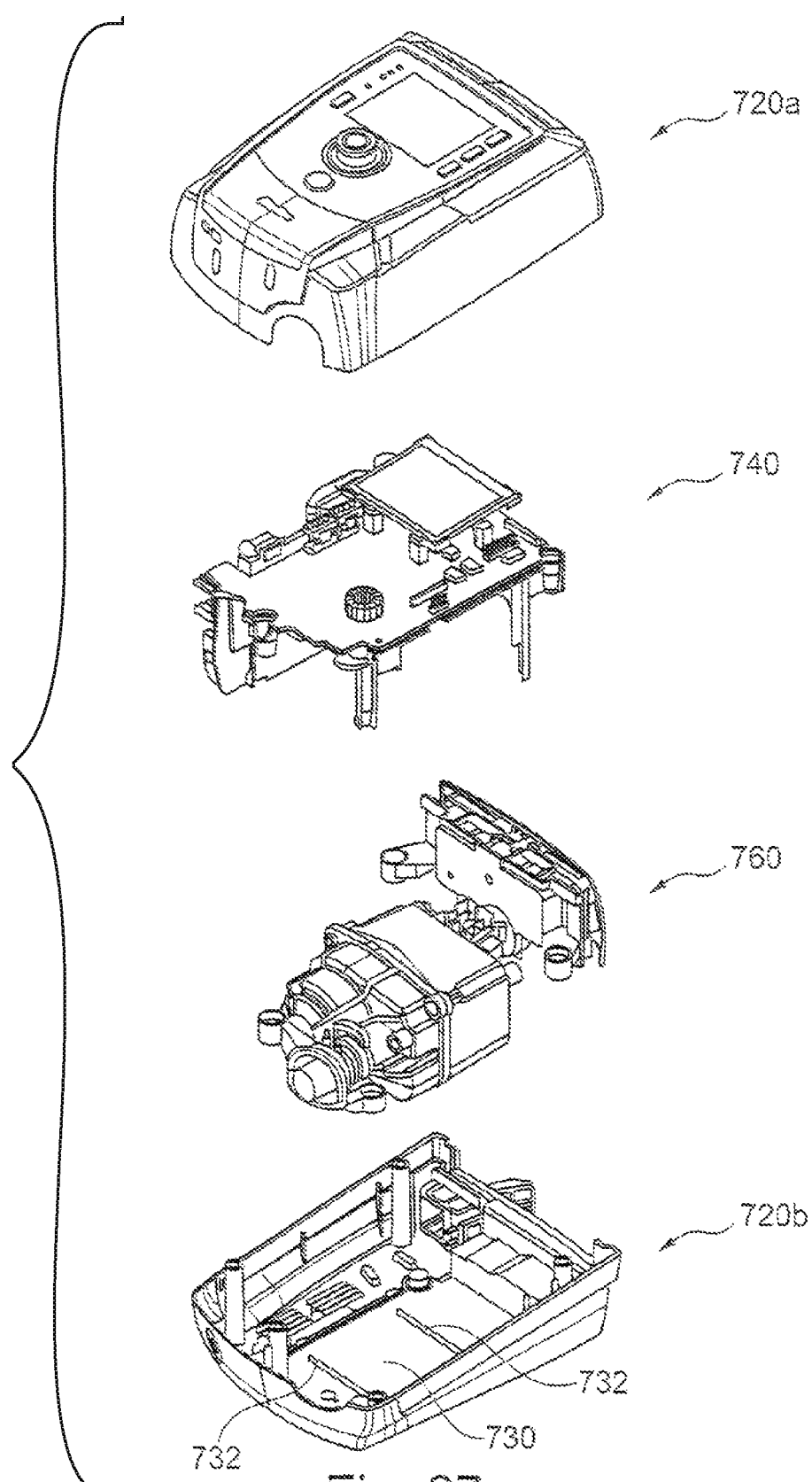
FIG. 27 shows an exploded three dimensional view of the modular ventilation device according to, i.a., FIGS. 24a to 26b.

FIG. 24 shows an exploded view of the inlet member according to FIGS. 19*a* to 22*d*. Here, the relation and orientation of first inlet member housing part 604, second inlet member housing part 606, third inlet member housing part 608, filter element 620, inlet flow path member 626 as well as second channel 662 and oxygen inlet 618 can be readily seen.

The invention additionally and alternatively relates to a modular ventilation or breathing device as referred to above and particularly for use with a blower, impeller, gasket, air path and/or inlet member according to the present invention.

The respiration or ventilation device 100 according to the present invention is preferably of an advantageous modular structure and comprises a housing module 720, preferably corresponding to housing 104 as referred to above, provided with operator input and display means. Additionally, there is provided an electric module 740, preferably comprising a skeleton carrier for carrying, i.a., a control unit, battery pack 742, power supply 744 and further electronics required, for providing structural support and/or for allowing defined positioning of the modules and parts of the ventilation device. The ventilation device 100 further comprises an air path module 760 comprising an air path housing, comprising an air path inlet and an air path outlet, in which a blower is located. Preferably, the air path (here also referred to as air path 400) is the air path according to the present invention comprising air path housing 470, 472, gasket 400 etc. while the gasket and/or the air path housing carries a blower 200 including a motor 208, preferably the blower according to the present invention.

Preferably, the air path module includes an inlet member, preferably the inlet member 600 in accordance with the present invention and/or a patient connector 456. Preferably, inlet member 600 is connected to air path 400 via a plug-in bushing 458, preferably made of silicone and comprising flow sensor 466. Preferably, bushing 458 also serves for dampening and decoupling inlet member 600 from air path housing 400. Preferably, patient connector 456 is connected to air path 400 via a connector member 458, preferably being arranged as a bellow like silicone member for dampening and decoupling patient connector 456 from air path housing 470, 472.

Preferably, inlet member 600 comprises two fastening bores 722 wherein patient connector 456 also comprises two fastening bores 724. Preferably, air path housing 470, 472 comprises structural location members 482 which may be provided with dampening elements 468.

The electric module 740 is preferably further adapted to be connected to and support the housing of the ventilation device as well as to support and/or position the air path module. In addition, the skeleton carrier and/or the electric module is preferably adapted to and comprises means for allowing a proper alignment and positioning of the different parts and modules of the ventilation device such as the parts of the housing module and/or the air path element. The electric module preferably comprises the power supply 744, battery or accumulator pack 742, control unit and/or a display unit. Skeleton member preferably comprises support 722, 724 structures being, in an assembled state, aligned with fastening bores 722, 724 provided in the inlet member 200 and/or the patient connector 456. Skeleton member furthermore comprises positioning means 728 for cooperating with location members 482 of the air path housing.

The housing module 720 comprises an upper housing part 720a and a lower housing part 720b (compare discussion of FIGS. 3 to 5 with regard to housing parts 140a and 104b, preferably corresponding to housing part 720a and 720b).

Air path module 760, which comprises every part of the air path, i.e. every part of the ventilation device being in contact with inhaled or exhaled air, is laid into the lower part 720b of housing module 720. For supporting air path module 760 in housing module 720 there is preferably provided a dampening and/or supporting pad 730 which comprises structural means, preferably raised portions 732, for supporting air path module 760. Preferably, support structures 732 are adapted to cooperate with structural support means 486 provided on one or both parts of air path housing 470, 472. Preferably raised support structures 732 and raised support structures 486 are adapted as elongated means, e.g., elongate rims, wherein the support structures 432 of the supporting pad 730 and the support structures 486 of the air path preferably extend into different directions and preferably extend generally transverse to one another. This preferably improves proper, easy and secure positioning. The air path module 760 is simply laid into lower part 720b of housing module 720 without the need for any further fastening or connection members. The air path is positioned such, that holes 722 and 724 provided in inlet member 200 and patient connector 456, respectively, are aligned with corresponding holes 722b and 724b provided in the lower housing part 720b. Preferably, holes 722b and 724b are provided in protruding posts which are in aligned contact with inlet member 200 and patient connector 456.

Preferably, the device comprises a fan (not shown) placed on the lower part 720b of housing module 720 and, preferably, corresponding with a corresponding opening or air inlet (not shown) provided in said lower part. The location of the fan is preferably such that, after assembly, the fan is positioned below the electric module 740 and preferably below power supply 744 and/or battery or accumulator pack 742. Preferably, the fan is adapted and positioned to direct an air flow along power supply 744 and/or battery or accumulator pack 742. The air flow may then advantageously be directed along the electric module 740 to the inlet member 600 being provided with respective air outlet openings. The air flow provided by the fan is defined and separated from the air flow entering the device and being provided to the patient. Such air flow is preferably adapted to cool one or more electric components. This may improve operation of the device and/or the charging process of the accumulator pack.

Preferably, the fan is supported, preferably clamped, in the device between lower part 720b and electric module 740. Preferably, no screws or fasting means are used. The fan preferably comprises an elastic, preferably silicone, jacket or sheath extending around at least part of the (rigid) fan housing. Such elastic structure may allow the fan to be properly dampened, positioned and/or handled. Preferably, the lower part 720b of housing module 720, the electric module 740 and/or the elastic jacket comprise(s) structural means for properly positioning the fan in the device. Such solution particularly allows the provision of an advantageous fan which can easily be handled, properly positioned and advantageously supported in the device, particularly improving noise reduction. Preferably, the silicone jacket and the air inlet provided the lower part 720b are aligned in a sealing manner, sealing air path of the air entering the inlet and the fan against the surrounding inside the device. The elastic, preferably silicone, jacket is thus preferably multifunctional in that it provides mechanical support, servers sealing purposes, and dampens or decouples the fan from the housing.

Then, the electric module 740 is placed over the air path module. Electric module 740, preferably its skeleton member, is provided with fastening means or holes 722 and 724 which are aligned with fastening means or holes 722 and 724 of the air path module 740. In addition, electric module 740 comprises support structures 728 which cooperate with support structures 468, 482 of the air path module 760 and thus allow proper positioning and securing in place of air path module 740. Next, the upper part of the housing module 720a is placed over the electric module 740. Hosing module 720a comprises fastening structures of holes 722 and 724 corresponding to and aligned with respective holes 722, 724 of the lower housing module 720, holes 722, 724 of the air path module 760 and holes 722, 724 of the electric module 740. By screwing a screw into these holed, the parts of the housing module are then screwed to one another, thereby simultaneously fixing and securing the position of the air path module and the electric module, generally without the need for further fixation. Preferably, one or more of fastening means or holes 722, 724 comprises an end stop (not shown) serving as an abutment for air path module in case of excessive movement of the air path module, e.g. resulting from a strong hit against the device.

While the invention has been illustrated and described in detail in the drawings and foregoing description, such illustration and description are to be considered illustrative or exemplary and non-restrictive; the invention is thus not limited to the disclosed embodiments. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single unit may fulfil the functions of several items recited in the claims. The mere fact that certain measures are recited in mutually different dependent claims does not indicate that a combination of these measures can not be used to advantage. Any reference signs in the claims should not be considered as limiting the scope.

The invention also covers all further features shown in the figures individually although they may not have been described in the afore description. The present invention covers further embodiments with any combination of features from different embodiments described above.

The present invention also covers the exact terms, features, values and ranges etc. in case these terms, features, values and ranges etc. are used in conjunction with terms such as about, around, generally, substantially, essentially, at least etc. (i.e., "about 3" shall also cover exactly 3 or "essentially radial" shall also cover exactly radial).

The invention claimed is:

1. A blower configured to pressurize a supply of gas, the blower comprising:
 a gas inlet;
 a gas outlet configured to discharge the supply of pressurized gas;
 a rotatable shaft; and
 an impeller configured to be rotated by the rotatable shaft and pressurize the supply of gas, the impeller comprising:
  a central hub that receives the rotatable shaft;
  a shroud; and
  a plurality of vanes extending from a surface of the shroud toward the gas inlet, each vane radiating outwards from the hub,
 wherein the outer diameter of the shroud varies between maximum portions with a maximum outer diameter and minimum portions with a minimum outer diameter,
 wherein the maximum portions are located at the vanes and the minimum portions are located between the vanes,
 wherein a portion of each vane has a positive curvature with a concave surface that faces the direction of the impeller's rotation, and
 wherein the portion of the vane that is positively curved begins at an intermediate point and extends to the radially outermost end of the vane, the intermediate point being offset from the hub by a predetermined distance.

2. The blower of claim 1, wherein the perimeter of the shroud is concave between the maximum portions and the minimum portions.

3. The blower of claim 2, wherein the circumference of the shroud is wavy shaped or saw tooth shaped.

4. The blower of claim 1, wherein the plurality of vanes are formed integrally with the shroud and the impeller is formed of a plastic material.

5. The blower of claim 1, wherein the plurality of vanes includes an odd number of vanes.

6. The blower of claim 1, wherein the impeller has a moment of inertia of less than 3.2 g cm$^2$.

7. The blower of claim 1, wherein the moment of inertia lies in a range between 1.2 and 3.2 g cm$^2$.

8. The blower of claim 1, wherein the impeller includes only one shroud.

9. The blower of claim 1, wherein the perimeter of the shroud is concave between the maximum portions and the minimum portions,
 wherein the circumference of the shroud is wavy shaped or saw tooth shaped,
 wherein the plurality of vanes are formed integrally with the shroud and the impeller is formed of a plastic material,
 wherein the plurality of vanes includes an odd number of vanes,
 wherein the impeller has a moment of inertia of less than 3.2 g cm2, and
 wherein the impeller includes only one shroud.

10. A respiratory apparatus configured to treat a patient with a respiratory disorder, the respiratory apparatus comprising:
 the blower of claim 1;
 a housing that encloses the blower and comprises:
  a gas inlet in fluid communication with the gas inlet of the blower; and
  a gas outlet in fluid communication with the gas outlet of the blower.

11. The respiratory apparatus of claim 10, wherein the gas outlet is configured to connect to an air delivery tube and/or a humidifier.

12. A blower for providing a supply of air at positive pressure comprising:
 an air inlet;
 an air outlet;
 a housing having the shape of a volute; and
 an impeller coupled to an electric motor,
 wherein the impeller comprises only one shroud and a plurality of vanes extending from the shroud,
 wherein the shroud has a substantially wavy shaped outer circumference, and
 wherein each vane has a positive curvature in the direction of rotation from an intermediate diameter of the shroud toward the outer circumference of the shroud.

13. The blower of claim 12, wherein the air inlet is generally axially arranged with regard to the axis of rotation of the impeller.

14. The blower of claim 12, wherein the air outlet is tangentially arranged with regard to the axis of rotation of the impeller.

15. The blower of claim 12, wherein the blower is a radial blower.

16. The blower of claim 12, wherein the impeller has an inertia of less than about 3.2 g cm$^2$.

17. The blower of claim 12, wherein the impeller as an inertia of about 2.5 g cm$^2$.

18. The blower of claim 12, wherein the moment of inertia of the impeller lies in a range between about 1.2 and 3.2 g cm$^2$.

19. The blower of claim 12, wherein the moment of inertia of the impeller lies in a range between about 1.2 and 2.5 g cm$^2$.

20. The blower of claim 12, wherein the moment of inertia of the impeller is about 2.2 g cm$^2$.

21. The blower of claim 12, wherein the substantially wavy shaped outer circumference extends between a minimum diameter and a maximum diameter, wherein the minimum diameter is in a range of about 24 to 32 mm, and wherein the maximum diameter is in a range of about 38 to 46 mm.

22. The blower of claim 12, wherein the substantially wavy shaped outer circumference extends between a minimum diameter and a maximum diameter, wherein the minimum diameter is about 28 mm, and wherein the maximum diameter is about 42 mm.

23. The blower of claim 12, wherein the substantially wavy shaped outer circumference extends between a minimum diameter and a maximum diameter and the difference between the minimum and maximum diameter is about 4 to 22 mm.

24. The blower of claim 12, wherein the substantially wavy shaped outer circumference extends between a minimum diameter and a maximum diameter and the difference between the minimum and maximum diameter is about 10 to 18 mm.

25. The blower of claim 12, wherein the substantially wavy shaped outer circumference extends between a minimum diameter and a maximum diameter and the minimum diameter is reached between two adjacent vanes.

26. The blower of claim 12, wherein the air inlet is generally axially arranged with regard to the axis of rotation of the rotating portion,
    wherein the air outlet is tangentially arranged with regard to the axis of rotation of the rotating portion,
    wherein the blower is a radial blower,
    wherein the impeller has an inertia of less than about 3.2 g cm$^2$,
    wherein the substantially wavy shaped outer circumference extends between a minimum diameter and a maximum diameter, wherein the minimum diameter is in a range of about 24 to 32 mm,
    wherein the maximum diameter is in a range of about 38 to 46 mm,
    wherein the difference between the minimum and maximum diameter is about 4 to 22 mm, and
    wherein the minimum diameter is reached between two adjacent vanes.

27. A respiratory apparatus configured to treat a patient with a respiratory disorder, the respiratory apparatus comprising:
    the blower of claim 12;
    a housing that encloses the blower and comprises:
        an air inlet in fluid communication with the air inlet of the blower; and
        an air outlet in fluid communication with the air outlet of the blower.

28. The respiratory apparatus of claim 27, wherein the air outlet is configured to connect to an air delivery tube and/or a humidifier.

* * * * *